US012331020B2

(12) United States Patent
Hein et al.

(10) Patent No.: US 12,331,020 B2
(45) Date of Patent: Jun. 17, 2025

(54) METHOD OF SYNTHESIZING INDOLE COMPOUNDS

(71) Applicant: 1280225 B.C. LTD., Vancouver (CA)

(72) Inventors: Jason Ellis Hein, Vancouver (CA);
Corey Sanz, Vancouver (CA);
Shao-Kai Chen, Vancouver (CA);
Blessing Cao, Vancouver (CA)

(73) Assignee: 1280225 B.C. LTD., Vancouver (CA)

( * ) Notice: Subject to any disclaimer, the term of this patent is extended or adjusted under 35 U.S.C. 154(b) by 0 days.

(21) Appl. No.: 18/259,578

(22) PCT Filed: Dec. 17, 2021

(86) PCT No.: PCT/CA2021/051833
§ 371 (c)(1),
(2) Date: Jun. 27, 2023

(87) PCT Pub. No.: WO2022/140844
PCT Pub. Date: Jul. 7, 2022

(65) Prior Publication Data
US 2024/0059653 A1 Feb. 22, 2024

Related U.S. Application Data

(60) Provisional application No. 63/253,961, filed on Oct. 8, 2021, provisional application No. 63/133,056, filed on Dec. 31, 2020.

(51) Int. Cl.
*C07D 209/16* (2006.01)
*C07D 403/06* (2006.01)
*C07F 9/572* (2006.01)

(52) U.S. Cl.
CPC ......... *C07D 209/16* (2013.01); *C07D 403/06* (2013.01); *C07F 9/5728* (2013.01)

(58) Field of Classification Search
CPC .... C07D 209/16; C07D 403/06; C07F 9/5728
See application file for complete search history.

(56) References Cited

U.S. PATENT DOCUMENTS

| 5,571,833 A * | 11/1996 | Kruse | C07D 209/16 |
| | | | 514/415 |
| 8,901,317 B2 | 12/2014 | Bandyopadhyay et al. | |
| 10,519,175 B2 | 12/2019 | Londesbrough et al. | |
| 2008/0207728 A1* | 8/2008 | Wortmann | C07D 409/14 |
| | | | 549/469 |
| 2009/0298809 A1 | 12/2009 | Manning et al. | |
| 2013/0296281 A1 | 11/2013 | Kyle et al. | |

FOREIGN PATENT DOCUMENTS

| AU | 237777 B2 | 8/1959 | |
| CN | 111484436 A | 8/2020 | |
| CZ | 307719 B6 | 3/2019 | |
| DE | 19 17 128 A1 | 10/1969 | |
| GB | 911946 A | 12/1962 | |
| GB | 1226462 | 3/1971 | |
| GB | 2571696 A * | 9/2019 | ........... A61K 31/661 |
| WO | WO 2007/017289 A2 | 2/2007 | |
| WO | WO 2019/180309 A1 | 9/2019 | |

OTHER PUBLICATIONS

Prajapati et al., Tetrahedron Letters (2006), 47(21), 3535-3539. (Year: 2006).*
Dethe et al., Chemistry—A European Journal (2016), 22(1), 106-110. (Year: 2016).*
Dethe et al., Chemistry—A European Journal (2016), 22(1), 106-110, Supporting Information on pp. 1-76. (Year: 2016).*
Hayashi, Chemical Science, 2016, 7, 866-880. (Year: 2016).*
Bartolucci et al., Observations Concerning the Synthesis of Tryptamine Homologues and Branched Tryptamine Derivatives via the Borrowing Hydrogen Process: Synthesis of Psilocin, Bufotenin, and Serotonin. Tetrahedron May 2016;72(18): 2233-2238.
Blei et al., Biocatalytic Production of Psilocybin and Derivatives in Tryptophan Synthase-Enhanced Reactions. Chem Eur J. Jul. 17, 2018;24(40): 10028-10031.
Brown et al., 3-Indolylacetaldehyde and 3-Indolylacetone. J. Chem. Soc. (1952), 606, No. 0, 3172-3176.
Carhart-Harris et al., Psilocybin with Psychological Support for Treatment-Resistant Depression: An Open-Label Feasibility Study. Lancet Psych. Jul. 1, 2016;3(7): 619-627.
Chadeayne et al., Active Metabolite of Aeruginascin (4-Hydroxy-N,N,N-trimethyltryptamine): Synthesis, Structure, and Serotonergic Binding Affinity. ACS Omega. Jul. 2, 2020;5(27): 16940-16943.
Chen et al., Asymmetric Formal Synthesis of (+)-Cycloclavine. Chem Commun, 2017;53(96): 12902-12905.
Chung et al., The More, The Better: Simultaneous In Situ Reaction Monitoring Provides Rapid Mechanistic and Kinetic Insight. Top Catal. Jun. 2017;60: 594-608.
Corma et al., Advances in One-Pot Synthesis through Borrowing Hydrogen Catalysis. Chem Rev. Feb. 28, 2018;118(4): 1410-1459.
Daponte et al., Using an Automated Monitoring Platform for Investigations of Biphasic Reactions. ACS Catal. Nov. 4, 2019;9(12): 11484-11491.

(Continued)

*Primary Examiner* — Laura L Stockton
(74) *Attorney, Agent, or Firm* — Knobbe Martens Olson & Bear LLP

(57) ABSTRACT

A method of synthesizing indole compounds. The method may include allyllating an indole compound, oxidizing the resulting α-indolepropene, and reductively aminating the resulting indoleacetaldehyde, providing a tryptamine. The indole compound may be substituted with a functional group on the indole ring or may be unsubstituted indole. The method may include substitution, oxidation or other derivatization of the indole ring of the indole compound, of tryptophan, of the tryptamine, or of intermediates. The method may include oxidizing tryptophan or a ring-substituted tryptophan analogue and reductively aminating the resulting indoleacetaldehyde, providing a tryptamine. The method may be applied in a telescoped approach without isolation of intermediates. The method may be applied to production of indoles, α-indolepropenes, indole propyl diols, indoleacetaldehydes and tryptamines. Compounds from each of these classes of compounds are also provided herein.

19 Claims, 10 Drawing Sheets

(56) References Cited

OTHER PUBLICATIONS

Dethe et al., Novel Pd-Catalysed Annulation Reaction for the Syntheses of Pyrroloindoles and Pyrroloquinolines. Chemistry Jan. 4, 2016;22(1): 106-110.

Dethe et al., A. Biomimetic Total Syntheses of Borreverine and Flinderole Alkaloids. J Org Chem. Oct. 18, 2013;78(20): 10106-10120.

Fawzy A. Palladium(II)-Catalyzed Oxidation of L-Tryptophan by Hexacyanoferrate(III) in Perchloric Acid Medium: A Kinetic and Mechanistic Approach. J Chem Sci. Feb. 2016;128(2): 247-256.

Folen V.A., X-Ray Powder Diffraction Data for Some Drugs, Excipients, and Adulterants in Illicit Samples. J Forensic Sci. Apr. 1, 1975;20(2): 348-372.

Fricke et al., Enzymatic Synthesis of Psilocybin. Angew Chem Int. Ed. Sep. 25, 2017;56(40): 12352-12355.

Gathergood et al., Preparation of the 4-Hydroxytryptamine Scaffold via Palladium-Catalyzed Cyclization: A Practical and Versatile Synthesis of Psilocin. Org Lettr. Mar. 20, 2003;5(6): 921-923.

Geiger et al., DARK Classics in Chemical Neuroscience: Psilocybin. ACS Chem Neurosc. Jun. 29, 2018;9(10): 2438-2447.

Gray R. A., Preparation and Properties of 3-Indoleacetaldehyde. Arch Biochem Biophys. Apr. 1, 1959;81(2): 480-488.

Guo et al., Potential Application of Silicified Microcrystalline Cellulose in Direct-Fill Formulations for Automatic Capsule-Filling Machines. Pharma Develop Tech. Jan. 1, 2003;8(1): 47-59.

Hayashi Y., Pot Economy and One-Pot Synthesis. Chem Sci. 2016;7(2): 866-880.

Hu et al., Palladium-Catalyzed Synthesis of Tryptamines and Tryptamine Homologues: Synthesis of Psilocin. Tetrahedron Nov. 7, 2009;65(45): 9075-9080.

Hu et al., Catalytic Prenylation and Reverse Prenylation of Indoles with Isoprene: Regioselectivity Manipulation Through Choice of Metal Hydride. Angew. Chem Int Ed. Apr. 8, 2019;58(16): 5438-5442.

Julia et al., Synthese de La Psilocine a Partir de Dimethyl Tryptamine. C. R. Acad. Sc. Paris, (1969), 269(1), 51-53.

Kargbo et al., Direct Phosphorylation of Psilocin Enables Optimized cGMP Kilogram-Scale Manufacture of Psilocybin. ACS Omega. Jul. 1, 2020;5(27): 16959-16966.

Kimura et al., Pd-Catalyzed C3-Selective Allylation of Indoles with Allyl Alcohols Promoted by Triethylborane. J Am Chem Soc. Apr. 6, 2005;127(13): 4592-4593.

Kodet et al., Synthesis and Structure Activity Relationships of Schweinfurthin Indoles. Bioorg Med Chem. Apr. 15, 2014;22(8): 2542-2552.

Lv et al., Metal-Free Directed $sp^2$-C—H Borylation. Nature Nov. 14, 2019;575(7782): 336-340.

Malig et al., Development of a Telescoped Synthesis of 4-(1H)-Cyanoimidazole Core Accelerated by Orthogonal Reaction Monitoring. React Chem Eng., 2020; 5: 1421-1428.

Malig et al., Online High-Performance Liquid Chromatography Analysis of Buchwald-Hartwig Aminations from Within an Inert Environment. ACS Catal. Nov. 2, 2020;10(22): 13236-13244.

Maresh et al., Facile One-Pot Synthesis of Tetrahydroisoquinolines from Amino Acids via Hypochlorite-Mediated Decarboxylation and Pictet-Spengler Condensation. Tetra Lettr. Sep. 3, 2014;55(36): 5047-5051.

Mi et al., Selective Oxidative Cleavage of Terminal Olefins into Aldehydes Catalyzed by Copper(II) Complex. RSC Adv. 2015;5(85): 69487-69492.

Nichols D. E., Psychedelics. Pharmacol Rev. Apr. 1, 2016;68(2): 264-355.

Nichols et al., Improvements to the Synthesis of Psilocybin and a Facile Method for Preparing the O-Acetyl Prodrug of Psilocin. Synthesis. Jun. 1999;(06): 935-938.

Olsen et al., Marine AChE Inhibitors Isolated from *Geodia barretti*: Natural Compounds and Yheir Synthetic Analogs. Org Biomol Chem. 2016;14(5): 1629-1640.

Sato et al., Real-Time Monitoring of Solid-Liquid Slurries: Optimized Synthesis of Tetrabenazine. J Org Chem. Jul. 2, 2021;86(20): 14069-14078.

Shirota et al., Concise Large-Scale Synthesis of Psilocin and Psilocybin, Principal Hallucinogenic Constituents of "Magic Mushroom". J Nat Prod. Jun. 27, 2003;66(6): 885-887.

Shultz et al., Optimization of the in Vitro Cardiac Safety of Hydroxamate-Based Histone Deacetylase Inhibitors. J Med Chem. Jul. 14, 2011;54(13): 4752-4772.

Somei et al., A Five-Step Synthesis of Psilocin from Indole-3-Carbaldehyde. Heterocycles (1998), 49(1): 451-457.

Tamami et al., Modified Crosslinked Polyacrylamide Anchored Schiff Base-cobalt Complex: A Novel Nano-Sized Heterogeneous Catalyst for Selective Oxidation of Olefins and Alkyl Halides with Hydrogen Peroxide in Aqueous Media. Appl Catal. A Feb. 15, 2011;393(1-2): 242-250.

Xu et al., Construction of Erythrinane Skeleton via Pd(0)-Catalyzed Intramolecular Dearomatization of para-Aminophenols. J Am Chem Soc. Nov. 5, 2014;136(44): 15469-15472.

International Search Report and Written Opinion Received in PCT Application No. PCT/CA2021/051833 mailed on Mar. 22, 2022 in 8 pages.

Inuki et al., "Enantioselective Total Synthesis of (+)-Lysergic Acid, (+)-Lysergol, and (+)-Isolysergol by Palladium-Catalyzed Domino Cyclization of Allenes Bearing Amino and Bromoindolyl Groups" J. Org. Chem., vol. 76, No. 7, Mar. 1, 2011.

Kerkovius et al., "Total Synthesis of Isodihydrokoumine, (19Z)-Taberpsychine, and (4R)-Isodihydroukoumine N4-Oxide" J. Am. Chem. Soc., vol. 140, No. 27, Jun. 25, 2018.

Kerkovius et al., "Supporting Information: Total synthesis of isodihydrokoumine, (19Z)-taberpsychine, and (4R)-isodihydroukoumine N4-oxide" J. Am. Chem. Soc., vol. 140, No. 27, Jun. 25, 2018.

Mann et al., "A Novel Approach to the Skeletons of the Ergot Alkaloids and Secoergolines", Tetrahedron, vol. 51, No. 46, Nov. 13, 1995.

Partial Supplementary European Search Report issued in corresponding EP Application 21912369.2 dated Nov. 4, 2024.

* cited by examiner

METHOD OF SYNTHESIZING INDOLE COMPOUNDS

CROSS-REFERENCE TO RELATED APPLICATIONS

The present application is the U.S. national phase entry of PCT Application No. PCT/CA2021/051833, filed Dec. 17, 2021, and claims priority from U.S. Provisional Application No. 63/133,056, filed Dec. 31, 2020, and U.S. Provisional Application No. 63/253,961, filed Oct. 8, 2021 each of which are hereby incorporated by reference in their entireties.

FIELD

The present disclosure relates to synthesis of indole compounds.

BACKGROUND

Tryptamines are a valuable group of chemicals, with 5-hydroxy tryptamine ("5HT" or serotonin) being a commonly-studied neurotransmitter. Structural similarity to serotonin is correlated with pharmacological activity at 5HT receptors, including 5HT2A receptors. Agonistic activity at the 5HT2A receptor is associated with the pharmacology of many of the classical psychedelics, including tryptamines and phenethylamines. Recent increased interest in studies of psilocybin, psilocin, dimethyltryptamine ("DMT") and other tryptamines has increased the need for effective and efficient approaches to tryptamine synthesis.

Some approaches to synthesis of tryptamines include use of reagents that may be highly reactive, use of reagents that may be toxic, application of reaction mechanisms with have low efficiency or that may present other practical challenges to cost-effective scale up.

Oxidation of indole-3-carbaldehyde on the indole ring, followed by carbon homologation via cyanide and reduction is a known approach for synthesis of tryptamines (Somei, 1998). This approach uses thallium, which is toxic and unacceptable for synthesis to manufacture active pharmaceutical ingredients to good manufacturing practice standards.

Classical Fenton chemistry may be applied, which results in highly unselective mixed oxidation at positions 4, 5, 6 and 7 of the indole ring and also poly hydroxylation (Julia, 1969).

Other publications also relate to synthesis on tryptamines and other indole compounds (Geiger, 2018); (Fricke, 2017); (Nichols, 1999); (Somei, 1998); (Gathergood, 2003); (Shirota, 2003); (Kargbo, 2020); (Bartolucci, 2016); (Blei, 2018); (Chadeayne, 2020); (Kodet, 2014); (Hu, 2009).

Patent applications and issued patents relating to synthesis of tryptamines and other indole compounds include Chinese Patent Application No. 111484436, Aug. 4, 2020 to Faming et al., U.S. Pat. No. 10,519,175 issued on Dec. 31, 2019 to Londesbrough et. al., PCT Publication No. WO 2019/180309 published on Sep. 26, 2019 to Mojzita et al., U.S. Pat. No. 8,901,317 issued Dec. 2, 2014 to Bandyopadhyay, et al., PCT Publication No. WO 2007/017289 published on Feb. 15, 2007 to Wortmann et al., GB 911,946, AU 237,777 and CZ 307,719.

SUMMARY

In view of the shortcomings of previous approaches to tryptamine synthesis, there is motivation to provide efficient and cost-effective approaches to synthesis of ring-substituted and unsubstituted tryptamines and other indole compounds, with a variety of alkylation patterns on the amine group of tryptamines.

Generally, the present disclosure provides a method for synthesizing tryptamines and other indole compounds. The method may be applied to ring-substituted and unsubstituted tryptamines and other indole compounds. The method may be applied through a combination of two separate and related reactions, either of which may be applied first in sequence with the other. Oxidative decarboxylation followed by reductive amination converts tryptophan to a tryptamine. Oxidation on the indole ring derivatizes tryptophan or a tryptamine to provide a ring-substituted tryptophan analogue or a ring-substituted tryptamine. The method facilitates synthesis of tryptamines from tryptophan as a starting material, which may provide economic and other operational advantages.

Oxidative decarboxylation of tryptophan or of a ring-substituted analog of tryptophan, followed by reductive amination of the resulting indoleacetaldehyde, may produce for example DMT or psilocin. Oxidative decarboxylation of tryptophan or of a ring-substituted analog of tryptophan followed by reductive amination of the resulting indoleacetaldehyde may be carried out in a single telescoped reaction without isolation of the intermediate indoleacetaldehyde.

Selective or non-selective oxidation of the indole ring on tryptophan provides a ring-substituted tryptophan analogue, which may be applied where oxidation of the indole ring precedes oxidative decarboxylation and reductive amination. Selective or non-selective oxidation of the indole ring on a tryptamine provides a ring-substituted tryptamine, which may be applied where oxidative decarboxylation and reductive amination precede oxidation of the indole ring.

Oxidation of the indole ring on either tryptophan or the tryptamine results in a hydroxylated indole ring, which may be subsequently phosphorylated or otherwise derivatized, and whether maintained as a hydroxyl or otherwise derivatized, providing a ring-substituted tryptamine or ring-substituted tryptamine analogue.

Oxidative decarboxylation and reductive amination may include ethanolic oxidative decarboxylation, followed by reductive amination with a borohydride or any suitable reducing agent. These two reactions are facilitated by mutually exclusive reaction conditions and a switch from oxidative to reductive conditions may be facilitated by a change in pH or other conditions before, after or during addition of the aminating reagent. Oxidative decarboxylation and reductive amination may be applied to tryptophan to provide a tryptamine without substitutions on the indole ring. Oxidative decarboxylation and reductive amination may be applied to a ring-substituted tryptophan analogue to provide a ring-substituted tryptamine. Depending on the nucleophilic amine used for reductive amination, any suitable alkylation pattern may be provided on the amine, including two separate alkyl groups that are identical (e.g. DMT, DET, DiPT, etc.), two separate alkyl groups that are distinct (e.g. MET, MiPT, etc.), or one cyclic tertiary amine where both alkyl groups are part of a ring (e.g. a pyrrolidinyl tryptamine, etc.).

Oxidation of the indole ring may be undertaken by classical Fenton chemistry, which is highly unselective and results in mixed oxidation at positions 4,5,6 and 7, and also in polyhydroxylation. A complex mixture of products with different OH insertion positions may be isolated and then the mixture of products may be selectively separated and isolated through application of continuous crystallization, fractional crystallization or other suitable isolation techniques. Indole ring oxidation may be undertaken with protecting groups and borylation or other functionalization of the ring, facilitating selective oxidation of the 4 position on tryptophan to provide 4-hydroxyl tryptamines, which may be recovered as a product or may be derivatized to provide other 4-substituted tryptamines. Chelation control may be responsible for the selectivity at the 4 position. Sequential reactions of borylation or other derivatization followed by hydrolysis may facilitate hydroxylation at C-4 of some appropriate indole. Applying chelation control to functionalize the indole CH at position 4 is reported with thallium, which due to toxicity is inconsistent with compliance with good manufacturing practices ("GMP") for active pharmaceutical ingredients. After oxidative substitution on the indole ring, a number of different functional groups may be substituted for the hydroxyl group on the indole ring (e.g. —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H, SiR$_3$, wherein R is selected from the group consisting of alkyl, acyl, vinyl, propargyl, phenyl, benzyl, or other suitable groups, and each separate R group may be identical to other R groups or distinct from other R groups).

Alternatively to application of oxidative decarboxylation followed by reductive amination, in combination with indole ring oxidation, the method may be applied through adding an allyl group to a ring-substituted indole compound for providing a ring-substituted α-indolepropene. The ring-substituted α-indolepropene may be oxidized, a providing ring-substituted indoleacetaldehyde. The ring-substituted indoleacetaldehyde may be reductively aminated, providing the tryptamine. The nucleophilic character of the 3-position of the indole ring may facilitate attaching an allyl group to the indole ring. The allyl group is oxidized to an aldehyde, and an amino group is added to the aldehyde by reductive amination.

Similarly, the method may be applied through adding an allyl group to unsubstituted indole for providing an unsubstituted α-indolepropene. The method may be applied to any indole wherein position 3 of indole is an sp2 CH, and position 1 of indole of indole is unfunctionalized NG. Unsubstituted indole may be allylated to unsubstituted α-indolepropene. An unsubstituted α-indolepropene has no functional groups on the indole ring. All sp2 indole carbons carry a hydrogen on an unsubstituted α-indolepropene. The unsubstituted α-indolepropene may be oxidized to an unsubstituted indoleacetaldehyde. An unsubstituted indoleacetaldehyde has no functional groups on the indole ring. All sp2 indole carbons carry a hydrogen. The unsubstituted indoleacetaldehyde may be reductively aminated to an unsubstituted tryptamine. An unsubstituted tryptamine has no functional groups on the indole ring. All sp2 indole carbons carry a hydrogen.

By beginning with a substituted indole, which may be at the 4-, 5- or other positions on the indole ring (using the numbering of tryptamine as shown in FIG. 2), psilocin or another 4-substituted tryptamine, or 5-MeO-DMT or another 5-substituted tryptamine, may be produced. The alkylaminoethyl group in a tryptamine is first added to ring-substituted indole as an allyl group, oxidized to an aldehyde and then reduced to an amine group.

Conversion of the alkene resulting from allylation of the substituted indole to an intermediate aldehyde through a diol intermediate, with subsequent coupling of the resulting indoleacetaldehyde to a dialkylamine or other amine via reductive amination may be carried out as a telescoped process without isolation of any intermediates. Similarly, other steps from within the method may be carried out as a telescoped process without isolation of any intermediates. The present disclosure provides a direct alkene to aldehyde conversion on a 4-substituted indole (using the numbering of tryptamine as shown in FIG. 2) or other indoles, including by metalperoxo catalyzed transfer on the substituted indole. The present disclosure provides conversion of a terminal alkene to a tryptamine product through application of reductive amination by way of an intermediate diol and aldehyde without workup or isolation of any intermediates.

As detailed above in relation to the two-step process including oxidative decarboxylation and reductive amination, synthesis of hydroxylated ring-substituted tryptamines (e.g. psilocin) may in turn facilitate synthesis of phosphorylated, acetylated or other ring-substituted tryptamines (e.g. psilocybin, 4-acetyl-DMT, etc.), which may facilitate diversity in the number of tryptamines that can be synthesized by facilitating application of a variety of indole compound starting materials.

The flexibility of the methods provided herein to synthesize ring-substituted tryptamines or other indole compounds with a variety of functional groups on the indole ring, and unsubstituted tryptamines or other indole compounds, each with a variety of alkylation patterns, may provide advantages in drug discovery. Different leaving groups may facilitate unmasking of the hydroxyl to access psilocin. The electron withdrawing character of an acetyl group may complicate the reaction. In general, the added electronegativity of such functionalized indoles results in competing N-functionalized derivatives, impacting yield and synthetic throughput. Allylation at position 3 of indoles with a C-4 hydroxylated indole or similar C-4 functionality provides a synthetic approach to psilocybin, psilocin or other 4-substituted tryptamines with a variety of substituents on the ring (e.g. —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H, SiR$_3$, wherein R is selected from the group consisting of alkyl, acyl, vinyl, propargyl, phenyl, benzyl, or other suitable groups, and each separate R group may be identical to other R groups or distinct from other R groups) and a variety of substituents on the amine.

Novel 4-substituted indole compounds are also disclosed herein, including 4-acetylated indole compounds, 4-diphenylphoryloxy indole compounds and 4-sulfurofluoridyl indole compounds. These ring-substituted indole compounds may include tryptamines, allyl indoles, 2,3 dihydroxy propyl indoles and ethynal indoles.

In a first aspect, herein provided is a method of synthesizing indole compounds. The method may include allyllating an indole compound, oxidizing the resulting α-indolepropene, and reductively aminating the resulting indoleacetaldehyde, providing a tryptamine. The indole compound may be substituted with a functional group on the indole ring or may be unsubstituted indole. The method may include substitution, oxidation or other derivatization of the indole ring of the indole compound, of tryptophan, of the tryptamine, or of intermediates. The method may include oxidizing tryptophan or a ring-substituted tryptophan analogue and reductively aminating the resulting indoleacetaldehyde, providing a tryptamine. The method may be applied in a telescoped approach without isolation of intermediates.

The method may be applied to production of indoles, α-indolepropenes, indole propyl diols, indoleacetaldehydes and tryptamines. Compounds from each of these classes of compounds are also provided herein In a further aspect, herein provided is a method of synthesizing a tryptamine comprising: providing a substituted indole compound comprising an indole ring and a functional group on the indole ring; allyllating the substituted indole compound to provide a ring-substituted α-indolepropene; oxidizing the α-indolepropene to provide a ring-substituted indoleacetaldehyde; and reductively aminating the indoleacetaldehyde to provide the tryptamine.

In some embodiments, the functional group is selected from the group consisting of —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H and SiR$_3$, wherein R is selected from the group consisting of alkyl, acyl, vinyl, propargyl, phenyl and benzyl, and each separate R group may be identical to other R groups or distinct from other R groups. In some embodiments, the functional group is selected from the group consisting of —COCH$_3$, —PO$_2$(OR)$_2$ wherein R is benzyl, and —SO$_3$F. In some embodiments, the functional group is located on position 4 of the indole ring, using the numbering of tryptamine. In some embodiments, the functional group is located on position 5 of the indole ring, using the numbering of tryptamine. In some embodiments, functional group is located on position 6 of the indole ring, using the numbering of tryptamine. In some embodiments, the functional group is located on position 7 of the indole ring, using the numbering of tryptamine. In some embodiments, oxidizing the α-indolepropene comprises: oxidizing the α-indolepropene to provide an indole propyl diol; and oxidizing the indole propyl diol to provide the indoleacetaldehyde. In some embodiments, allyllating the substituted indole compound and oxidizing the α-indolepropene to provide the indole propyl diol are effected without isolation of intermediates. In some embodiments, oxidizing the α-indolepropene to provide the indole propyl diol and oxidizing the indole propyl diol are effected without isolation of intermediates. In some embodiments, oxidizing the indole propyl diol and reductively aminating the indoleacetaldehyde are effected without isolation of intermediates. In some embodiments, reductively aminating the indoleacetaldehyde comprises reductive amination with dimethylamine. In some embodiments, reductively aminating the indoleacetaldehyde comprises reductive amination with an amine selected from the group consisting of methylamine, ethylamine, isopropylamine, diethylamine, diisopropylamine, methylethylamine, methylisopropylamine and ethylisopropylamine. In some embodiments, reductively aminating the indoleacetaldehyde comprises reductive amination with a secondary amine and the tryptamine comprises a cyclic tertiary amine. In some embodiments, allyllating the substituted indole compound and oxidizing the α-indolepropene are effected without isolation of intermediates. In some embodiments, oxidizing the α-indolepropene and reductively aminating the indoleacetaldehyde are effected without isolation of intermediates. In some embodiments, the method includes substituting a functional group on the indole ring for another functional group.

In a further aspect, herein provided is a method of synthesizing a tryptamine comprising: providing unsubstituted indole; allyllating the indole to provide α-indolepropene; oxidizing the α-indolepropene to provide indoleacetaldehyde; and reductively aminating the indoleacetaldehyde to provide the tryptamine.

In some embodiments, oxidizing the α-indolepropene comprises: oxidizing the α-indolepropene to provide an indole propyl diol; and oxidizing the indole propyl diol to provide the indoleacetaldehyde. In some embodiments, allyllating the substituted indole compound and oxidizing the α-indolepropene to provide the indole propyl diol are effected without isolation of intermediates. In some embodiments, oxidizing the α-indolepropene to provide the indole propyl diol and oxidizing the indole propyl diol are effected without isolation of intermediates. In some embodiments, oxidizing the indole propyl diol and reductively aminating the indoleacetaldehyde are effected without isolation of intermediates. In some embodiments, reductively aminating the indoleacetaldehyde comprises reductive amination with dimethylamine. In some embodiments, reductively aminating the indoleacetaldehyde comprises reductive amination with an amine selected from the group consisting of methylamine, ethylamine, isopropylamine, diethylamine, diisopropylamine, methylethylamine, methylisopropylamine and ethylisopropylamine. In some embodiments, reductively aminating the indoleacetaldehyde comprises reductive amination with a secondary amine and the tryptamine comprises a cyclic tertiary amine. In some embodiments, allyllating the substituted indole compound and oxidizing the α-indolepropene are effected without isolation of intermediates. In some embodiments, oxidizing the α-indolepropene and reductively aminating the indoleacetaldehyde are effected without isolation of intermediates.

In a further aspect, herein provided is a method of synthesizing a ring-substituted α-indolepropene comprising: providing a substituted indole compound comprising an indole ring and a functional group on the indole ring; and allyllating the substituted indole compound to provide the α-indolepropene In some embodiments, the functional group is selected from the group consisting of —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H and SiR$_3$, wherein R is selected from the group consisting of alkyl, acyl, vinyl, propargyl, phenyl and benzyl, and each separate R group may be identical to other R groups or distinct from other R groups. In some embodiments, the functional group is selected from the group consisting of —COCH$_3$, —PO$_2$(OR)$_2$ wherein R is benzyl, and —SO$_3$F. In some embodiments, the functional group is located on position 4 of the indole ring, using the numbering of tryptamine. In some embodiments, the functional group is located on position 5 of the indole ring, using the numbering of tryptamine. In some embodiments, the functional group is located on position 6 of the indole ring, using the numbering of tryptamine. In some embodiments, the functional group is located on position 7 of the indole ring, using the numbering of tryptamine.

In a further aspect, herein provided is a method of synthesizing an indole propyl diol comprising: providing a ring-substituted α-indolepropene comprising an indole ring and a functional group on the indole ring; and oxidizing the α-indolepropene to provide the indole propyl diol.

In some embodiments, the α-indolepropene comprises: providing a substituted indole compound; and allyllating the substituted indole compound to provide the α-indolepropene. In some embodiments, allyllating the substituted indole compound and oxidizing the α-indolepropene are effected without isolation of intermediates. In some embodiments, the functional group is selected from the group consisting of —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$), —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H and SiR$_3$, wherein R is selected from the group consisting of alkyl, acyl, vinyl, propargyl, phenyl and benzyl, and each separate R group may be identical to other R groups or distinct from other R groups. In some embodiments, the functional group is selected from the group consisting of —COCH$_3$, —PO$_2$(OR)$_2$ wherein R is benzyl, and —SO$_3$F. In some embodiments, the functional group is located on position 4 of the indole ring, using the numbering of tryptamine. In some embodiments, the functional group is located on position 5 of the indole ring, using the numbering of tryptamine. In some embodiments, the functional group is located on position 6 of the indole ring, using the numbering of tryptamine. In some embodiments, the functional group is located on position 7 of the indole ring, using the numbering of tryptamine.

In a further aspect, herein provided is a method of synthesizing a tryptamine comprising: providing a ring-substituted indoleacetaldehyde comprising an indole ring and a functional group on the indole ring; and reductively aminating the indoleacetaldehyde to provide the tryptamine.

In some embodiments, wherein providing the indoleacetaldehyde comprises: providing a ring-substituted α-indolepropene; and oxidizing the α-indolepropene to provide the indoleacetaldehyde. In some embodiments, oxidizing the α-indolepropene and reductively aminating the indoleacetaldehyde are effected without isolation of intermediates. In some embodiments, oxidizing the α-indolepropene comprises: oxidizing the α-indolepropene to provide an indole propyl diol; and oxidizing the indole propyl diol to provide the indoleacetaldehyde. In some embodiments, oxidizing the α-indolepropene to provide the indole propyl diol and oxidizing the indole propyl diol are effected without isolation of intermediates. In some embodiments, oxidizing the indole propyl diol and reductively aminating the indoleacetaldehyde are effected without isolation of intermediates. In some embodiments, providing the α-indolepropene comprises: providing a substituted indole compound; and allyllating the substituted indole compound to provide the α-indolepropene. In some embodiments, allyllating the substituted indole compound and oxidizing the α-indolepropene are effected without isolation of intermediates. In some embodiments, reductively aminating the indoleacetaldehyde comprises reductive amination with dimethylamine. In some embodiments, reductively aminating the indoleacetaldehyde comprises reductive amination with an amine selected from the group consisting of methylamine, ethylamine, isopropylamine, diethylamine, diisopropylamine, methylethylamine, methylisopropylamine and ethylisopropylamine. In some embodiments, reductively aminating the indoleacetaldehyde comprises reductive amination with a secondary amine and the tryptamine comprises a cyclic tertiary amine. In some embodiments, the functional group is selected from the group consisting of —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H and SiR$_3$, wherein R is selected from the group consisting of alkyl, acyl, vinyl, propargyl, phenyl and benzyl, and each separate R group may be identical to other R groups or distinct from other R groups. In some embodiments, the functional group selected from the group consisting of —COCH$_3$, —PO$_2$(OR)$_2$ wherein R is benzyl, and —SO$_3$F. In some embodiments, the functional group is located on position 4 of the indole ring, using the numbering of tryptamine. In some embodiments, the functional group is located on position 5 of the indole ring, using the numbering of tryptamine. In some embodiments, the functional group is located on position 6 of the indole ring, using the numbering of tryptamine. In some embodiments, the functional group is located on position 7 of the indole ring, using the numbering of tryptamine.

In a further aspect, herein provided is a method of synthesizing a tryptamine comprising: providing tryptophan; oxidizing the tryptophan to provide indoleacetaldehyde; and reductively aminating the indoleacetaldehyde to provide the tryptamine; wherein oxidizing the tryptophan and reductively aminating the indoleacetaldehyde are effected without isolation of intermediates.

In some embodiments, reductively aminating the indoleacetaldehyde comprises reductive amination with dimethylamine. In some embodiments, reductively aminating the indoleacetaldehyde comprises reductive amination with an amine selected from the group consisting of methylamine, ethylamine, isopropylamine, diethylamine, diisopropylamine, methylethylamine, methylisopropylamine and ethylisopropylamine. In some embodiments, reductively aminating the indoleacetaldehyde comprises reductive amination with a secondary amine and the tryptamine comprises a cyclic tertiary amine. In some embodiments, the method includes oxidizing an indole ring of the tryptamine to provide a ring-substituted tryptamine comprising a functional group on the indole ring. In some embodiments, oxidizing the indole ring comprises application of Fenton chemistry and the ring-substituted tryptamine comprises a tryptamine substituted on the indole ring with —OH. In some embodiments, the functional group is selected from the group consisting of —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H and SiR$_3$, wherein R is selected from the group consisting of alkyl, acyl, vinyl, propargyl, phenyl and benzyl, and each separate R group may be identical to other R groups or distinct from other R groups. In some embodiments, the functional group is located on position 4 of the indole ring, using the numbering of tryptamine. In some embodiments, the functional group is located on position 5 of the indole ring, using the numbering of tryptamine. In some embodiments, the functional group is located on position 6 of the indole ring, using the numbering of tryptamine. In some embodiments, oxidizing the tryptophan, reductively aminating the indoleacetaldehyde and oxidizing the indole ring of the tryptamine are effected without isolation of intermediates.

In a further aspect, herein provided is a method of synthesizing a ring-substituted tryptamine comprising: providing tryptophan; oxidizing an indole ring of the tryptophan to provide a ring-substituted tryptophan analogue comprising a functional group on the indole ring; oxidizing the tryptophan analogue to provide a ring-substituted indoleacetaldehyde; and reductively aminating the indoleacetaldehyde to provide the tryptamine.

In some embodiments, oxidizing the indole ring comprises oxidizing the indole ring by application of Fenton chemistry and the tryptophan analogue comprises a tryptophan analogue substituted on the indole ring with —OH. In some embodiments, the functional group is selected from the group consisting of —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H and SiR$_3$, wherein R is selected from the group consisting of alkyl, acyl, vinyl, propargyl, phenyl and benzyl, and each separate R group may be identical to other R groups or distinct from other R groups. In some embodiments, the functional group is located on position 4 of the indole ring, using the numbering of tryptamine. In some embodiments, the functional group is located on position 5 of the indole ring, using the numbering of tryptamine. In some embodiments, the functional group is located on position 6 of the indole ring, using the numbering of tryptamine. In some embodiments, reductively aminating the indoleacetaldehyde comprises reductive amination with dimethylamine. In some embodiments, reductively aminating the indoleacetaldehyde comprises reductive amination with an amine selected from the group consisting of methylamine, ethylamine, isopropylamine, diethylamine, diisopropylamine, methylethylamine, methylisopropylamine and ethylisopropylamine. In some embodiments, reductively aminating the indoleacetaldehyde comprises reductive amination with a secondary amine and the tryptamine comprises a cyclic tertiary amine. In some embodiments, oxidizing the indole ring and oxidizing the tryptophan analogue are effected without isolation of intermediates. In some embodiments, oxidizing the tryptophan analogue and reductively aminating the indoleacetaldehyde are effected without isolation of intermediates. In some embodiments, oxidizing an indole ring of the tryptophan, oxidizing the tryptophan analogue and reductively aminating the indoleacetaldehyde are effected without isolation of intermediates.

In a further aspect, herein provided is an indole compound having the general formula (I):

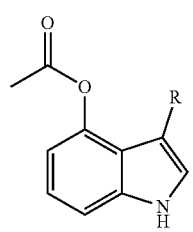

(I)

wherein R is selected from the group consisting of allyl, 2,3 dihydroxy propyl, ethynal and ethyl pyrrolidine.

In a further aspect, herein provided is an indole compound having the general formula (II):

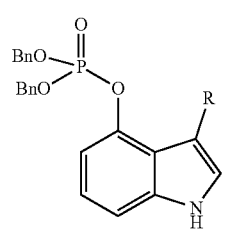

(II)

wherein R is selected from the group consisting of H, allyl, 2,3 dihydroxy propyl, ethynal and ethyl pyrrolidine.

In a further aspect, herein provided is an indole compound having the general formula (III):

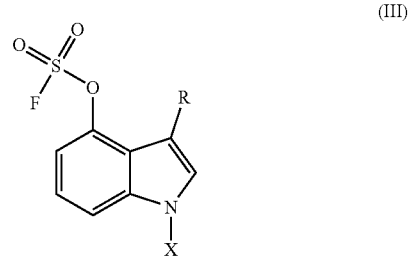

(III)

wherein R is selected from the group consisting of allyl, 2,3 dihydroxy propyl, ethynal and CH$_2$CH$_2$NR1R2, R1 is selected from the group consisting of C1 to C6 alkyl, R$_2$ is selected from the group consisting of C1 to C6 alkyl; and X is selected from the group consisting of H, —COR", —CO$_2$R", —CONR"$_2$, —PO(OR")$_2$, —SiR"$_3$, —SO$_2$(OR"), and —SO$_2$F, wherein R" is selected from the group consisting of alkyl, acyl, vinyl, propargyl, phenyl and benzyl, and each separate R" group may be identical to other R" groups or distinct from other R" groups.

In some embodiments, R is CH$_2$CH$_2$NR1R2; the N in CH$_2$CH$_2$NR1R2 is a tertiary amine; and R$_1$ and R$_2$ are one continuous alkyl group.

In some embodiments, the X group has the following structure when bonded to the indole ring:

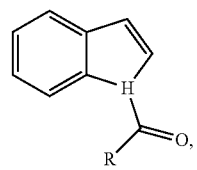

where the indole ring

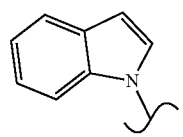

is the indole ring of general formula (III).

In some embodiments, the X group has the following structure when bonded to the indole ring:

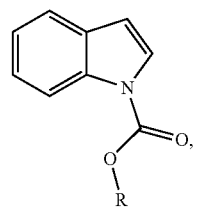

where the indole ring

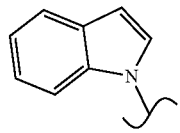

is the indole ring of general formula (III).

In some embodiments, the X group has the following structure when bonded to the indole ring:

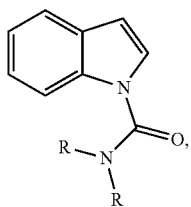

where the indole ring

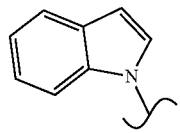

is the indole ring of general formula (III).

In some embodiments, the X group has the following structure when bonded to the indole ring:

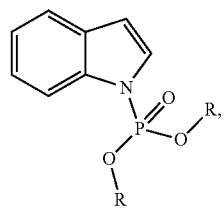

where the indole ring

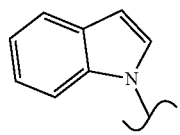

is the indole ring of general formula (III).

In some embodiments, the X group has the following structure when bonded to the indole ring:

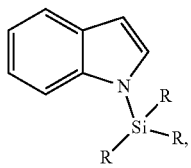

where the indole ring is

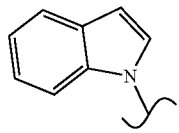

is the indole ring of general formula (III).

In some embodiments, the X group has the following structure when bonded to the indole ring:

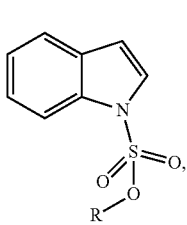

where the indole ring

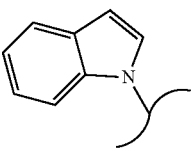

is the indole ring of general formula (III).

In some embodiments, the X group has the following structure when bonded to the indole ring:

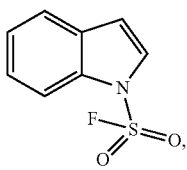 [SMILES: O=S(=O)(F)n1ccc2ccccc21]

where the indole ring

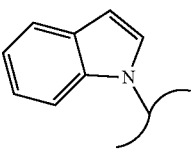

is the indole ring of general formula (III).

In some embodiments, the N at position 1 of the indole ring, using the numbering of tryptamine, comprises an —SO$_2$F functional group.

In one or more embodiments as described herein, there is provided is an indole compound having the general formula:

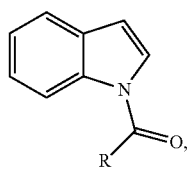

wherein the indole ring

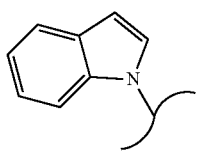

is a substituted or unsubstituted indole as described herein, and the R group is selected from the group consisting of alkyl, acyl, vinyl, propargyl, phenyl and benzyl.

In one or more embodiments as described herein, there is provided is an indole compound having the general formula:

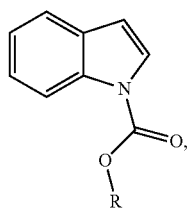

where the indole ring

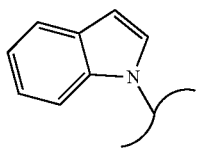

is a substituted or unsubstituted indole as described herein, and the R group is selected from the group consisting of alkyl, acyl, vinyl, propargyl, phenyl and benzyl.

In one or more embodiments as described herein, there is provided is an indole compound having the general formula:

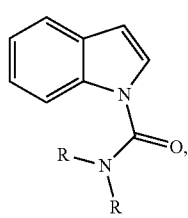

where the indole ring

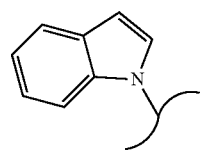

is a substituted or unsubstituted indole as described herein, and the R group is selected from the group consisting of alkyl, acyl, vinyl, propargyl, phenyl and benzyl, and each separate R group may be identical to other R groups or distinct from other R groups.

In one or more embodiments as described herein, there is provided is an indole compound having the general formula:

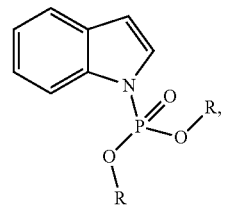

where the indole ring

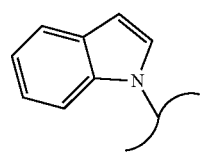

is a substituted or unsubstituted indole as described herein, and the R group is selected from the group consisting of alkyl, acyl, vinyl, propargyl, phenyl and benzyl, and each separate R group may be identical to other R groups or distinct from other R groups.

In one or more embodiments as described herein, there is provided is an indole compound having the general formula:

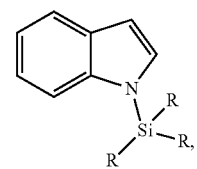

where the indole ring

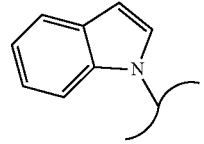

is a substituted or unsubstituted indole as described herein, and the R group is selected from the group consisting of alkyl, acyl, vinyl, propargyl, phenyl and benzyl, and each separate R group may be identical to other R groups or distinct from other R groups.

In one or more embodiments as described herein, there is provided is an indole compound having the general formula:

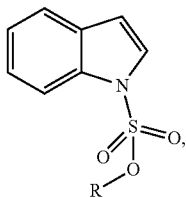

where the indole ring

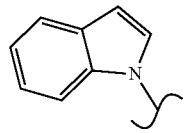

is a substituted or unsubstituted indole as described herein, and the R group is selected from the group consisting of alkyl, acyl, vinyl, propargyl, phenyl and benzyl.

In one or more embodiments as described herein, there is provided is an indole compound having the general formula:

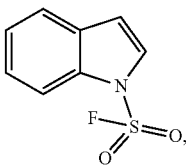

where the indole ring

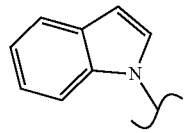

is a substituted or unsubstituted indole as described herein.

Other aspects and features of the present disclosure will become apparent to those ordinarily skilled in the art upon review of the following description of specific embodiments in conjunction with the accompanying figures

BRIEF DESCRIPTION OF THE FIGURES

Embodiments of the present disclosure will now be described, by way of example only, with reference to the attached Figures.

DETAILED DESCRIPTION

Figure 1:
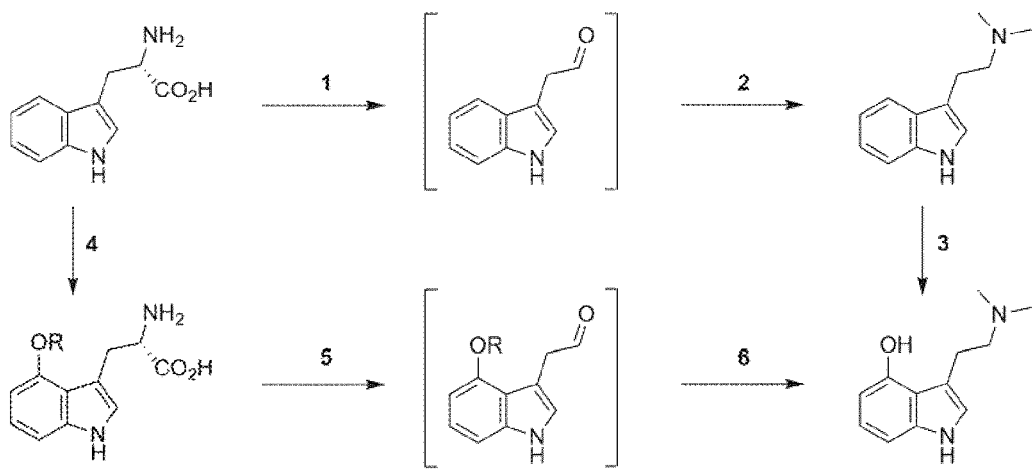
FIG. 1 shows reaction schemes for synthesis of ring-substituted and unsubstituted tryptamines from tryptophan.

Generally, the present disclosure provides a method for synthesizing tryptamines and other indole compounds. The method may be applied to ring-substituted or unsubstituted tryptamines and other compounds. Ring-substituted tryptamines and other compounds include functional groups on the indole ring of tryptamine such as —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H, SiR$_3$, wherein R is selected from the group consisting of alkyl, acyl, vinyl, propargyl, phenyl, benzyl, or other suitable groups, and each separate R group may be identical to other R groups or distinct from other R groups. The method may be applied to tryptamines or other indole compounds lacking functional groups on the indole ring and to tryptamines or other indole compounds with ring substitutions. The tryptamines may be alkylated on the terminal amine group with any suitable alkylation pattern. Alkylation patterns on the terminal amine may include methyl, ethyl, isopropyl, dimethylamine diethyl, diisopropyl, methylethyl, methylisopropyl and ethylisopropyl. Alkylation patterns on the terminal amine group may be cyclic tertiary amine groups, including an unconjugated pyrrolyl group with entirely sp3 orbital configuration on the alkyl amine. Other cyclic tertiary amines, whether conjugated or not, may also be applied to create cyclic tertiary amines (e.g. aromatic pyrrolyl, piperidinyl, pyridinyl, etc.).

The method may be applied through two separate and related reactions. Oxidative decarboxylation of tryptophan or of a ring-substituted analog of tryptophan followed by reductive amination of the resulting aldehyde may be applied to synthesize a tryptamine. Oxidative decarboxylation of tryptophan or of a ring-substituted analog of tryptophan followed by reductive amination of the resulting aldehyde may be carried out in a single telescoped reaction without isolation of any intermediates. There is no previous report of a direct oxidation of tryptophan that is fed directly to reductive amination of an aldehyde without workup or isolation of intermediates. This telescoped sequence provides efficiencies. The switch from oxidative to reductive with effective coupling of the two reaction conditions is facilitated by close monitoring and control of reaction conditions. Selective or non-selective oxidation of the indole ring on tryptophan may provide a ring-substituted tryptophan analogue. Selective or non-selective oxidation of the indole ring on a tryptamine may provide a ring-substituted tryptamine. This approach allows use of tryptophan as a starting material, which may provide economic or other operational advantages relative to syntheses using other starting materials.

Oxidative decarboxylation of tryptophan followed by reductive amination of the resulting aldehyde may be applied to tryptophan to provide a tryptamine without substitutions on the indole ring (e.g. N,N-dimethyltryptamine ("DMT"), N,N-diethyltryptamine ("DET"), N,N,methylethyltryptamine ("MET"), N,N,methylisopropyltryptamine ("MiPT"), N,N-diisopropyltryptamine ("DiPT"), etc.).

Selective or non-selective oxidation of the indole ring on either tryptophan or the tryptamine results in a hydroxylated indole ring, which may be subsequently phosphorylated or otherwise derivatized, and whether maintained as a hydroxyl or otherwise derivatized, providing a ring-substituted tryptamine (e.g. 3-[2-(dimethylamino)ethyl]-4-phosphoryloxyindole (psilocybin), 3-[2-(dimethylamino)ethyl]-4-hydroxyindole (psilocin), 3-[2-(dimethylamino)ethyl]-4-acetoxyindole ("4-acetyl-DMT"), 3-[2-(trimethylamino)ethyl]-4-phosphoryloxyindole (aeruginascin), 3-[2-(methylamino)ethyl]-4-phosphoryloxyindole (baeocystin), 3-[2-(methylamino)ethyl]-4-hydroxyindole, 3-[2-(amino)ethyl]-4-hydroxyindole (norpsilocin), 3-[2-(amino)ethyl]-4-phosphoryloxyindole (norbaeocystin), 5-methoxy-dimethyltryptamine (bufotenin), 5-methoxy-diisopropyltryptamine ("5-MeO-DiPT"), N-acetyl-5-methoxy tryptamine (melatonin), 5-hydroxy tryptamine (serotonin), 5-methoxy-dimethyltryptamine ("5-MeO-DMT"), and 5-hydroxy-tryptophan ("5-HTP").

The method may be applied to adding alkyl functionality to a ring-substituted indole compound. The nucleophilic character of the 3-position of the indole ring may facilitate attaching a dimethylaminoethyl at the 3-position, resulting in tryptamine. An allyl group is added to the substituted indole compound. The resulting ring-substituted α-indolepropene is oxidized to an indoleacetaldehyde. The resulting indoleacetaldehyde is reductively aminated to a tryptamine.

The allyl group may be bonded to the indole ring, oxidized to an indole propyl diol, oxidized to an aldehyde, and reduced to a dialkylamino, or other amine group (e.g. dimethylamino-, diethylamino-, diisopropylamino-, methylethylamino-, pyrolidine or other group). By beginning with 4-hydroxy-indole or another 4-substituted indole, using the same numbering as on tryptamines, psilocin or another a 4-substituted tryptamine results from alkylation. By beginning with 5-hydroxy-indole or another 5-substituted indole, using the same numbering as on tryptamines, bufotenine or another a 5-substituted tryptamine results from alkylation.

Synthesis of hydroxylated ring-substituted tryptamines (e.g. psilocin) as an initial step may in turn facilitate synthesis of phosphorylated, acetylated or other ring-substituted indole compounds (e.g. psilocybin, 4-acetyl-DMT, etc.), which may facilitate diversity in the number of tryptamines that can be synthesized by facilitating application of a variety of indole compound starting materials. Phosphorylation or other derivatization of hydroxylated ring-substituted indole compound may be completed through a number of organic chemistry or biosynthetic methods. Psilocybin is a prodrug of psilocin. Analogues of psilocybin in which the phosphate is substituted by bio-convertible groups may provide new chemical entities with different pharmacokinetics than psilocybin.

Analogues of psilocybin where the alkylation pattern is not dimethyl may provide new chemical entities with different pharmacokinetics, pharmacodynamics or other properties, compared with psilocybin. Analogues of psilocybin where the ring substituent is a different functional group, is located at a different position on the ring or both may also be produced with the method. Other bio-convertible groups could potentially provide advantages such as longer or shorter duration of effect, extended release, specialized therapeutic indication, or other advantages. The flexibility of the methods provided herein to synthesize ring-substituted tryptamines with a variety of functional groups on the indole ring, and unsubstituted tryptamines, each with a variety of alkylation patterns, may provide advantages in drug discovery, and other aspects of research and development of therapeutic products.

FIG. 1 shows two reaction pathways: (a) oxidative decarboxylation and reductive amination shown at Steps 1 to 2 and Steps 5 to 6 and (b) oxidation of the indole ring at Step 3 and Step 4. Step 4 may precede Steps 5 to 6. Steps 1 to 2 may precede Step 3.

In FIG. 1, Steps 1 to 2 and 5 to 6 include tryptamine synthesis from amino acid in one telescoped series of reactions that includes sequential oxidative decarboxylation and reductive amination without isolation of any intermediates. In the example of FIG. 1, the tryptamine is N,N-DMT, but other tryptamines may be synthesized by varying the amine used for reductive amination of indoleacetaldehyde. The amino acid may be tryptophan (steps 1 and 2) or ring-substituted tryptophan analogues (steps 5 and 6). While only 4-substituted tryptamines and tryptophan analogues are shown in FIG. 1, other ring substitution patterns may also be applied in the method.

The two telescoped steps of oxidative decarboxylation and reductive amination could be completed on either tryptophan (step 1 and 2 in FIG. 1) or 4-hydroxy tryptophan (steps 5 and 6 in FIG. 1). The conditions where oxidative decarboxylation and reductive amination overlap is a narrow window of reaction conditions. Timing of the reaction is important. There is a narrow conditional window and a narrow kinetic window where the indoleacetaldehyde is present in high relative abundance and has not been oxidatively degraded. Increasing pH or otherwise changing solvent conditions to improve the nucleophilic character of the solvent, or adding an additional reagent as aminating nucleophile, during this conditional window and kinetic window, facilitates reductive amination. Managing the reaction sequence to allow these reaction conditions in a telescoped sequence may be facilitated by real-time reaction monitoring to balance maximizing the amount of the intermediate aldehyde available for reductive amination with minimizing the extent of indole ring destruction from oxidative hydrolysis. Real-time reaction monitoring may be accomplished by a combination of high-performance liquid chromatography ("HPLC") and mass spectrometry ("MS"; the combination of HPLC and MS being called "HPLC-MS"), by proton nuclear magnetic resonance ("1H-NMR") or other suitable real-time analytical techniques. Sampling of the reaction for real-time monitoring may be facilitated by automated sampling during the reaction (Chung, 2017); (Daponte, 2019); (Malig, 2020a); (Malig, 2020b); (Sato, 2021).

Telescoping is the execution of multiple transformations (including quenches and other workup operations) without isolation of intermediates. Telescoped solutions of intermediates can be extracted, filtered (as long as the product remains in the filtrate), and solvent exchanged, but intermediates are held in solution throughout and carried forward to the subsequent transformation. Telescoping reactions together facilitates effective synthesis by carrying out several synthetic transformations and bond-forming steps without work up or purification. Telescoped reactions may be performed as one-pot reactions. Where sufficient monitoring and control are available, telescoped reactions may thus provide efficiencies in terms of chemical waste, time, and simplicity (Hayashi, 2016). Telescoped reactions may also be referred to as cascade, domino or tandem reactions. Approaches to synthesis in which one-pot or telescoped reactions are applied may be effected without isolation of intermediates.

In FIG. 1, Steps 3 and 4 are oxidation of the indole ring, which may be carried out on the amino acid or on the tryptamine, and either before (Steps 4, 5 and 6) or after (Steps 1, 2 and 3) synthesis of the tryptamine. An aryl group may be used to add a hydroxyl group at basic pH, which is less toxic and more cost effective than using thallium. This approach may include C—H functionalization to install an aryl boron as an intermediate before oxidation.

In FIG. 1, the amino acid may be subject to oxidative decarboxylation followed by reductive amination to provide a tryptamine. The solvent or reagent used for reductive amination will determine the N-alkylation pattern of tryptamines that are synthesized using the method of FIG. 1. For example, reductive amination with dimethylamine provides DMT or other unsubstituted tryptamines, or provides psilocin or other ring-substituted tryptamines. Using other alkylated amines may provide other suitable alkylation at the amine group of the resulting tryptamine, whether substituted or not on the indole ring.

Figure 2:
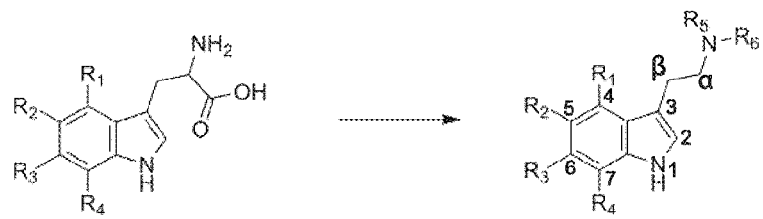
FIG. 2 shows tryptamines that may be synthesized by the method shown in FIG. 1.

FIG. 2 shows tryptamines that may be synthesized in accordance with the method of FIG. 1. In FIG. 2, positions 1, 2, 3, 4, 5, 6, and 7 on the indole ring of tryptamine, and positions a and R on the side chain of tryptamine, are labelled. Where the numbering of tryptamine is referred to herein, the numbering of positions as shown in FIG. 2 is being referenced. Carbons between positions 3 and 4, and between positions 1 and 7, are tertiary sp2 carbons and cannot carry functional groups, so these positions are excluded from the ring numbering of tryptamine used herein.

In FIG. 2, Each of $R_1$ to $R_4$ may be H, and each of $R_5$ and $R_6$ may be methyl, showing conversion of tryptophan to DMT. $R_1$ may be OH, each of $R_2$ to $R_4$ may be H, and $R_5$ and $R_6$ may be methyl, showing conversion of 4-OH-tryptophan to psilocin. Each of $R_1$ to $R_4$ may be any suitable functional group (e.g. —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H, SiR$_3$, etc. wherein R is selected from the group consisting of alkyl, acyl, vinyl, propargyl, phenyl, benzyl, or other suitable groups, and each separate R group may be identical to other R groups or distinct from other R groups).

Tryptamines synthesized in accordance with the method disclosed herein may be alkylated on the terminal amine group with any suitable alkylation pattern. In FIG. 2, each of $R_5$ and $R_6$ may be any suitable H or any suitable alkyl group, and each of $R_5$ and $R_6$ may be the same substituent or may be distinct substituents. For example, alkylation patterns on the terminal amine may include methyl, ethyl, isopropyl, dimethyl, diethyl, diisopropyl, methylethyl, methylisopropyl and ethylisopropyl. Alkylation patterns on the terminal amine group may be cyclic tertiary amine groups, including an unconjugated pyrrolyl group with entirely sp3 orbital configuration on the alkyl amine. Other cyclic tertiary amines, whether conjugated or not, may also be applied to create cyclic tertiary amines (e.g. aromatic pyrrolyl, piperidinyl, pyridinyl, etc.).

Figure 3:
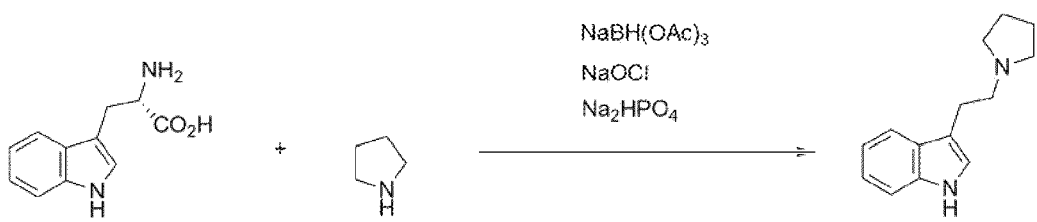
FIG. 3 shows synthesis of a pyrrolidinyl tryptamine from tryptophan.

FIG. 3 shows an example of oxidative decarboxylation followed by reductive amination in which pyrroline is used as a nucleophilic dialkylamine to provide a tryptamine that includes a tertiary amine. The tertiary amine in in FIG. 3 is cyclic as the pyrroline that was used a nucleophile was also cyclic. FIG. 3 shows 3-[2-(pyrrolidin-1-yl)ethyl]-1H-indole, or N,N-tetramethylenetryptamine, which is an unconjugated pyrrolyl tryptamine with entirely sp3 orbital configuration on the alkyl amine group. Other cyclic tertiary amines, whether conjugated or not, may also be applied to create cyclic tertiary amines (e.g. aromatic pyrrolyl groups, piperidinyl groups, pyridinyl groups, etc.).

Tryptophan is decarboxylated with sodium hypochlorite to oxidize the amine to an aldehyde. Sodium phosphate is then added to deprotonate the pyrrolidine to produce a nucleophilic pyrroline, and the aldehyde is reductively aminated with a weak reducing agent.

In FIG. 3, Tryptophan was dissolved in a pH 7 phosphate buffer and reacted with sodium hypochlorite to oxidatively decarboxylate the tryptophan to provide indol-3-ylacetaldehyde (reaction 1 in FIG. 1). After decarboxylation of tryptophan, tryptamine is formed as an intermediate. The sodium hypochlorite oxidizes the amine of tryptamine to move C—N single to C—N* to C═N. Put otherwise, the resulting primary amine from decarboxylation becomes a carbon bonded to N as primary imine. From the primary imine, C═N reacts with nucleophilic OH⁻ to provide a primary alcohol, which in turn oxidizes to an aldehyde. Sodium ascorbate is then added to react with the remaining sodium hypochlorite to prevent excess oxidation and destruction of the indole ring. If the reaction with sodium hypochlorite were allowed to proceed, the indole ring would be cleaved by base. To prevent loss of indole, the solution is pushed into reductive conditions by adjusting the pH to between 7 and 9.

After elimination of excess sodium hypochlorite, methanol was added to dilute the reaction mixture. Pyrrolidine was then added as a solution in water and the pH was adjusted to between 7 and 9 to push the reaction mixture into reductive conditions where pyrrolidine acts as a nucleophile. At this pH range, the indole ring will remain stable and will not be hydrolyzed. At this pH range, which is below the pKa of pyrrolidine (11.3), pyrrolidine will be predominantly deprotonated, increasing its nucleophilicity. The mixture is then treated with sodium triacetoxyhydroborate to reductively aminate the aldehyde with pyrrolidine, resulting in 3-(2-(pyrrolidin-1-yl)ethyl)-1H-indole.

The weak reducing agent sodium triacetoxyhydroborate allows formation of the bond between the alpha carbon and the secondary amine in pyrrolidine without reducing the aldehyde to a primary alcohol, which would occur with stronger reducing agents.

With techniques to monitor abundance of the indoleacetaldehyde, as the tryptophan becomes less abundant and the indoleacetaldehyde becomes more abundant, an amine is added to the reaction mixture and the pH is adjusted to the range where the amine becomes sufficiently nucleophilic to react at the aldehyde, or the reaction conditions are otherwise modified to increase nucleophilicity of the amine. Monitoring of the indoleacetaldehyde abundance may be through HPLC-MS, 1H-NMR or any suitable real-time analytical technique. Sampling of the reaction for real-time monitoring may be facilitated by automated sampling during the reaction.

Figure 11:
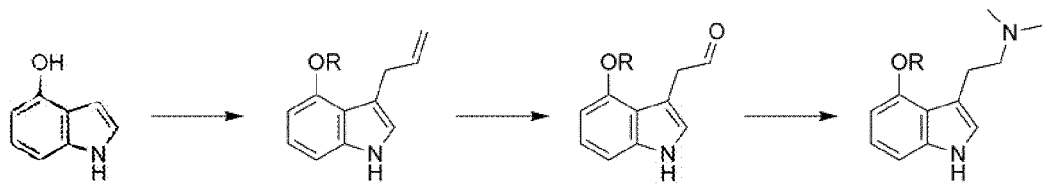
FIG. 11 shows synthesis of a tryptamine from a ring-substituted indole.

The nucleophilic amine may also be provided as the solvent, such as use of pyridine in Examples I, and for the method of FIG. 11, Examples V and XX to XXVI. Any alkyl substitution pattern on the secondary amine may be applied with different nucleophilic amine groups. Propanal may be used as a longer chain surrogate to formaldehyde to provide DiPT and 4-OH-DiPT.

There is no previous report of a direct oxidation of tryptophan that is fed directly to reductive amination of an aldehyde without isolation of intermediates. This telescoped sequence provides efficiencies. The switch from oxidative to reductive with effective coupling of the two reaction conditions is facilitated by close monitoring and control of reaction conditions.

Oxidative decarboxylation of tryptophan has been reported with isolation of an intermediate indoleacetaldehyde (Maresh et al, 2014), (Fawzy, 2016), (Brown, 1952), (Gray, 1959). Previous reaction conditions have been optimized to deliver the resultant indoleacetaldehyde as the sole isolable product. If previous approaches were used prior to reductive amination, then isolation and purification of the indoleacetaldehyde would be required to purge solvent and other potential reaction impurities or reagents before reductive amination. Residual oxidative reagents that facilitate decarboxylation may destroy an alkyl amine and also the borohydride reducing agent. These reactions also require a chemoselective reaction at the amino acid fragment to avoid reaction on the indole ring. This selection process relies on precise and stringent kinetic control set an optimal time frame and provide reaction conditions to allow for only the amino acid, and not the indole ring, to undergo functional group conversion.

The approach shown in FIG. 1 may be carried out with real-time reaction analytics to both visualize the rate and selectivity of the chemical reaction, allowing optimal process decision to be controlled. The process optimization may include timing on transitioning the reaction and the stoichiometry of oxidant. The approach shown in FIG. 1 requires execution of two antagonistic reactions in sequence and in the same reaction vessel. The approach shown in FIG. 1 facilitates seamless execution of step-to-step telescoping between oxidation and reduction amination, which may be carried out in one reaction vessel. Step-to-step telescoping between oxidation and reductive amination may mitigate potential byproducts and uncertainty in the procedure, and may also mitigate potential for error or loss during workup, such as when purifying, when transferring between reaction vessels or at other steps of the procedure.

Reductive amination of indole aldehydes of various substitution and complexity with dialkyl amines have also been reported. (Dethe, 2016) (Shultz, 2011) (Dethe, 2013) and WO2007/017289. In addition to the complications discussed in relation to (Maresh et al, 2014), (Fawzy, 2016), (Brown, 1952) and (Gray, 1959), the amination is further complicated by the need for the reaction to adopt a narrow pH range. The narrow pH range would improve nucleophilicity of the incoming amine while also preventing indole hydrolysis and competing aldol condensation or Mannich coupling at the alkyl aldehyde center. Real-time reaction analytics may facilitate process optimization to identify and maintain conditions, facilitating a challenging manufacturing step of proceeding from allylation under oxidative conditions to alkylation by reductive amination. Monitoring of the indoleacetaldehyde abundance may be through HPLC-MS, 1H-NMR or any suitable real-time analytical technique. Sampling of the reaction for real-time monitoring may be facilitated by automated sampling during the reaction.

Oxidation of the indole ring is shown in steps 3 and 4 of FIG. 1. Direct oxidation is possible with classical Fenton chemistry, which is highly unselective giving mixed oxidation at positions 4, 5, 6 and 7 of the indole ring and poly hydroxylation (*Julia*, 1969). Without selective synthesis by intentionally targeting high production without selectivity, a simple reaction with high conversion but low chemical selectivity could be applied with selective crystallization in continuously stirred tank reactor ("CSTR") and multistage continuous mixed-suspension, mixed-product removal ("MSMPR") techniques could be applied to resolve the compounds. This approach allows foregoing selectivity by separating during different products using purification. This approach has further value as many different hydroxylated tryptamines may each be valuable themselves or as precursors to neurotransmitters (serotonin, melatonin, etc.).

Figure 4:
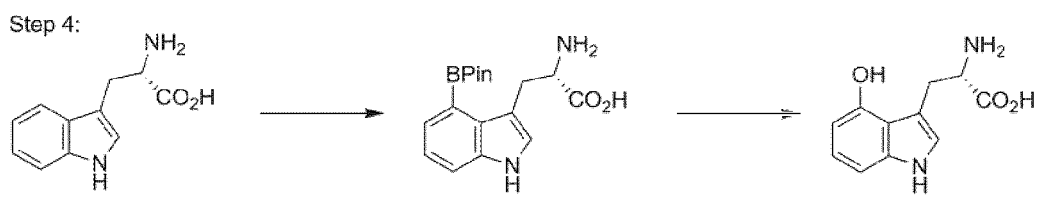
FIG. 4 shows synthesis of a ring-substituted tryptophan analogue from tryptophan.
Figure 5:
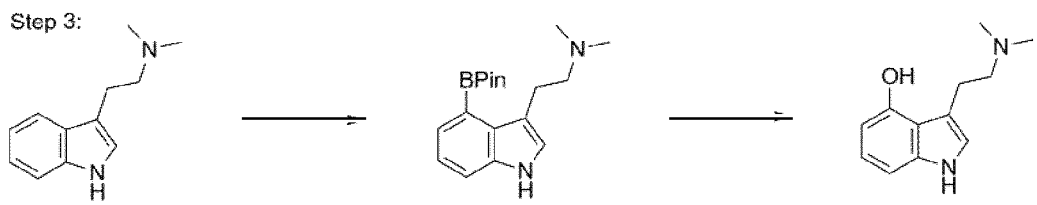
FIG. 5 shows synthesis of a ring-substituted tryptamine from dimethyltryptamine.

FIGS. 4 and 5 show borylation used to add C—H functionalization by installing a pinacolato boron ("BPin") group on the indole ring. A BPin group has the general formula —B(OR)$_2$. An aryl boron or other suitable group may also be added. The BPin, aryl boron or other group is then oxidatively hydrolyzed to a hydroxyl group on the indole ring. In FIG. 4, this approach is applied to tryptophan (Step 4 in the series of Steps 4 to 6 shown in FIG. 1). In FIG. 5, this approach is applied to DMT (Step 3 in the series of Steps 1 to 3 shown in FIG. 1).

The two steps of each of FIGS. 3 and 4 (i.e. first borylation or other functionalization, then oxidation) may be telescoped without isolation of any intermediates. When applied to DMT rather than tryptophan, the tertiary amine provides as a directing group to position 4 on the indole ring and greater regioselectivity in the borylation than with tryptophan. There is no previous report of functionalization on the indole ring that is fed directly to oxidation of the functionalized tryptophan, which is in turn fed directly to reductive amination of the indoleacetaldehyde, without isolation of intermediates. This telescoped sequence provides efficiencies. To carry out the needed switch from oxidative to reductive with effective coupling of the two reaction conditions requires close monitoring and control of reaction conditions. Monitoring of the indoleacetaldehyde abundance may be through HPLC-MS, 1H-NMR or any suitable real-time analytical technique. Sampling of the reaction for real-time monitoring may be facilitated by automated sampling during the reaction. Control of reaction conditions may be effected by increasing the pH of the solvent, by adding amines or both.

Figure 9:
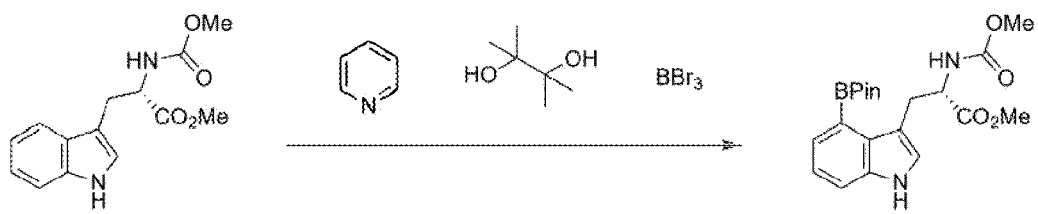
FIG. 9 shows synthesis of a ring-substituted carbamate analogue of a tryptamine.

FIGS. 3 and 4 may include application of a carbamate protecting group on the amino nitrogen, an example of which is provided in Example III (FIG. 9). With the correct protecting groups this approach may select for 4-substituted tryptamines as an abundant product. Chelation control may be responsible for this result as suggested by earlier work on other systems (Lv, 2019). Sequential reaction (borylation followed by hydrolysis) facilitates hydroxylation at C-4 of indole. There are currently no published reports of this approach reaction access compound relating to tryptamines.

Applying chelation control to functionalize the indole CH at C-4 is reported with a route employing thallium (Somei, 1998) to synthesize psilocin. Thallium is highly toxic and cannot be used in GMP manufacture of active pharmaceutical ingredients.

Figure 6:
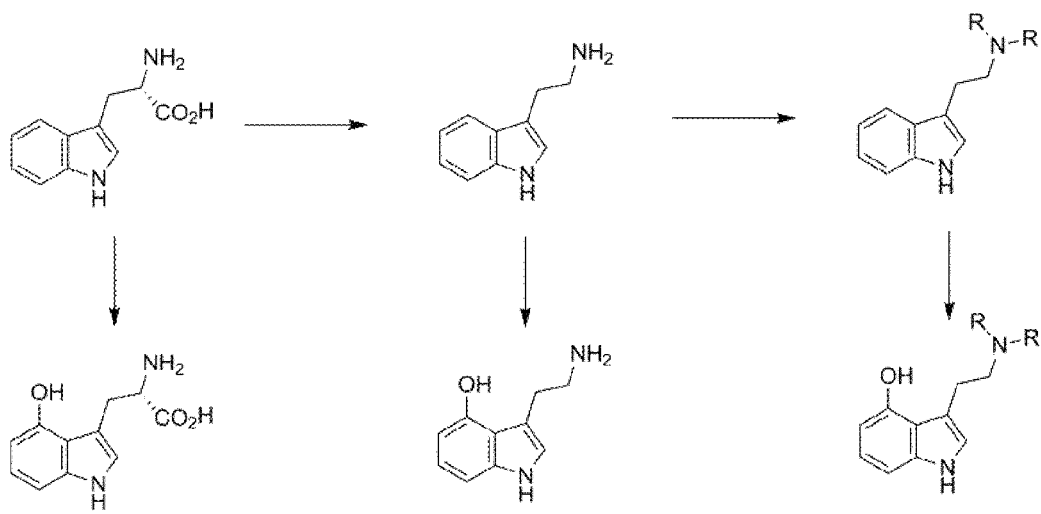
FIG. 6 shows synthesis of ring-substituted tryptophan analogues and tryptamines from tryptophan and ring substituted tryptamines from unsubstituted tryptamines.

FIG. 6 shows decarboxylation, for example by benzaldehyde in MeOH at high temperature, which efficiently yields tryptamine, or any suitable method. The tryptamine may be alkylated using reductive amination or any suitable method. Tryptophan, tryptamine or alkylated tryptamines were separately treated with FeSO4 and hydrogen peroxide to oxidize the indole ring. By selecting tryptophan, tryptamine or alkylated tryptamine as precursors, a ring-substituted tryptophan analogue, a ring-substituted tryptamine or a ring-substituted alkylated tryptamine may be prepared, each of which presented as a mixture of mono and polyhydroxylated materials after 2 to 3 hours (as shown in a generalized sense in FIG. 8).

Direct oxidation at the aromatic center by the approach shown in FIG. 6 is facilitated where hydrogen peroxide is added gradually over time. Single administration and syringe pump addition over 20 min were each evaluated. The overall reaction of indole starting materials was higher when adding hydrogen peroxide gradually. In some cases, a conversion of about 60 to 80% was observed by adding hydrogen peroxide over 20 minutes compared with about 10 to 15% conversion when adding the hydrogen peroxide in a single bolus. This is consistent with a significant degree of unproductive peroxide decomposing and is common to this class of Fenton chemistry.

In some cases, shortly after addition of hydrogen peroxide, the 4-OH isomer was observed as the major regioisomer. After 20 to 30 minutes, both the 5- and 6-substituted products began to appear. At longer reaction times (2 to 3 hours) the desired 4-OH products began to be consumed to give polyhydroxylated byproducts. Of the three aromatic precursors, the N,N dialkylated tryptamine was found in the highest relative abundance, and the N,N dialkylated compound did not show any 5-, or 6 hydroxylated products at the time point assessed. This selectivity may indicate a favorable N—Fe interaction at play directing the reaction toward the proximal C—H relative to the coordination site, in this case, the 4 position on the indole ring, using the numbering of tryptamine.

Application of coordinate iron complexes, such as the White-Chen catalyst, effectively suppress polyhydroxylation. This early study proved that by identifying an appropriate ligand system for the iron center it should be possible to select for only monohydroxylated species. Preferential continuous crystallization could then be applied to separate the position 4, position 5 and position 6 aromatic isomers.

Figure 7:
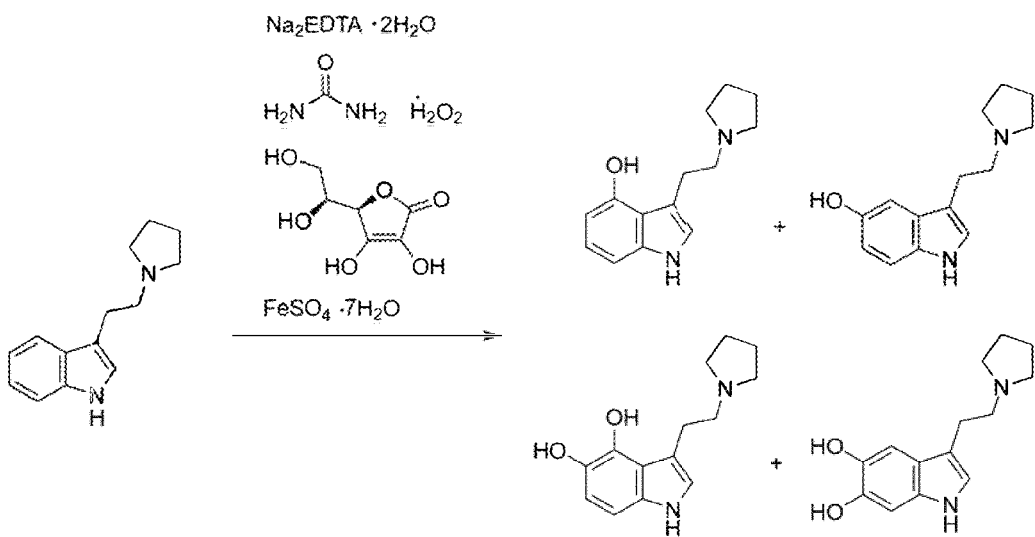
FIG. 7 shows synthesis of multiple ring-substituted pyrrolidinyl tryptamines from pyrrolidinyl tryptamine.

FIG. 7 shows synthesis of multiple ring-substituted pyrrolidinyl tryptamines from pyrrolidinyl tryptamine. The ring oxidation may be undertaken by classical Fenton chemistry, which is highly unselective giving mixed directed oxidation at positions 4, 5 and 6, and also polyhydroxylation.

Figure 8:
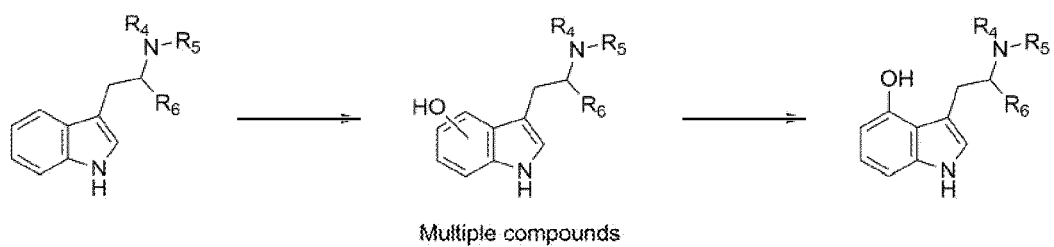
FIG. 8 shows tryptamines that may be synthesized in accordance with the method of FIG. 7.

FIG. 8 shows tryptamines that may be synthesized in accordance with the method of FIG. 7, and applied as Step 3 of FIG. 1. $R_4$ and $R_5$ may be each be methyl, and $R_6$ may be H, showing conversion of tryptophan to psilocin. $R_4$ and $R_5$ may be any suitable alkyl group, including a cycloalkyl group or other ring structure. $R_6$ may be any suitable functional group (e.g. —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H, SiR$_3$, etc. wherein R is selected from the group consisting of alkyl, acyl, vinyl, propargyl, phenyl, benzyl, or other suitable groups, and each separate R group may be identical to other R groups or distinct from other R groups). Where a hydroxyl group will be added to the indole ring, $R_6$ is H, alkyl or another low-reactivity group to preserve reactivity on the indole ring rather than substitution at $R_6$. From among the range of substitution sites on the indole ring, the 4-substituted tryptamine may be selectively separated and isolated through application of continuous crystallization, fractional crystallization or other suitable isolation techniques. Tryptamines substituted on other portions of the indole ring may also be selectively separated and isolated.

FIG. 9 shows synthesis of a ring-substituted carbamate analogue of tryptophan. Methyl (ethoxycarbonyl)-L-tryptophanate is reacted with boron tribromide, then quenched with pyridine and pinacol to provide methyl (S)-2-((ethoxycarbonyl)amino)-3-(4-(4,4,5,5-tetramethyl-1,3,2-dioxaborolan-2-yl)-1H-indol-3-yl)propanoate. The method of FIG. 9 may be applied as step 3 in the method of FIG. 1, and is an example of directed oxidation being applied to synthesizing tryptamines.

Figure 10:
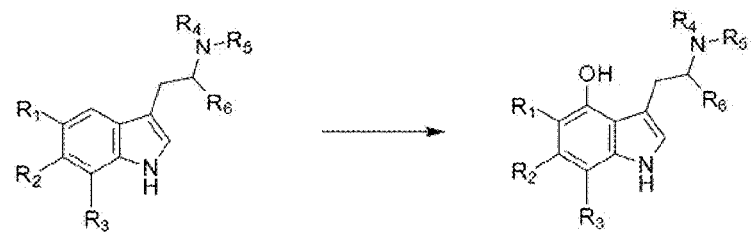
FIG. 10 shows tryptamines that may be synthesized in accordance with the method of FIG. 9.

FIG. 10 shows tryptamines that may be synthesized in accordance with the method of FIG. 9, or step 3 of FIG. 1. Each of $R_1$ to $R_3$ may be H, each of $R_4$ and $R_5$ may be methyl, showing conversion of tryptamine to psilocin. Each of $R_1$ to $R_3$ and $R_6$ may be any suitable functional group (e.g. —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H, SiR$_3$, etc. wherein R is selected from the group consisting of alkyl, acyl, vinyl, propargyl, phenyl, benzyl, or other suitable groups, and each separate R group may be identical to other R groups or distinct from other R groups). Each of $R_4$ and $R_5$ may be any suitable alkyl group, including a cycloalkyl group or other ring structure. Where a hydroxyl group will be added to the indole ring, $R_6$ is H, alkyl or another low-reactivity group to preserve reactivity on the indole ring rather than substitution at $R_6$.

FIG. 11 shows synthesis of tryptamines from substituted indole by allylating the indole ring with an allyl group and substituting a protecting group to the 4-hydroxyl (step 1), oxidizing to an indoleacetaldehyde (step 2), then reductive amination to provide a tryptamine (step 3). Nucleophilic substitution may be effected by solvent molecules.

The reaction scheme shown in FIG. 11 leverages synthetic manipulations on an appropriately protected hydroxy-indole core (e.g. acetylated, phosphorylated, silylated, halogenated, etc.). In this approach, aromatic manipulations would be carried out using 4-hydroxy indole as a starting point. While 4-hydroxy indole is a stable precursor, 4-hydroxy indole will preferentially react via nucleophilic aromatic substitution at the 2-position, opening up numerous synthetic pathways based on classical Friedel-Crafts acylation and alkylation chemistry, such as using oxalyl chloride.

The reaction scheme shown in FIG. 11 eliminates the need to oxidizing or otherwise derivatizing the tryptophan indole ring or the tryptamine ring indole ring by starting with 4-hydroxindole. 4-hydroxindole is an inexpensive commodity chemical. Allylation of the substituted indole is followed by oxidative scission of the resulting alkene to provide an aldehyde and reductive amination of the aldehyde to provide an amine. The hydroxyl group at the 4-position of the resulting tryptamine may be substituted for another functional group (e.g. —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H, SiR$_3$, etc. wherein R is selected from the group consisting of alkyl, acyl, vinyl, propargyl, phenyl, benzyl, or other suitable groups, and each separate R group may be identical to other R groups or distinct from other R groups). Substituting hydroxyl for another functional group may be carried out using any suitable nucleophilic, electrophilic, oxidative, reductive or other substitution technique.

The method of FIG. 11 may include direct formation of aldehyde, telescoped into the reductive amination to install the dimethylamine (combine step 2 and 3 in FIG. 11). Monitoring of the indoleacetaldehyde abundance may be through HPLC-MS, 1H-NMR or any suitable real-time analytical technique. Sampling of the reaction for real-time monitoring may be facilitated by automated sampling during the reaction. Reductive amination of 4-oxo-indoleacetaldehydes (step 3) has not been previously reported, whether telescoped or not.

While the methods of FIGS. 1 to 10 also provide an aldehyde as an intermediate, the steps leading to the aldehyde in FIGS. 1 to 10 are different than those in the method shown in FIG. 11. The steps from the aldehyde to the amine are similar in both FIGS. 1 to 10 and in FIG. 11. In each case, there are different oxidants, and in each case timing matters to ensure that there is a large amount of aldehyde but without loss of indole to oxidative cleavage. This approach may also be applied to DMT or other tryptamines that have no substitution on the indole ring.

Figure 14:
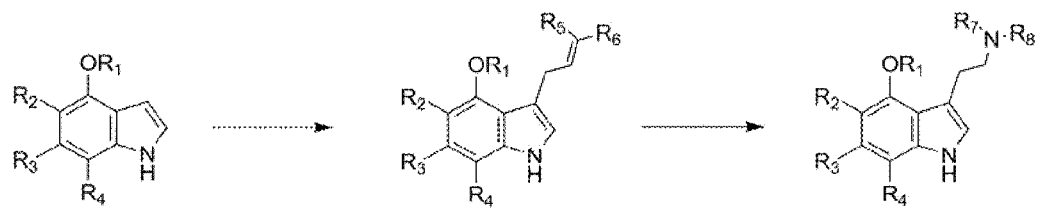
FIG. 14 shows tryptamines that may be synthesized in accordance with the method of FIGS. 12 and 13.

The approach shown in FIG. 11 could be used for other alkylation patterns or other functional groups, similarly to the approach of FIGS. 1 to 10. FIG. 14 illustrates a variety of ring-substituted tryptamines that may be prepared using the method of FIG. 11.

Allylation of a C-4 hydroxylated indole or similarly 4-substituted indole with functionality that can be readily reconverted to psilocin has not been previously demonstrated. The added electron density and possible steric occlusion near the C-3 position resulting from functionality at C-4 may drive allyl addition to favor the indole nitrogen over the nucleophilic, enamine-like center located at C-3. The method of FIG. 11 provides a highly regioselective allylation using a Tsuji-Trost like functionalization, which may result from a Pd-allyl cationic intermediate (Kimura, 2005).

Figure 12:
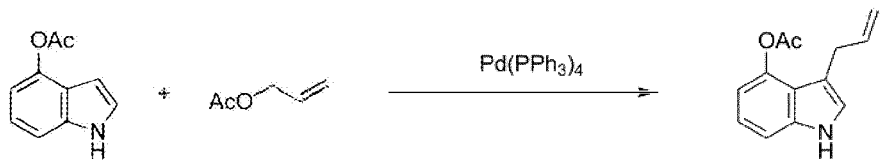
FIG. 12 shows synthesis of 4-acetyl-2-allylindole (or 5-acetyl-3-allylindole counting from the indole nitrogen as position 1), FIG. 13 synthesis of a constrained pyrrolidine tryptamine from 4-acetyl-2-allylindole (or 5-acetyl-3-allylindole counting from the indole nitrogen as position 1)

FIG. 12 is an example of the process shown in FIG. 11. Acetyl-indole may be reacted with allyl acetate with a palladium catalyst to provide 4-acetyl-2-allylindole or 5-acetyl-3-allylindole, using the numbering of tryptamine and counting from the indole nitrogen as position 1 as shown in FIG. 2.

Figure 13:
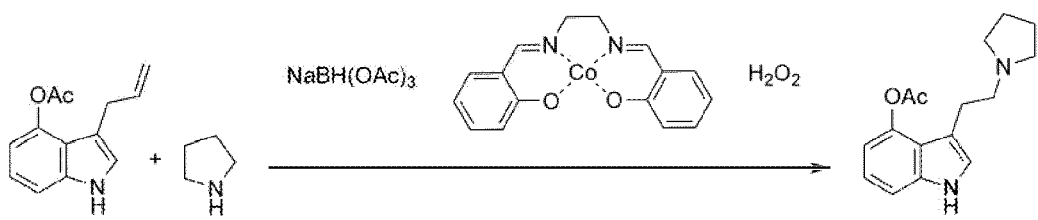

FIG. 13 shows 4-acetyl-2-allylindole reacted with salcomine (cobalt-salen) in the presence of peroxide, reducing the allyl group to an aldehyde 4-acetyl-2-ethal-indole (not shown). The aldehyde is combined with pyrrolidine and treated with sodium triacetoxyhydroborate to reductively aminate the aldehyde with pyrrolidine, resulting in the 4-acetylated analogue of 3-(2-(pyrrolidin-1-yl)ethyl)-1H-indole.

Conversion of an indole with C-3 alkene to an aldehyde has been reported in (Brown, 1952) and (Chen, 2017), each of which include a two-step sequence. First, dihydroxylation using OsO$_4$ or similar high valence transition state metal catalyst. This approach applies a metalperoxo-catalyzed transfer, which has been demonstrated on simple substrates in (Mi, 2015) and (Tamami, 2011). The method of FIG. 13 may be applied with real-time reaction progress profiling to control reaction conditions, target certain chemicals and minimize production of byproducts. Concentrations, temperature and the addition rate of the hydrogen peroxide may be precisely controlled. Precise control mitigates overoxidation of the aldehyde to subsequent carboxylic acid or derivatization of the indole ring.

Analogous in some respects to the approach of FIGS. 1 to 5, the methods of FIGS. 11 to 13 include conversion of a terminal alkene to an amine by reductive amination of an intermediate aldehyde without any requirement for isolation and workup between a ring-substituted tryptophan analogue and a ring-substituted tryptamine. A telescoped sequence including oxidative functional group rearrangement followed by C—N bond formation by reductive amination involves sequential application of two antagonistic and mutually exclusive reaction conditions. Managing the sequence to allow these reaction conditions in a telescoped sequence may be facilitated by real-time reaction sampling and monitoring to balance maximizing the amount of the intermediate aldehyde available for reductive amination with minimizing the extent of indole ring destruction from oxidative hydrolysis.

Reactions similar to step 2 of FIG. 11 have not been previously demonstrated for compounds functionalized with oxygen, halide, other electron-rich substituents, or other substituents on the indole ring (e.g. —OH, —OR, —NH$_2$, —NHR, —NR$_2$, —NHCOR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H, SiR$_3$, etc. wherein R is selected from the group consisting of alkyl, acyl, vinyl, propargyl, phenyl, benzyl, or other suitable groups, and each separate R group may be identical to other R groups or distinct from other R groups).

FIG. 14 shows tryptamines that may be synthesized in accordance with the method of FIGS. 12 and 13. $R_1$ may be H, each of $R_2$ to $R_4$ may be H, each of $R_5$ and $R_6$ may be H and each of $R_7$ and $R_8$ may be methyl, showing conversion of 4-hydroxyindole to psilocin. $R_1$ may be any acyl or silyl group. Each of $R_2$ to $R_4$ may be any suitable functional group (e.g. —OH, —OR, —NH$_2$, —NHR, —NR$_2$, —NH-COR, —R$_3$N$^+$, —NO$_2$, —CN, —N$_3$, —COR, —CO$_2$H, —CO$_2$R, —CHO, —RCHO, —R, —B(OR)$_2$, —B(F$_3$)$^-$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H, SiR$_3$, etc. wherein R is selected from the group consisting of alkyl, acyl, vinyl, propargyl, phenyl, benzyl, or other suitable groups, and each separate R group may be identical to other R groups or distinct from other R groups). Each of $R_5$ and $R_6$ may be H or any suitable alkyl. Each of $R_7$ and $R_8$ may be any suitable alkyl.

Figure 15:
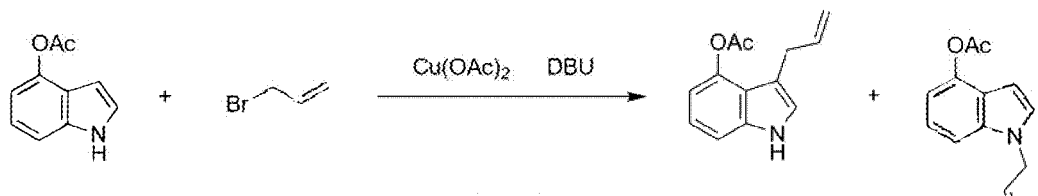
FIG. 15 shows synthesis of 4-acetyl-2-allylindole and 4-acetyl-N-allylindole from 4-acetylindole.

FIG. 15 shows synthesis of 4-acetyl-2-allylindole and 4-acetyl-N-allylindole from 4-acetylindole.

Figure 16:
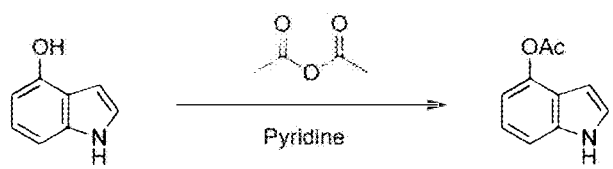
FIG. 16 shows synthesis of 1H-indol-4-yl acetate from 4-hydroxyindole.
Figure 17:
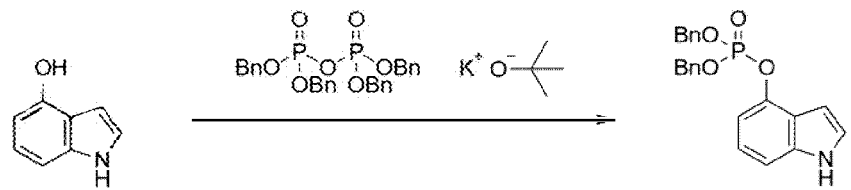
FIG. 17 shows synthesis of dibenzyl (1H-indol-4-yl) phosphate from 4-hydroxyindole.

4-hydroxyindole may be used as a starting point for synthesizing other 4-substituted indole compounds, such as acetylated or dibenzylphosphorylated indole compounds, as shown in FIGS. 16 and 17.

FIG. 16 shows synthesis of 1H-indol-4-yl acetate from 4-hydroxyindole. Examples of this process are shown in Examples VII, XIII and IX.

FIG. 17 shows synthesis of dibenzyl (1H-indol-4-yl) phosphate from 4-hydroxyindole. Dibenzyl (1H-indol-4-yl) phosphate has not been previously reported and may be a valuable precursor for other compounds, as illustrated by FIG. 19.

Indole compounds, including 4-substituted indole compounds, such as 4-acetyl or 4-dibenzyl phosphate indole compounds, may be allylated through catalysis by palladium as shown in FIG. 12. Two examples are shown in FIGS. 18 and 19.

Figure 18:
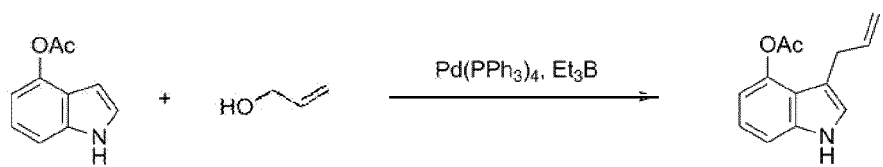
FIG. 18 shows synthesis of 3-allyl-1H-indol-4-yl acetate from 4-acetylindole.

FIG. 18 shows synthesis of 3-allyl-1H-indol-4-yl acetate from 4-acetylindole. 3-allyl-1H-indol-4-yl acetate may provide a reagent for synthesis of 4-substituted diols, tryptamines or other compounds. Example XI and Example XII provide illustrations of application of this method.

Figure 19:
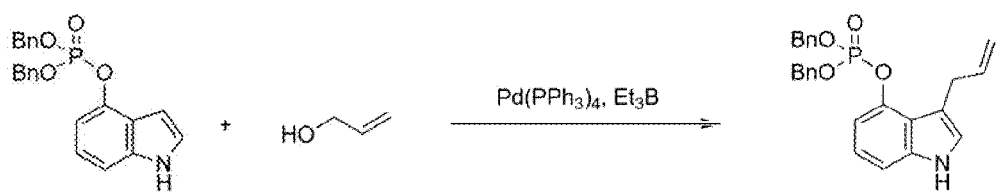
FIG. 19 shows synthesis of 3-allyl-1H-indol-4-yl dibenzyl phosphate from dibenzyl (1H-indol-4-yl) phosphate.

FIG. 19 shows synthesis of 3-allyl-1H-indol-4-yl dibenzyl phosphate from dibenzyl (1H-indol-4-yl) phosphate. As exemplified by Example XIII, FIG. 19 shows a method that facilitates direct allylation on a pseudo halide, —PO$_2$(OR)$_2$.

Figure 20:
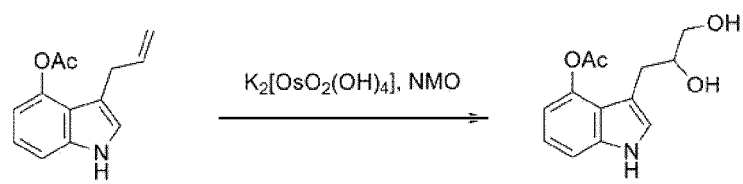
FIG. 20 shows synthesis of 3-(2,3-dihydroxypropyl)-1H-indol-4-yl acetate from 3-allyl-1H-indol-4-yl acetate.

FIG. 20 shows synthesis of 3-(2,3-dihydroxypropyl)-1H-indol-4-yl acetate from 3-allyl-1H-indol-4-yl acetate. 3-(2, 3-dihydroxypropyl)-1H-indol-4-yl acetate may provide a precursor that may facilitate synthesis of 4-substituted tryptamines, as exemplified in Examples XIV, XV and XVI.

Figure 21:
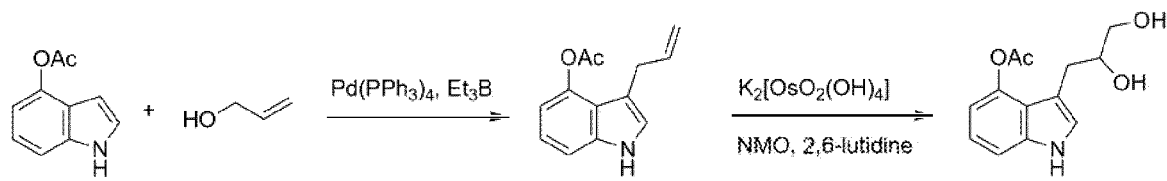
FIG. 21 shows synthesis of 3-(2,3-dihydroxypropyl)-1H-indol-4-yl acetate from 1H-indol-4-yl acetate in a telescoped reaction.

FIG. 21 shows synthesis of 3-(2,3-dihydroxypropyl)-1H-indol-4-yl acetate from 1H-indol-4-yl acetate in a telescoped reaction without isolation of any intermediates. Allylation of 4-acetyl-indole and oxidation of the 3-allyl-1H-indol-4-yl acetate together without isolation of any intermediates may facilitate synthesis of 4-substituted tryptamines or provide compounds with therapeutic or other applications without reductive amination to a tryptamine. Application of the method of FIG. 21 is illustrated by Examples XVII, XVIII and XIX.

Figure 22:
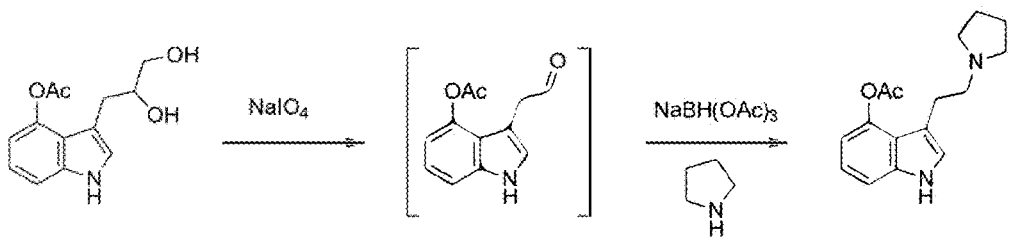
FIG. 22 shows synthesis of 3-(2-(pyrrolidin-1-yl)ethyl)-1H-indol-4-yl acetate from 3-(2,3-dihydroxypropyl)-1H-indol-4-yl acetate in a telescoped reaction.

FIG. 22 shows synthesis of 3-(2-(pyrrolidin-1-yl)ethyl)-1H-indol-4-yl acetate from 3-(2,3-dihydroxypropyl)-1H-indol-4-yl acetate in a telescoped reaction without isolation of any intermediates. A weak reducing agent, NaBH(OAc)$_3$, is used to reduce the 3-allyl-1H-indol-4-yl acetate to 3-(2-(pyrrolidin-1-yl)ethyl)-1H-indol-4-yl acetate rather than to 3-(2-(pyrrolidin-1-yl)ethyl)-1H-indol-4-ol. Application of the method of FIG. 21 is illustrated by Examples XX, XXI and XXII.

Figure 23:
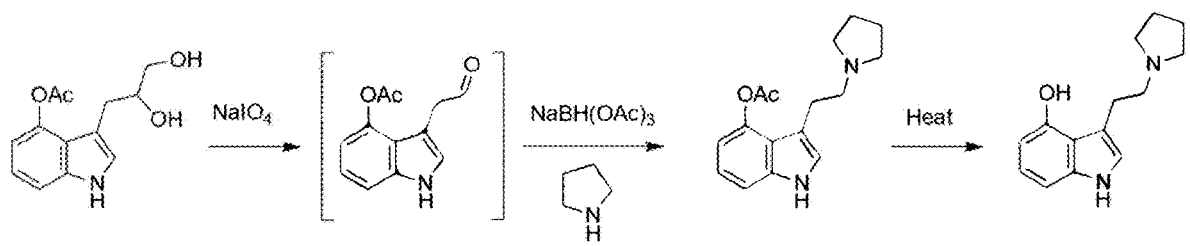
FIG. 23 shows synthesis of 3-(2-(pyrrolidin-1-yl)ethyl)-1H-indol-4-ol from 3-(2,3-dihydroxypropyl)-1H-indol-4-yl acetate in a telescoped reaction.

FIG. 23 shows synthesis of 3-(2-(pyrrolidin-1-yl)ethyl)-1H-indol-4-ol from 3-(2,3-dihydroxypropyl)-1H-indol-4-yl acetate in a telescoped reaction without isolation of any intermediates. Heat is used to complete a three-step telescoped sequence beyond the 3-(2-(pyrrolidin-1-yl)ethyl)-1H-indol-4-acetate generated in FIG. 22. FIG. 23, which is exemplified by Example XXIII, shows oxidizing an indole propyl diol to provide a ring-substituted indoleacetaldehyde, reductively aminating the ring-substituted indoleacetaldehyde to provide an acetylated tryptamine, and reducing the acetylated tryptamine to provide a hydroxylated tryptamine. The tryptamines may be alkylated on the terminal amine group with any suitable alkylation pattern. Alkylation patterns on the terminal amine may include methyl, ethyl, isopropyl, dimethylamine diethyl, diisopropyl, methylethyl, methylisopropyl and ethylisopropyl. Alkylation patterns on the terminal amine group may be cyclic tertiary amine groups, including an unconjugated pyrrolyl group with entirely sp3 orbital configuration on the alkyl amine. Other cyclic tertiary amines, whether conjugated or not, may also be applied to create cyclic tertiary amines (e.g. aromatic pyrrolyl, piperidinyl, pyridinyl, etc.)

Figure 24:
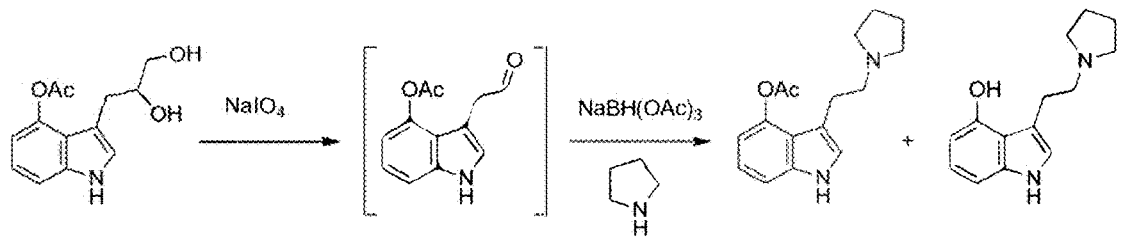
FIG. 24 shows synthesis of a mixture of 3-(2-(pyrrolidin-1-yl)ethyl)-1H-indol-4-yl acetate and 3-(2-(pyrrolidin-1-yl)ethyl)-1H-indol-4-ol from 3-(2,3-dihydroxypropyl)-1H-indol-4-yl acetate in a telescoped reaction.

FIG. 24 shows synthesis of a mixture of 3-(2-(pyrrolidin-1-yl)ethyl)-1H-indol-4-yl acetate and 3-(2-(pyrrolidin-1-yl) ethyl)-1H-indol-4-ol from 3-(2,3-dihydroxypropyl)-1H-indol-4-yl acetate in a telescoped reaction without isolation of any intermediates. As with FIG. 26, a variety of alkylation patterns may be applied to the method of FIG. 24, which is exemplified by Example XXIV.

Figure 25:
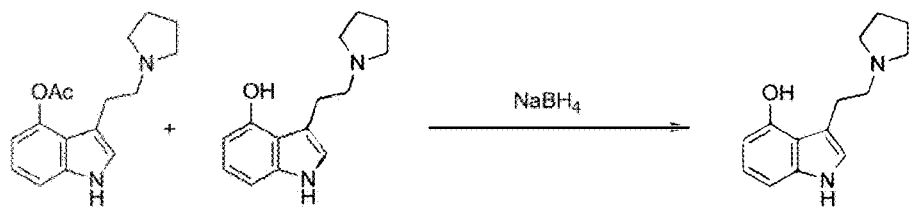
FIG. 25 shows synthesis of 3-(2-(pyrrolidin-1-yl)ethyl)-1H-indol-4-ol from a mixture of 3-(2-(pyrrolidin-1-yl)ethyl)-1H-indol-4-yl acetate and 3-(2-(pyrrolidin-1-yl)ethyl)-1H-indol-4-ol.

FIG. 25 shows synthesis of 3-(2-(pyrrolidin-1-yl)ethyl)-1H-indol-4-ol from a mixture of 3-(2-(pyrrolidin-1-yl) ethyl)-1H-indol-4-yl acetate and 3-(2-(pyrrolidin-1-yl) ethyl)-1H-indol-4-ol. A stronger reducing agent than NaBH (OAc)$_3$, NaBH$_4$, is used to complete a three-step telescoped sequence without isolation of any intermediates (in contrast with application of heat in FIG. 23). As with FIG. 26, a variety of alkylation patterns may be applied to the method of FIG. 25, which is exemplified by Example XXV.

Figure 26:
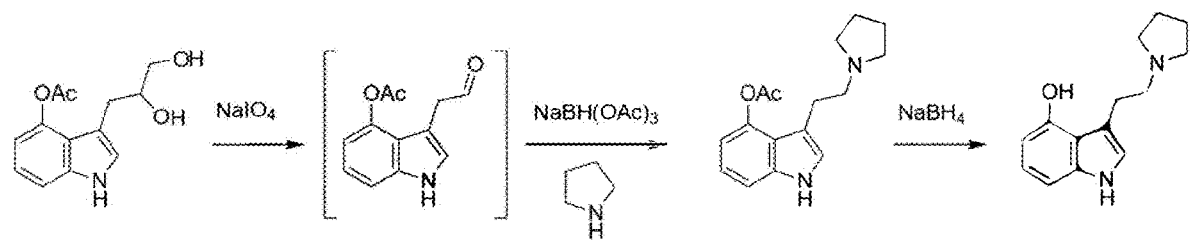
FIG. 26 shows synthesis of 3-(2-(pyrrolidin-1-yl)ethyl)-1H-indol-4-ol from 3-(2,3-dihydroxypropyl)-1H-indol-4-yl acetate in a telescoped reaction.

FIG. 26 shows synthesis of 3-(2-(pyrrolidin-1-yl)ethyl)-1H-indol-4-ol from 3-(2,3-dihydroxypropyl)-1H-indol-4-yl acetate in a telescoped reaction incorporating the reactions shown in both FIG. 24 and FIG. 25 without isolation of any intermediates. A stronger reducing agent than NaBH(OAc)$_3$, NaBH$_4$, is used to complete a three-step telescoped sequence without isolation of any intermediates (in contrast with application of heat in FIG. 23). FIG. 26, which is exemplified by Example XXVI, shows oxidizing an indole propyl diol to provide a ring-substituted indoleacetaldehyde, reductively aminating the ring-substituted indoleacetaldehyde to provide an acetylated tryptamine, and reducing the acetylated tryptamine to provide a hydroxylated tryptamine. The tryptamines may be alkylated on the terminal amine group with any suitable alkylation pattern. Alkylation patterns on the terminal amine may include methyl, ethyl, isopropyl, dimethylamine diethyl, diisopropyl, methylethyl, methylisopropyl and ethylisopropyl. Alkylation patterns on the terminal amine group may be cyclic tertiary amine groups, including an unconjugated pyrrolyl group with entirely sp3 orbital configuration on the alkyl amine. Other cyclic tertiary amines, whether conjugated or not, may also be applied to create cyclic tertiary amines (e.g. aromatic pyrrolyl, piperidinyl, pyridinyl, etc.).

Figure 27:
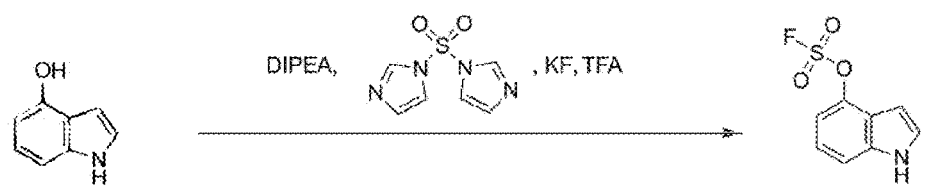
FIG. 27 shows synthesis of 1H-indol-4-yl sulfurofluoridate from 4-hydroxyindole.

FIG. 27 shows synthesis of 1H-indol-4-yl sulfurofluoridate from 4-hydroxyindole. Example XXVII illustrates conditions under which the —$SO_3F$ group is substituted for the hydroxyl group at the 4-position of 4-hydroxyindole. 1,1,sulfonyldiimidazole was reacted with the 4-hydroxyindole to produce 1H-indol-4-yl sulfurofluoridate.

Figure 28:
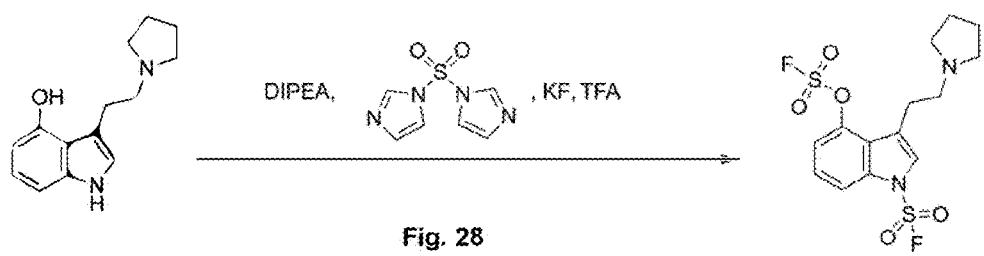
FIG. 28 shows synthesis of 1-(fluorosulfonyl)-3-(2-(pyrrolidin-1-yl)ethyl)-1H-indol-4-yl sulfurofluoridate from 3-(2-(pyrrolidin-1-yl)ethyl)-1H-indol-4-ol.

FIG. 28 shows synthesis of 1-(fluorosulfonyl)-3-(2-(pyrrolidin-1-yl)ethyl)-1H-indol-4-yl sulfurofluoridate from 3-(2-(pyrrolidin-1-yl)ethyl)-1H-indol-4-ol. Example XXVIII illustrates conditions under which regioselectivity for positions 1 and 4 by the —$SO_3F$ group when added to 3-(2-(pyrrolidin-1-yl)ethyl)-1H-indol-4-ol. 1,1,sulfonyldiimidazole was reacted with 3-(2-(pyrrolidin-1-yl)ethyl)-1H-indol-4-ol.

Figure 29:
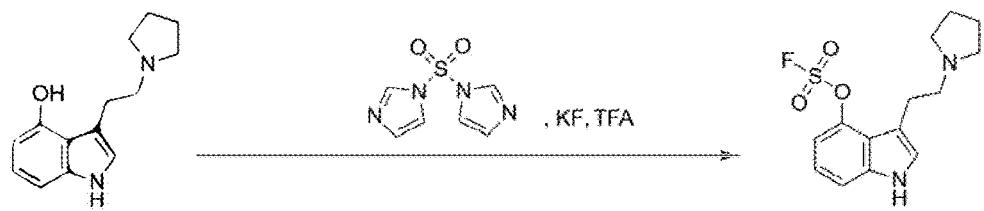
FIG. 29 shows synthesis of 3-(2-(pyrrolidin-1-yl)ethyl)-1H-indol-4-yl sulfurofluoridate from 3-(2-(pyrrolidin-1-yl)ethyl)-1H-indol-4-ol.

FIG. 29 shows synthesis of 3-(2-(pyrrolidin-1-yl)ethyl)-1H-indol-4-yl sulfurofluoridate from 3-(2-(pyrrolidin-1-yl) ethyl)-1H-indol-4-ol. Example XXIX illustrates conditions under which regioselectivity for position 4 by the —$SO_3F$ group is facilitated.

Figure 30:
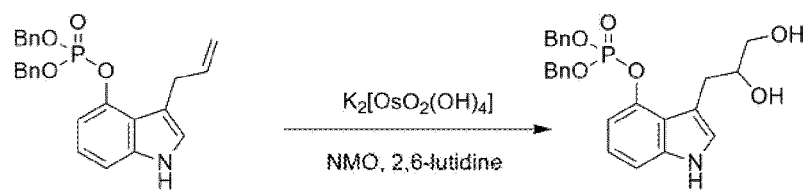
FIG. 30 shows synthesis of dibenzyl (3-(2,3-dihydroxypropyl)-1H-indol-4-yl) phosphate from 3-allyl-1H-indol-4-yl dibenzyl phosphate.

FIG. 30 shows synthesis of dibenzyl (3-(2,3-dihydroxypropyl)-1H-indol-4-yl) phosphate from 3-allyl-1H-indol-4-yl dibenzyl phosphate. Example XXX illustrates oxidation of dibenzyl (3-(2,3-dihydroxypropyl)-1H-indol-4-yl) phosphate. Phosphate surrogate may also provide a direct route to psilocybin or other 4-substituted tryptamines.

Figure 31:
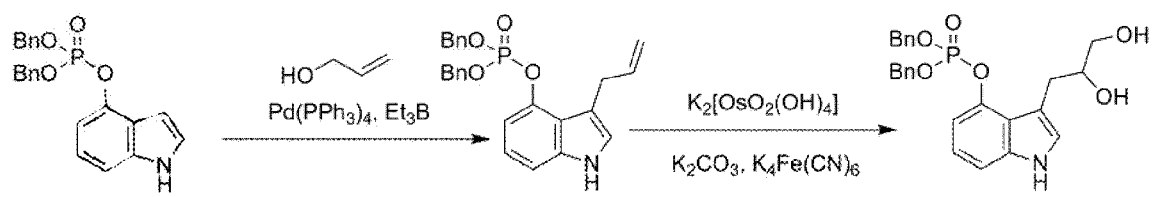
FIG. 31 shows synthesis of dibenzyl (3-(2,3-dihydroxypropyl)-1H-indol-4-yl) phosphate from dibenzyl (1H-indol-4-yl) phosphate in a telescoped reaction.

FIG. 31 shows synthesis of dibenzyl (3-(2,3-dihydroxypropyl)-1H-indol-4-yl) phosphate from dibenzyl (1H-indol-4-yl) phosphate in a telescoped reaction without isolation of any intermediates. FIG. 31 shows telescoped allylation and hydroxylation on a phosphate-substituted indole compound. Example XXXI illustrates compatibility of the methods disclosed herein with a variety of substrates to which the method may be telescoped to exclude workup or isolation of any intermediates. Oxidation of the dibenzyl (3-(2,3-dihydroxypropyl)-1H-indol-4-yl) and reductive amination of the resulting aldehyde may follow as illustrated elsewhere in this specification.

Example I

The method shown in FIG. 3 was carried out. The reagents were mixed into a total volume of 427 mL, including 250 mL of water and 100 mL of methanol, with a reaction molarity of 11.7 mmolar at a temperature of 25° C. Details of the reagents are shown in Table 1A and Table 1B. Details of the products are shown in Table 1C and Table 1D

TABLE 1A

Physical Properties of Reagents

| Reagent | Formula | MM (g/mol) |
|---|---|---|
| L-tryptophan | $C_{11}H_{12}N_2O_2$ | 204.23 |
| pyrrolidine | $C_4H_9N$ | 71.12 |
| sodium triacetoxyhydroborate | $C_6H_{10}BNaO_6$ | 211.94 |
| sodium hypochlorite | NaClO | 74.44 |
| sodium phosphate, dibasic | $HNa_2O_4P$ | 141.96 |

TABLE 1B

Relative Amounts of Reagents and Solvents

| Reagent | Eq | M (g) | mmol | Notes |
|---|---|---|---|---|
| L-tryptophan | 1.0 | 1.02 | 5.00 | N/A |
| pyrrolidine | 2.3 | 2.04 | 11.50 | 2 mL vol 1 g/mL density 40% Wt |
| sodium triacetoxyhydroborate | 2.0 | 2.12 | 10.00 | N/A |
| sodium hypochlorite | 1.5 | 0.558 | 7.50 | 0.1 molar 75.0 mL 1.206 g/mL |
| sodium phosphate, dibasic | 2.5 | 1.77 | 12.50 | N/A |

TABLE 1C

Physical Properties of Products

| Product | Formula | MM (g/mol) |
|---|---|---|
| 3-(2-(pyrrolidin-1-yl)ethyl)-1H-indole | $C_{14}H_{18}N_2$ | 214.31 |

TABLE 1D

Relative Amounts of Products

| Product | Theoretical | Actual | Yield |
|---|---|---|---|
| 3-(2-(pyrrolidin-1-yl)ethyl)-1H-indole | 1.07 g (5 mmol) | 0.111 g (0.521 mmol) | 10.4% |

L-tryptophan (1.02 g, 1 Eq, 5.00 mmol) was dissolved in water (250 mL) containing sodium phosphate, dibasic (1.77 g, 2.5 Eq, 12.5 mmol) (pH adjusted to 7 using a 5M solution of hydrochloric acid/sodium hydroxide as needed). This sample was stirred vigorously and treated with a solution of sodium hypochlorite (558 mg, 75.0 mL, 0.1 molar, 1.5 Eq, 7.50 mmol), and the rate of sodium hypochlorite addition was below −1 mmol sodium hypochlorite per min. The rate of addition may be adjusted based on reaction component analysis by real-time HPLC-MS. The sample was allowed to stir for 2 hours at 25° C. and then excess sodium hypochlorite was destroyed by addition of sodium ascorbate in water.

Without isolation, the solution was diluted by MeOH (100 mL) and pyrrolidine (2.04 g, 2 mL, 2.3 Eq, 11.5 mmol) was added as a solution in water. The mixture was then treated with sodium triacetoxyhydroborate (2.12 g, 2 Eq, 10.0 mmol)—added in four equal portions of solid. The mixture was stirred overnight to allow the reaction to complete.

The pH of the solution was adjusted to 7.5 using sodium carbonate. The solution was then extracted into dichloromethane (4×50 mL), washed with brine (2×25 mL), dried over $MgSO_4$, and the solvent removed under reduced pressure.

The product, shown as VI in FIG. 3, was 3-(2-(pyrrolidin-1-yl)ethyl)-1H-indole, with a molecular formula of $C_{14}H_{18}N_2$, a molecular weight of 214.31 g/mol and an empirical mass of 214.14700 g/mol. At 100% yield, this would provide a theoretical mass of 1.07 g (5.00 mmol) of 3-(2-(pyrrolidin-1-yl)ethyl)-1H-indole. The actual yield of 3-(2-(pyrrolidin-1-yl)ethyl)-1H-indole was 153 mg (714 μmol), which is a yield of 14.3%.

Example II

The method shown in FIG. 7 was carried out. The reagents and products included a total volume of 420 mL, including 200 mL of water, with a reaction molarity of 26 mmolar at a temperature of 25° C. Details of the reagents are shown in Table 2A and Table 2B. Details of the products are shown in Table 2C and Table 2D.

TABLE 2A

Physical Properties of Reagents

| Reagent | Formula | MM (g/mol) |
|---|---|---|
| 3-(2-(pyrrolidin-1-yl)ethyl)-1H-indole | $C_{14}H_{18}N_2$ | 214.31 |
| EDTA disodium salt dihydrate | $C_{10}H_{18}N_2Na_2O_{10}$ | 372.24 |
| urea hydrogen peroxide | $C_6N_2O_3$ | 94.07 |
| ascorbic acid | $C_6H_8O_6$ | 176.12 |
| iron(II) sulfate heptahydrate | $FeH_{14}O_{11}S$ | 278.01 |

TABLE 2B

Relative Amounts of Reagents and Solvents

| Reagent | Eq | M (g) | mmol | Notes |
|---|---|---|---|---|
| 3-(2-(pyrrolidin-1-yl)ethyl)-1H-indole | 1 | 2.4 | 11 | N/A |
| EDTA disodium salt dihydrate | 1 | 4.1 | 11 | N/A |
| urea hydrogen peroxide | 1 | 1.0 | 11 | 0.05 molar 0.22 L |
| ascorbic acid | 2 | 3.9 | 22 | N/A |
| iron(II) sulfate heptahydrate | 0.05 | 0.15 | 0.55 | N/A |

TABLE 2C

Physical Properties of Products

| Product | Formula | MM (g/mol) |
|---|---|---|
| 3-(2-(pyrrolidin-1-yl)ethyl)-1H-indol-4-ol | $C_{14}H_{18}N_2O$ | 230.31 |
| 3-(2-(pyrrolidin-1-yl)ethyl)-1H-indol-5-ol | $C_{14}H_{18}N_2O$ | 230.31 |
| 3-(2-(pyrrolidin-1-yl)ethyl)-1H-indole-5,6-diol | $C_{14}H_{18}N_2O_2$ | 246.31 |
| 3-(2-(pyrrolidin-1-yl)ethyl)-1H-indole-4,5-diol | $C_{14}H_{18}N_2O_2$ | 246.31 |

TABLE 2D

Relative Amounts of Products

| Product | Theoretical | Actual | Yield |
|---|---|---|---|
| 3-(2-(pyrrolidin-1-yl)ethyl)-1H-indol-4-ol | 2.5 g (11 mmol) | 0.11 g (0.48 mmol) | 4.3% |
| 3-(2-(pyrrolidin-1-yl)ethyl)-1H-indol-5-ol | 2.5 g (11 mmol) | 0.19 g (0.82 mmol) | 7.5% |
| 3-(2-(pyrrolidin-1-yl)ethyl)-1H-indole-5,6-diol | 2.7 g (11 mmol) | 0.05 g (0.20 mmol) | 2.0% |
| 3-(2-(pyrrolidin-1-yl)ethyl)-1H-indole-4,5-diol | 2.5 g (11 mmol) | 0.07 g (0.30 mmol) | 3.0% |

3-(2-(pyrrolidin-1-yl)ethyl)-1H-indole (2.4 g, 1 Eq, 11 mmol) was suspended in water (200 mL) with ethylenediaminetetraacetic acid ("EDTA") disodium salt dihydrate (4.1 g, 1 Eq, 11 mmol) and the pH was adjusted to above 9. iron(II) sulfate heptahydrate (0.15 g, 0.05 Eq, 0.55 mmol) and ascorbic acid (3.9 g, 2 Eq, 22 mmol) were then charged followed by dropwise addition of a solution of urea hydrogen peroxide (1.0 g, 0.22 L, 0.05 molar, 1 Eq, 11 mmol) in water over 1 hour.

A mixture of regioisomers was formed. The crude solid was taken up in ethanol/water to produce a crude mixture of crystals including primarily 3-(2-(pyrrolidin-1-yl)ethyl)-1H-indol-4-ol (0.11 g, 0.48 mmol, 4.3%) and 3-(2-(pyrrolidin-1-yl)ethyl)-1H-indole-5-ol (0.19 g, 0.82 mmol, 7.5%). Testing shows results indicative that fractional crystallization may facilitate separation and isolation of the different regioisomers.

Example III

The method shown in FIG. 9 was carried out. The reagents were mixed into a total volume of 5 mL, including 5 mL of dichloromethane, with a reaction molarity of 200 mmolar at a temperature of 25° C. Details of the reagents are shown in Table 3A and Table 3B.

TABLE 3A

Physical Properties of Reagents

| Reagent | Formula | MM (g/mol) |
|---|---|---|
| methyl (ethoxycarbonyl)-L-tryptophanate | $C_{15}H_{18}N_2O_4$ | 290.32 |
| pyridine | $C_5H_5N$ | 79.10 |
| pinacol | $C_6H_{14}O_2$ | 118.18 |
| boron tribromide | $BBr_3$ | 250.52 |

TABLE 3B

Relative Amounts of Reagents and Solvents

| Reagent | Eq | M (g) | mmol | Notes |
|---|---|---|---|---|
| methyl (ethoxycarbonyl)-L-tryptophanate | 1 | 0.3 | 1 | N/A |
| dichloromethane | N/A | N/A | N/A | 5 mL |
| pyridine | 1.5 | 0.1 | 2 | 0.1 mL 0.978 g/mL |
| pinacol | 1.5 | 0.2 | 2 | N/A |
| boron tribromide | 1.1 | 0.3 | 1 | 0.1 mL 2.650 g/mL |

TABLE 3C

Physical Properties of Products

| Product | Formula | MM (g/mol) |
|---|---|---|
| methyl (S)-2-((methoxycarbonyl)amino)-3-(4-(4,4,5,5-tetramethyl-1,3,2-dioxaborolan-2-yl)-1H-indol-3-yl)propanoate | $C_{20}H_{27}BN_2O_6$ | 402.25 |

TABLE 3D

| Relative Amounts of Products | | | |
|---|---|---|---|
| Product | Theoretical | Actual | Yield |
| methyl (S)-2-((methoxycarbonyl)-amino)-3-(4-(4,4,5,5-tetramethyl-1,3,2-dioxaborolan-2-yl)-1H-indol-3-yl)propanoate | 0.402 g (1 mmol) | 0.09 g (0.223 mmol) | 22.3% |

Methyl (ethoxycarbonyl)-L-tryptophanate (0.3 g, 1 Eq, 1 mmol) was dissolved in dry degassed dichloromethane (5 mL) under argon gas. Boron tribromide (0.3 g, 0.1 mL, 1.1 Eq, 1 mmol) was added in one charge and left to stir for 9 hours at 25° C.

The reaction was quenched by charging pyridine (0.1 g, 0.1 mL, 1.5 Eq, 2 mmol) and pinacol (0.2 g, 1.5 Eq, 2 mmol).

The product, shown as V in FIG. 9, was methyl (S)-2-((ethoxycarbonyl)amino)-3-(4-(4,4,5,5-tetramethyl-1,3,2-dioxaborolan-2-yl)-1H-indol-3-yl)propanoate, with a molecular formula of $C_{21}H_{29}BN_2O_6$, a molecular weight of 416.28 g/mol and an empirical mass of 416.21187 g/mol. At 100% yield, this would provide a theoretical mass of 0.4 g (1.00 mmol) of methyl (S)-2-((ethoxycarbonyl)amino)-3-(4-(4,4,5,5-tetramethyl-1,3,2-dioxaborolan-2-yl)-1H-indol-3-yl)propanoate. The actual yield of methyl (S)-2-((ethoxycarbonyl)amino)-3-(4-(4,4,5,5-tetramethyl-1,3,2-dioxaborolan-2-yl)-1H-indol-3-yl)propanoate was 0.09 g (0.3 mmol), which is a yield of 20.0%.

Example IV

The method shown in FIG. 12 was carried out. The reagents were mixed into a total volume of 10 mL tetrahydrofuran, with a reaction molarity of 100 mmolar at a temperature of 45° C. Details of the reagents are shown in Table 4A and Table 4B.

TABLE 4A

| Physical Properties of Reagents | | |
|---|---|---|
| Reagent | Formula | MM (g/mol) |
| 1H-indol-4-yl acetate | $C_{10}H_9NO_2$ | 175.19 |
| allyl acetate | $C_5H_8O_2$ | 100.12 |
| tetrakis(triphenylphosphine) palladium | $C_{72}H_{60}P_4Pd$ | 1155.59 |

TABLE 4B

| Relative Amounts of Reagents and Solvents | | | | |
|---|---|---|---|---|
| Reagent | Eq | M (g) | mmol | Notes |
| 1H-indol-4-yl acetate | 1 | 0.2 | 1 | N/A |
| allyl acetate | 1 | 0.1 | 1 | N/A |
| tetrakis(triphenylphosphine) palladium | 0.01 | 0.01 | 0.01 | N/A |

TABLE 4C

| Physical Properties of Products | | |
|---|---|---|
| Product | Formula | MM (g/mol) |
| 3-allyl-1H-indol-4-yl acetate | $C_{13}H_{13}NO_2$ | 215.25 |

TABLE 4D

| Relative Amounts of Products | | | |
|---|---|---|---|
| Product | Theoretical | Actual | Yield |
| 3-allyl-1H-indol-4-yl acetate | 0.01 g (0.05 mmol) | 0.002 g (0.01 mmol) | 22% |

1H-indol-4-yl acetate (0.2 g, 1 Eq, 1 mmol) is dissolved in dry THF (10 mL) and treated sequentially with allyl acetate (0.1 g, 1 Eq, 1 mmol) and Pd(PPh$_3$)$_4$ (0.01 g, 0.01 Eq, 0.01 mmol). The sample is sealed and heated under N2 for 2 hrs.

The resulting crude mixture was purified by column chromatography. The product, shown in FIG. 12, was 3-allyl-1H-indol-4-yl acetate, with a molecular formula of $C_{13}H_{13}NO_2$, a molecular weight of 215.25 g/mol and an empirical mass of 215.09463 g/mol. At 100% yield, this would provide a theoretical mass of 0.2 g (1.00 mmol) of 3-allyl-1H-indol-4-yl acetate. The actual yield of 3-allyl-1H-indol-4-yl acetate was 0.18 g (0.84 mmol), which is a yield of 80.0%.

Example V

The method shown in FIG. 13 was carried out as a sequential telescoped reaction without isolation of intermediates. The reagents were mixed into a total volume of 10 mL, including 10 mL of tert-butanol, with a reaction molarity of 5 mmolar at a temperature of 25° C. Details of the reagents are shown in Table 5A and Table 5B.

TABLE 5A

| Physical Properties of Reagents | | |
|---|---|---|
| Reagent | Formula | MM (g/mol) |
| pyrrolidine | $C_4H_9N$ | 71.12 |
| 3-allyl-1H-indol-4-yl acetate | $C_{13}H_{13}NO_2$ | 215.25 |
| tert-butanol | $C_4H_{10}O$ | 74.12 |
| Co-salen | $C_{16}H_{14}CoN_2O_2$ | 325.23 |
| sodium triacetoxyhydroborate | $C_6H_{10}BNaO_6$ | 211.94 |
| hydrogen peroxide | $H_2O_2$ | 34.01 |

TABLE 5B

| Relative Amounts of Reagents and Solvents | | | | |
|---|---|---|---|---|
| Reagent | Eq | M (g) | mmol | Notes |
| pyrrolidine | 2 | 0.007 | 0.10 | 9 μL 0.75 g/mL |
| 3-allyl-1H-indol-4-yl acetate | 1 | 0.010 | 0.05 | N/A |
| tert-butanol | N/A | N/A | N/A | 10 mL |
| Co-salen | 0.01 | 0.0002 | 0.0005 | N/A |
| sodium triacetoxyhydroborate | 3 | 0.030 | 0.20 | N/A |
| hydrogen peroxide | 2 | 0.010 | 0.10 | Volume 0.01 mL Density 1.110 g/mL 25% Wt in water |

TABLE 5C

Physical Properties of Products

| Product | Formula | MM (g/mol) |
|---|---|---|
| 3-(2-(pyrrolidin-1-yl)ethyl)-1H-indol-4-yl acetate | $C_{16}H_{20}N_2O_2$ | 272.35 |

TABLE 5D

Relative Amounts of Products

| Product | Theoretical | Actual | Yield |
|---|---|---|---|
| 3-(2-(pyrrolidin-1-yl)ethyl)-1H-indol-4-yl acetate | 0.01 g (0.05 mmol) | 0.002 g (0.01 mmol) | 20% |

3-allyl-1H-indol-4-yl acetate (0.01 g, 1 Eq, 0.05 mmol) was dissolved in tert-butanol (10 mL) and then treated with Co-salen (0.2 mg, 0.01 Eq, 0.5 μmol). The mixture was then treated via dropwise addition of hydrogen peroxide (0.01 g, 0.01 mL, 25% Wt, 2 Eq, 0.1 mmol) over 1 hr. After the reaction was completed the solution was treated with sodium sulphite and then pyrrolidine (7 mg, 9 μL, 2 Eq, 0.1 mmol) was added as a solution in water. The pH was adjusted to 8-9 using sodium carbonate. The reaction was then treated with sodium triacetoxyhydroborate (0.03 g, 3 Eq, 0.2 mmol) and allowed to react for thirty minutes. The crude mixture was evaporated to dryness and then immediately purified by column chromatography (DCM:MeOH) to give 3-(2-(pyrrolidin-1-yl)ethyl)-1H-indol-4-yl acetate 0.002 g (0.01 mmol, 20.0% yield)

Example VI

The method shown in FIG. 15 was carried out. The reagents and products included a total volume of 21 mL, including 20 mL of toluene, with a reaction molarity of 220 mmolar at a temperature of 45° C. Details of the reagents are shown in Table 6A and Table 6B. Details of the products are shown in Table 6C and Table 6D.

TABLE 6A

Physical Properties of Reagents

| Reagent | Formula | MM (g/mol) |
|---|---|---|
| 1H-indol-4-yl acetate | $C_{10}H_9NO_2$ | 175.19 |
| 3-bromoprop-1-ene | $C_3H_5Br$ | 120.98 |
| copper (II) acetate | $C_4H_6CuO_4$ | 181.63 |
| 1,8-diazabicyclo[5.4.0]undec-7-ene | $C_9H_{16}N_2$ | 152.24 |

TABLE 6B

Relative Amounts of Reagents and Solvents

| Reagent | Eq | M (g) | mmol | Notes |
|---|---|---|---|---|
| 1H-indol-4-yl acetate | 1 | 0.79 | 4.5 | N/A |
| 3-bromoprop-1-ene | 1 | 0.54 | 4.5 | N/A |
| copper (II) acetate | 1 | 0.82 | 4.5 | N/A |
| 1,8-diazabicyclo[5.4.0]undec-7-ene | 1 | 0.69 | 4.5 | Volume 0.68 mL Density 1.010 g/mL |

TABLE 6C

Physical Properties of Products

| Product | Formula | MM (g/mol) |
|---|---|---|
| 3-allyl-1H-indol-4-yl acetate | $C_{13}H_{13}NO_2$ | 215.25 |
| 1-allyl-1H-indol-4-yl acetate | $C_{13}H_{13}NO_2$ | 215.25 |

TABLE 6D

Relative Amounts of Products

| Product | Theoretical | Actual | Yield |
|---|---|---|---|
| 3-allyl-1H-indol-4-yl acetate | 0.97 g (4.5 mmol) | 0.21 g (0.98 mmol) | 22% |
| 1-allyl-1H-indol-4-yl acetate | 0.97 g (4.5 mmol) | 0.05 g (0.20 mmol) | 5% |

A solution of 1H-indol-4-yl acetate (0.79 g, 1 Eq, 4.5 mmol) dissolved in toluene (20 mL) and treated with 1,8-Diazabicyclo[5.4.0]undec-7-ene ("DBU") (0.69 g, 0.68 mL, 1 Eq, 4.5 mmol) and copper (II) acetate (0.82 g, 1 Eq, 4.5 mmol). The sample was heated to 45° C. for 25 min, then 3-bromoprop-1-ene (0.54 g, 1 Eq, 4.5 mmol) was added dropwise over 1 hour. The reaction was left to stand for an additional 2 hours then cooled and quenched with saturated ammonium chloride solution.

This reaction produces a mixture of products including 3-allyl-1H-indol-4-yl acetate (0.21 g, 22%) from allylation of the indole ring at a carbon on the indole ring and 1-allyl-1H-indol-4-yl acetate (0.21 g, 5%) from allylation of the indole ring at the nitrogen on the indole ring.

Example VII

The method shown in FIG. 16 was carried out. The reagents and products included a total volume of 183.4 mL, including 130 mL of dichloromethane, with a reaction molarity of 410 mmolar at a temperature of 25° C. Details of the reagents are shown in Table 7A and Table 7B. Details of the products are shown in Table 7C and Table 7D.

TABLE 7A

Physical Properties of Reagents

| Reagent | Formula | MM (g/mol) |
|---|---|---|
| 4-hydroxyindole | $C_8H_7NO$ | 133.15 |
| acetic anhydride | $C_4H_6O_3$ | 102.1 |
| pyridine | $C_5H_5N$ | 79.1 |

TABLE 7B

Relative Amounts of Reagents and Solvents

| Reagent | Eq | M (g) | mmol | Notes |
|---|---|---|---|---|
| 4-hydroxyindole | 1 | 10 | 75.1 | N/A |
| dichloromethane | N/A | N/A | N/A | 130 mL |
| acetic anhydride | 4 | 30.67 | 300 | Density of 1.08 Volume of 28.4 mL |
| pyridine | 4.1 | 24.36 | 307 | Density of 0.98 Volume of 25 mL |

TABLE 7C

Physical Properties of Products

| Product | Formula | MM (g/mol) |
|---|---|---|
| 1H-indol-4-yl acetate | $C_{10}H_9NO_2$ | 175.19 |

TABLE 7D

Relative Amounts of Products

| Product | Theoretical | Actual | Yield |
|---|---|---|---|
| 1H-indol-4-yl acetate | 13.16 | 8.6 | 65% |

4-hydroxyindole (10.00 g, 1 Eq, 75.10 mmol) and dichloromethane (130 mL) were combined in a round-bottom flask. Acetic anhydride (30.67 g, 28.4 mL, 4 eq, 300.4 mmol) was added in one portion. Pyridine (24.36 g, 25 mL, 4.1 eq, 307.9 mmol) was added in one portion. The reaction mixture was stirred for 16 hours and then the reaction was concentrated in vacuo.

The crude material was diluted with 650 ml toluene and extracted with brine (5×250 ml). The organic phase was dried over anhydrous sodium sulfate and filtered through a pad of Celite™ diatomaceous earth.

The resulting crude 1H-indol-4-yl acetate (8.6 g, 49.1 mmol, 65%) was recrystallized in toluene (100 mL) as a light brown solid.

The product 1H-indol-4-yl acetate was characterized by 1H NMR (400 MHz, chloroform-D). The observed peaks on 1H NMR were δ 2.43 (s, 4H) 6.38-6.45 (m, 1H) 6.89 (dd, =4.44, 3.76 Hz, 1H) 7.02 (dd, =3.24, 2.56 Hz, 1H) 7.14-7.17 (m, 2H) 8.33 (br. s., 1H).

Figure 32:
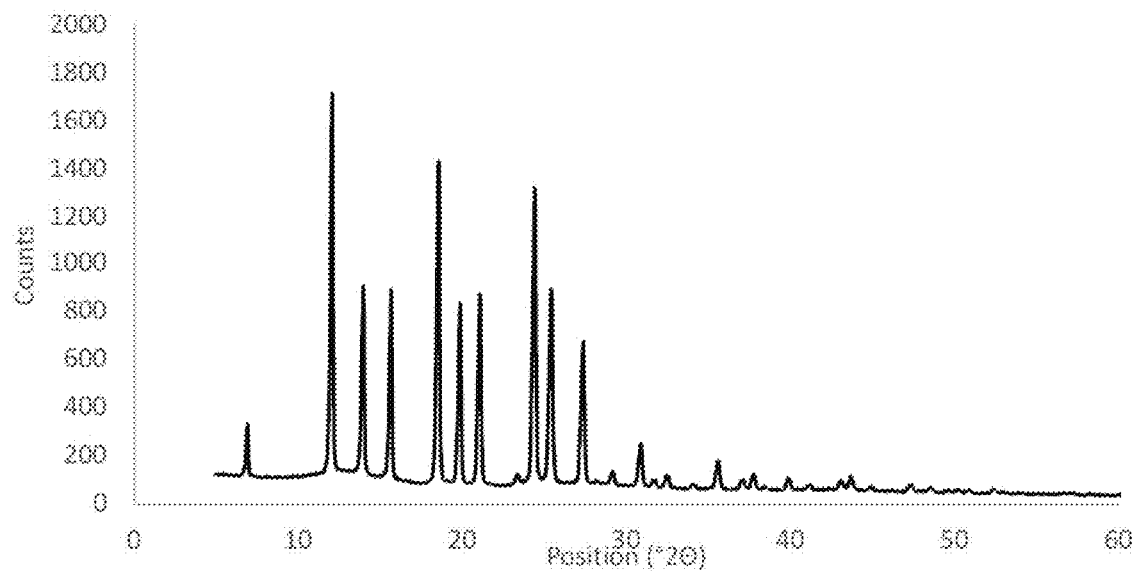
FIG. 32 shows the XRD pattern of 1H-indol-4-yl acetate crystals grown from toluene.

A powder x-ray diffraction ("XRD") pattern was obtained for 1H-indol-4-yl acetate crystals grown from toluene. The XRD pattern is shown in FIG. 32.

Example VIII

The method shown in FIG. 16 was carried out. The reagents and products included a total volume of 307 mL, including 200 mL of toluene, with a reaction molarity of 490 mmolar at a temperature of 25° C. Details of the reagents are shown in Table 8A and Table 8B. Details of the products are shown in Table 8C and Table 8D.

TABLE 8A

Physical Properties of Reagents

| Reagent | Formula | MM (g/mol) |
|---|---|---|
| 4-hydroxyindole | $C_8H_7NO$ | 133.15 |
| acetic anhydride | $C_4H_6O_3$ | 102.1 |
| pyridine | $C_5H_5N$ | 79.1 |

TABLE 8B

Relative Amounts of Reagents and Solvents

| Reagent | Eq | M (g) | mmol | Notes |
|---|---|---|---|---|
| 4-hydroxyindole | 1 | 10 | 75.1 | N/A |
| Toluene | N/A | N/A | N/A | 200 mL |
| acetic anhydride | 4 | 61.3 | 601 | Density of 1.08 g/mL Volume of 56.8 mL |

TABLE 8B-continued

Relative Amounts of Reagents and Solvents

| Reagent | Eq | M (g) | mmol | Notes |
|---|---|---|---|---|
| pyridine | 4.1 | 48.8 | 616 | Density of 0.98 Volume of 50 mL |

TABLE 8C

Physical Properties of Products

| Product | Formula | MM (g/mol) |
|---|---|---|
| 1H-indol-4-yl acetate | $C_{10}H_9NO_2$ | 175.19 |

TABLE 8D

Relative Amounts of Products

| Product | Theoretical | Actual | Yield |
|---|---|---|---|
| 1H-indol-4-yl acetate | 26.3 | 19.1 | 72.6% |

4-hydroxyindole (20.00 g, 1 Eq, 150.2 mmol) and toluene (200 mL) were combined in a round-bottom flask. Acetic anhydride (61.3 g, 56.8 mL, 4 eq, 600.8 mmol) was added in one portion. Pyridine (48.8 g, 50 mL, 4.1 eq, 616 mmol) was added in one portion. The reaction mixture was stirred for 1 hour and then the reaction was quenched with an aqueous solution of hydrochloric acid (0.5M, 200 mL). NOTE: The quench is slightly exothermic.

The resultant reaction mixture was allowed to cool to room temperature.

The aqueous solution was removed and the organic solution was washed with additional aqueous solution of hydrochloric acid (0.5M, 2×200 mL), saturated solution of sodium bicarbonate (1×200 mL) and brine (1×200 mL). The organic layer was concentrated under reduced pressure to dryness.

The crude material was dissolved in hot toluene (150 mL) and precipitated with n-hexanes (300 mL) to afford the product, 1H-indol-4-yl acetate (19.1 g, 109 mmol, 72.6%) as a light gray powder.

The product was characterized by 1H NMR (400 MHz, chloroform-D). The observed peaks on 1H NMR were δ 2.43 (s, 4H) 6.38-6.45 (m, 1H) 6.89 (dd, =4.44, 3.76 Hz, 1H) 7.02 (dd, =3.24, 2.56 Hz, 1H) 7.14-7.17 (m, 2H) 8.33 (br. s., 1H).

Example IX

The method shown in FIG. 16 was carried out. The reagents and products included a total volume of 307 mL, including 200 mL of toluene, with a reaction molarity of 490 mmolar at a temperature of 25° C. Details of the reagents are shown in Table 9A and Table 9B. Details of the products are shown in Table 9C and Table 9D.

TABLE 9A

Physical Properties of Reagents

| Reagent | Formula | MM (g/mol) |
|---|---|---|
| 4-hydroxyindole | $C_8H_7NO$ | 133.15 |
| acetic anhydride | $C_4H_6O_3$ | 102.1 |
| pyridine | $C_5H_5N$ | 79.1 |

TABLE 9B

Relative Amounts of Reagents and Solvents

| Reagent | Eq | M (g) | mmol | Notes |
|---|---|---|---|---|
| 4-hydroxyindole | 1 | 20 | 150 | N/A |
| Toluene | N/A | N/A | N/A | 200 mL |
| acetic anhydride | 4 | 61.3 | 601 | Density of 1.08 g/mL Volume of 56.8 mL |
| pyridine | 4.1 | 48.8 | 616 | Density of 0.98 Volume of 50 mL |

TABLE 9C

Physical Properties of Products

| Product | Formula | MM (g/mol) |
|---|---|---|
| 1H-indol-4-yl acetate | $C_{10}H_9NO_2$ | 175.19 |

TABLE 9D

Relative Amounts of Products

| Product | Theoretical | Actual | Yield |
|---|---|---|---|
| 1H-indol-4-yl acetate | 26.3 | 18.09 | 69% |

4-hydroxyindole (20.00 g, 1 Eq, 150.2 mmol) and toluene (200 mL) were combined in a round-bottom flask. Acetic anhydride (61.3 g, 56.8 mL, 4 eq, 600.8 mmol) was added in one portion. Pyridine (48.8 g, 50 mL, 4.1 eq, 616 mmol) was added in one portion. The reaction mixture was stirred for 1 hour and then the reaction was quenched with an aqueous solution of hydrochloric acid (0.5M, 200 mL).

The resultant reaction mixture was allowed to cool to room temperature.

The aqueous solution was removed and the organic solution was washed with an aqueous solution of hydrochloric acid (0.5M, 2×200 mL), saturated solution of sodium bicarbonate (1×200 mL) and brine (1×200 mL)

The organic solution was concentrated under reduced pressure to dryness.

The crude material was purified by crystallization in hot toluene (60 mL at 60° C.). A second crop of crystals was obtained by concentrating the filtrate from the first crystallization. The product, 1H-indol-4-yl acetate (18.09 g, 103.2 mmol, 69%) was isolated as a light gray powder.

The product was characterized by 1H NMR (400 MHz, chloroform-D). The observed peaks on 1H NMR were δ 2.43 (s, 4H) 6.38-6.45 (m, 1H) 6.89 (dd, =4.44, 3.76 Hz, 1H) 7.02 (dd, =3.24, 2.56 Hz, 1H) 7.14-7.17 (m, 2H) 8.33 (br. s., 1H).

Example X

The method shown in FIG. 17 was carried out. The reagents and products included a total volume of 360 mL, including 300 mL of acetonitrile, with a reaction molarity of 209 mmolar at room temperature. Details of the reagents are shown in Table 10A and Table 10B. Details of the products are shown in Table 10C and Table 10D.

TABLE 10A

Physical Properties of Reagents

| Reagent | Formula | MM (g/mol) |
|---|---|---|
| 1H-indol-4-ol | $C_8H_7NO$ | 133.15 |
| potassium t-butoxide | $C_4H_9KO$ | 64.06 |
| tetrabenzyl diphosphate | $C_{28}H_{28}O_7P_2$ | 538.47 |

TABLE 10B

Relative Amounts of Reagents and Solvents

| Reagent | Eq | M (g) | mmol | Notes |
|---|---|---|---|---|
| 1H-indol-4-ol | 1.0 | 10.0 | 75.10 | N/A |
| acetonitrile | N/A | N/A | N/A | 300 mL |
| potassium tert-butoxide | 1.0 | N/A | 60.08 | 60.08 mL 1.0 M in tetrahydrofuran |
| tetrabenzyl diphosphate | 1.05 | 42.46 | 78.86 | N/A |

TABLE 10C

Physical Properties of Products

| Product | Formula | MM (g/mol) |
|---|---|---|
| dibenzyl (1H-indol-4-yl) phosphate | $C_{22}H_{20}NO_4P$ | 393.38 |

TABLE 10D

Relative Amounts of Products

| Product | Theoretical | Actual | Yield |
|---|---|---|---|
| dibenzyl (1H-indol-4-yl) phosphate | 29.54 g | 15.44 g | 52.26% |

300 mL of acetonitrile was added to a 500 mL flask and 1H-indol-4-ol (10 g, 1 Eq, 75.00 mmol) and dibenzyl (1H-indol-4-yl) phosphate (42.46 9, 1.05 Eq, 78.86 mmol) were added to the flask. A solution of potassium tert-butoxide (1.0 M in THF, 60.08 mL, 0.8 Eq, 60.08 mmol) was added dropwise over a period of 100 min. The reaction mixture formed a crystalline solid which was filtered off and discarded. The remaining supernatant was concentrated under vacuum before being reconstituted in toluene and extracted with an aqueous solution of sodium hydroxide (1M, 3×300 mL) and brine (2×300 mL). The combined organic phases were dried with anhydrous sodium sulfate, applied to a pad of silica gel and Celite diatomaceous earth, eluting with 1:1 hexanes:ethyl acetate. and then concentrated under vacuum. The solvent eluent was concentrated to dryness to yield a crude crystalline solid, which was purified by trituration using methyl tert-butyl ether. Filtration of this slurry gave dibenzyl (1H-indol-4-yl) phosphate (15.44 g, 39.25 mmol, 52.26%) as a white solid.

The product was characterized by 1H NMR (400 MHz, chloroform-D). The observed peaks on 1H NMR were δ 8.85 (s, 1H), 7.36 (s, 10H), 7.21 (d, J=7.5 Hz, 1H), 7.14-7.02 (m, 3H), 6.64 (t, J=2.5 Hz, 1H), 5.21 (dt, J=8.2, 5.0 Hz, 4H).

Figure 33:
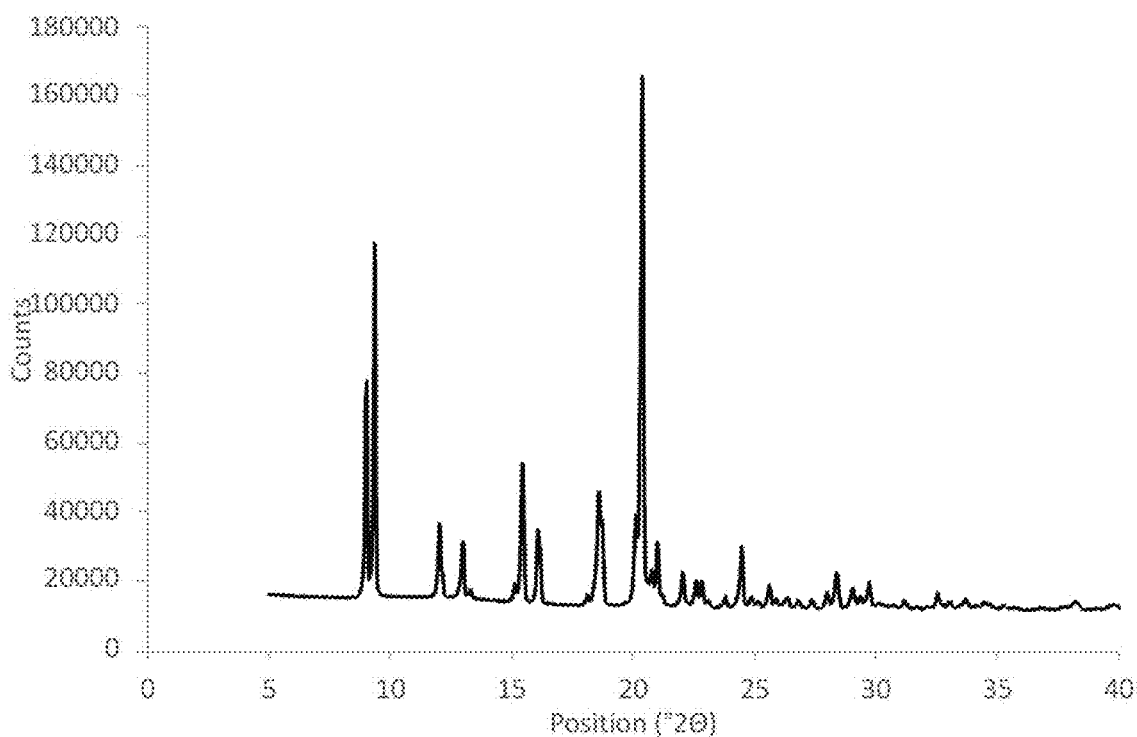
FIG. 33 shows the XRD pattern of dibenzyl (1H-indol-4-yl) phosphate crystals grown from 3:2 toluene:heptane.

An XRD pattern was obtained for dibenzyl (1H-indol-4-yl) phosphate crystals grown from 3:2 toluene:heptane. The XRD pattern is shown in FIG. 33.

Example XI

The method shown in FIG. 18 was carried out. The reagents and products included a total volume of 150 mL, including 150 mL of THF, with a reaction molarity of 30 mmolar at a temperature of 50° C. Details of the reagents are shown in Table 11A and Table 11B. Details of the products are shown in Table 11C and Table 11D.

TABLE 11A

Physical Properties of Reagents

| Reagent | Formula | MM (g/mol) |
|---|---|---|
| 4-acetyl-indole | $C_{10}H_9NO_2$ | 175.2 |
| allyl alcohol | $C_3H_6O$ | 58.1 |
| triethyl borane | $C_6H_{15}B$ | 98.0 |
| tetrakis(triphenylphosphine)palladium | $C_{27}H_{60}P_4Pd$ | 1155.6 |

TABLE 11B

Relative Amounts of Reagents and Solvents

| Reagent | Eq | M (g) | mmol | Notes |
|---|---|---|---|---|
| 4-acetyl-indole | 1 | 5.26 | 30 | N/A |
| tetrahydrofuran | N/A | N/A | N/A | 150 mL |
| allyl alcohol | 1.5 | N/A | 45 | Density 0.854 g/mL Volume 3.06 mL |
| triethyl borane | 0.5 | 15 mL | 15 | 1.0M in THF Volume 15.0 mL |
| tetrakis-(triphenylphosphine)palladium | 0.016 | 563 mg | 0.487 | N/A |

TABLE 11C

Physical Properties of Products

| Product | Formula | MM (g/mol) |
|---|---|---|
| 3-allyl-1H-indol-4-yl acetate | $C_{13}H_{13}NO_2$ | 215.09 |

TABLE 11D

Relative Amounts of Products

| Product | Theoretical | Actual | Yield |
|---|---|---|---|
| 3-allyl-1H-indol-4-yl acetate | 6.4 | 5.2 | 81% |

150 mL of THF was added to a 250 mL round-bottom flask and sparged with argon. While sparging, 1H-indol-4-yl acetate (5.256 g, 1 Eq, 30.00 mmol) and allyl alcohol (3.06 mL, 1.5 Eq, 45.00 mmol) were added to the flask. Sparging with argon was continued for 30 minutes. After sparging, triethylborane (1.0 M in hexanes, 15.00 mL, 0.5 Eq, 15.00 mmol) and tetrakis (triphenylphosphine) palladium (563.2 mg, 0.0162 Eq, 487.4 μmol) were sequentially added to the reaction.

The reaction was heated at 50° C. and stirred for 4 hours under an argon atmosphere. Upon completion, charcoal (30 Wt %, 1.58 g) was added to the reaction mixture and the resultant mixture was filtered through a pad of Celite diatomaceous earth using hexanes (100 mL) as eluent. The crude material was purified by flash chromatography using hexanes:ethyl acetate (85:15) as eluent.

Fractions containing the desired product were collected and concentrated in vacuo to afford 3-allyl-1H-indol-4-yl acetate (5.2 g, 24 mmol, 81%) as a light-yellow oil.

The product was characterized by 1H NMR (300 MHz, chloroform-D). The observed peaks on 1H NMR were δ 3.64 (dq, J=6.40, 1.28 Hz, 2H) 4.98-5.10 (m, 2H) 5.12 (d, J=2.30 Hz, 2H) 5.15 (d, J=2.05 Hz, 2H) 6.08 (ddt, J=16.93, 10.21, 6.53, 6.53 Hz, 1H) 6.85-6.90 (m, 1H) 7.02-7.08 (m, 2H) 7.11-7.16 (m, 1H) 7.30 (s, 10H) 8.12 (br. s., 1H).

Example XII

The method shown in FIG. 18 was carried out. The reagents and products included a total volume of 338 mL, including 300 mL of 2-methyltetrahydrofuran, with a reaction molarity of 295 mmolar at a temperature of 60° C. Details of the reagents are shown in Table 12A and Table 12B. Details of the products are shown in Table 12C and Table 12D.

TABLE 12A

Physical Properties of Reagents

| Reagent | Formula | MM (g/mol) |
|---|---|---|
| 4-acetyl-indole | $C_{10}H_9NO_2$ | 175.2 |
| allyl alcohol | $C_3H_6O$ | 58.1 |
| triethyl borane | $C_6H_{15}B$ | 98.0 |
| tetra(triphenylphosphine)palladium | $C_{27}H_{60}P_4Pd$ | 1155.6 |

TABLE 12B

Relative Amounts of Reagents and Solvents

| Reagent | Eq | M (g) | mmol | Notes |
|---|---|---|---|---|
| 4-acetyl-indole | 1 | 17.5 | 99.9 | N/A |
| 2-methyltetrahydrofuran | N/A | N/A | N/A | 300 mL |
| allyl alcohol | 1.5 | N/A | 120 | Density 0.854 g/mL Volume 8.15 mL |
| triethyl borane | 0.3 | N/A | 30.0 | 1.0M in 2-Me—THF Volume 30.0 mL |
| tetra(triphenylphosphine)-palladium | 0.03 | 3.46 g | 3.00 | N/A |

TABLE 12C

Physical Properties of Products

| Product | Formula | MM (g/mol) |
|---|---|---|
| 3-allyl-1H-indol-4-yl acetate | $C_{13}H_{13}NO_2$ | 215.09 |

Relative Amounts of Products

| Product | Theoretical | Actual | Yield |
|---|---|---|---|
| 3-allyl-1H-indol-4-yl acetate | 6.4 | N/A | N/A |

300 mL of tetrahydrofuran was added to a 500 mL round-bottom flask and sparged with argon. While sparging, 1H-indol-4-yl acetate (17.5 g, 1 Eq, 99.9 mmol) and allyl alcohol (8.15 mL, 1.5 Eq, 120 mmol) were added to the flask. Sparging with argon was continued for 30 minutes. After sparging, triethylborane (1.0 M in tetrahydrofuran, 30.0 mL, 0.3 Eq, 30.0 mmol) and tetrakis (triphenylphosphine)palladium (3.46 g, 0.03 Eq, 3.00 mmol) were sequentially added to the reaction.

The reaction was heated at 60° C. and stirred for 2 hours under an argon atmosphere. Upon completion, the crude reaction mixture was quenched with water then concentrated in vacuo. The resulting crude mixture was diluted with ethyl acetate (200 mL) and the aqueous phase was removed. The organic phase was further washed with water (3×200 mL), dried over anhydrous sodium sulfate (30 g), concentrated under reduced pressure and dried under vacuum for 2 h. The crude material was used in the subsequent reaction without further purification. The subsequent reaction is detailed in Example XVI.

Example XIII

The method shown in FIG. 19 was carried out. The reagents and products included a total volume of 21 mL, including 20 mL of THF, with a reaction molarity of 95 mmolar at a temperature of 45° C. Details of the reagents are shown in Table 13A and Table 13B. Details of the products are shown in Table 13C and Table 13D.

| Physical Properties of Reagents | | |
|---|---|---|
| Reagent | Formula | MM (g/mol) |
| dibenzyl (1H-indol-4-yl) phosphate | $C_{22}H_{20}NO_4P$ | 393.38 |
| allyl alcohol | $C_3H_6O$ | 58.1 |
| triethyl borane | $C_6H_{15}B$ | 98.0 |
| tetrakis(triphenylphosphine)palladium | $C_{72}H_{60}P_4Pd$ | 1155.6 |

TABLE 13B

Relative Amounts of Reagents and Solvents

| Reagent | Eq | M (g) | mmol | Notes |
|---|---|---|---|---|
| dibenzyl (1H-indol-4-yl) phosphate | 1 | 0.787 | 2.0 | N/A |
| tetrahydrofuran | N/A | N/A | N/A | 20 mL |
| allyl alcohol | 1.05 | N/A | 6.3 | Density 0.854 g/mol Volume 0.143 mL |
| triethyl borane | 0.4 | N/A | 0.8 | 1.0M in THF Volume 0.8 mL |
| tetrakis(triphenylphosphine) palladium | 0.05 | 0.116 | 0.1 | N/A |

TABLE 13C

Physical Properties of Products

| Product | Formula | MM (g/mol) |
|---|---|---|
| 3-allyl-1H-indol-4-yl dibenzyl phosphate | $C_{25}H_{24}NO_4P$ | 433.44 |

TABLE 13D

Relative Amounts of Products

| Product | Theoretical | Actual | Yield |
|---|---|---|---|
| 3-allyl-1H-indol-4-yl dibenzyl phosphate | 0.867 | 0.56 | 65% |

Dibenzyl (1H-indol-4-yl) phosphate (0.787 g, 1 Eq, 2.00 mmol) and tetrakis(triphenylphosphine) palladium (0.116 g, 0.05 Eq, 0.1 mmol) were added to a 100 mL flask and sparged with argon. While sparging, THF (20 mL) was added to the flask, followed by allyl alcohol (0.143 mL, 1.05 Eq, 2.10 mmol, and finally triethylborane (1.0 M in THF, 0.80 mL, 0.4 Eq, 0.80 mmol).

The reaction was heated at 45° C. and stirred for 5 hours under an argon atmosphere. Upon completion, reaction mixture was concentrated under vacuum. Then the crude material was purified by flash chromatography using gradient hexanes:ethyl acetate (1:1) as eluent.

Fractions containing the desired product were collected and concentrated in vacuo to afford 3-allyl-1H-indol-4-yl dibenzyl phosphate (0.56 g, 1.3 mmol, 65%) as light-yellow oil.

The product was characterized by 1H NMR (300 MHz, chloroform-D). The observed peaks on 1H NMR were NMR (400 MHz, CDCl3) δ 9.12 (s, 1H), 7.36 (q, J=2.2 Hz, 10H), 7.23-7.10 (m, 2H), 7.04 (t, J=7.9 Hz, 1H), 6.89-6.78 (m, 1H), 6.28-6.06 (m, 1H), 5.24-5.17 (m, 4H), 5.17-5.07 (m, 2H), 3.73 (dq, J=6.5, 1.3 Hz, 2H).

Example XIV

The method shown in FIG. 20 was carried out. The reagents and products included a total volume of 140 mL, including 70 mL of tetrahydrofuran and 70 mL of water, with a reaction molarity of 50 mmolar at a temperature of 25° C. Details of the reagents are shown in Table 14A and Table 14B. Details of the products are shown in Table 14C and Table 14D.

TABLE 14A

Physical Properties of Reagents

| Reagent | Formula | MM (g/mol) |
|---|---|---|
| 3-allyl-1H-indol-4-yl acetate | $C_{13}H_{13}NO_2$ | 215.25 |
| potassium osmate dihydrate | $H_4K_2O_6Os$ | 368.45 |
| 4-methylmorpholine 4-oxide | $C_5H_{11}NO_2$ | 117.15 |

TABLE 14B

Relative Amounts of Reagents and Solvents

| Reagent | Eq | M (g) | mmol | Notes |
|---|---|---|---|---|
| 3-allyl-1H-indol-4-yl acetate | 1 | 1.52 g | 7.06 mmol | N/A |
| tetrahydrofuran | N/A | N/A | N/A | 70 mL |
| water | N/A | N/A | N/A | 70 mL |
| potassium osmate dihydrate | 0.05 | 0.13 g | 0.353 mmol | N/A |
| 4-methylmorpholine 4-oxide | 5 | 4.14 g | 35.3 mmol | N/A |

TABLE 14C

Physical Properties of Products

| Product | Formula | MM (g/mol) |
|---|---|---|
| 3-(2,3-dihydroxypropyl)-1H-indol-4-yl acetate | $C_{13}H_{15}NO_4$ | 249.27 |

TABLE 14D

Relative Amounts of Products

| Product | Theoretical | Actual | Yield |
|---|---|---|---|
| 3-(2,3-dihydroxypropyl)-1H-indol-4-yl acetate | 1.76 g | 1.31 g | 74.4% |

70 mL of tetrahydrofuran and 70 mL of water was added to a 250 mL round-bottom flask containing 3-allyl-1H-indol- 4-yl acetate (1.52 g, 7.06 mmol). 4-Methylmorpholine 4-oxide (4.14 g, 35.5 mmol; labelled as "NMO" in all figures) was added in one portion. Potassium Osmate (130 mg, 0.353 mmol) was added in one portion.

The reaction was stirred at 25° C. for 2 hours. Upon completion, the reaction was quenched with a saturated solution of sodium thiosulfate (60 mL). The organic phase was separated and the aqueous phase was extracted with ethyl acetate (3×100 mL). The combined organic extracts were concentrated in vacuo and purified by flash chromatography using hexanes:ethyl acetate (3:7) as eluent.

Fractions containing the desired product were collected and concentrated in vacuo to afford 3-(2,3-dihydroxypropyl)-1H-indol-4-yl acetate (1.31 g, 5.26 mmol, 74.4%).

The product was characterized by $^1$H NMR (400 MHz, acetone-D$_6$). The observed peaks on $^1$H NMR were δ 2.38 (s, 3H) 2.99 (dd, =14.35, 6.15 Hz, 1H) 3.44-3.65 (m, 4H) 3.84-3.96 (m, 1H) 6.73 (d, =7.52 Hz, 1H) 7.06 (t, =7.86 Hz, 1H) 7.18 (s, 1H) 7.28 (d, =8.20 Hz, 1H).

Example XV

The method shown in FIG. 20 was carried out. The reagents and products included a total volume of 200 mL, including 100 mL of tetrahydrofuran and 100 mL of water, with a reaction molarity of 100 mmolar at a temperature of 25° C. Details of the reagents are shown in Table 15A and Table 15B. Details of the products are shown in Table 15C and Table 15D.

TABLE 15A

Physical Properties of Reagents

| Reagent | Formula | MM (g/mol) |
|---|---|---|
| 3-allyl-1H-indol-4-yl acetate | $C_{13}H_{13}NO_2$ | 215.25 |
| potassium osmate dihydrate | $H_4K_2O_6Os$ | 368.45 |
| 4-methylmorpholine 4-oxide | $C_5H_{11}NO_2$ | 117.15 |

TABLE 15B

Relative Amounts of Reagents and Solvents

| Reagent | Eq | M (g) | mmol | Notes |
|---|---|---|---|---|
| 3-allyl-1H-indol-4-yl acetate | 1 | 8.53 g | 39.6 mmol | N/A |
| tetrahydrofuran | N/A | N/A | N/A | 70 mL |
| water | N/A | N/A | N/A | 70 mL |
| potassium osmate dihydrate | 0.05 | 0.73 g | 1.98 mmol | N/A |
| 4-methylmorpholine 4-oxide | 5 | 13.9 g | 198.0 mmol | N/A |

TABLE 15C

Physical Properties of Products

| Product | Formula | MM (g/mol) |
|---|---|---|
| 3-(2,3-dihydroxypropyl)-1H-indol-4-yl acetate | $C_{13}H_{15}NO_4$ | 249.27 |

TABLE 15D

Relative Amounts of Products

| Product | Theoretical | Actual | Yield |
|---|---|---|---|
| 3-(2,3-dihydroxypropyl)-1H-indol-4-yl acetate | 9.87 g | 4.11 g | 41.6% |

100 mL of tetrahydrofuran and 100 mL of water was added to a 300 mL round bottom flask containing 3-allyl-1H-indol-4-yl acetate (8.53 g, 39.6 mmol). Potassium Osmate (730 mg, 1.98 mmol) was added in one portion. 4-Methylmorpholine 4-oxide (13.9 g, 119 mmol) was added in one portion.

The reaction was stirred at 25° C. for 2 hours. Upon completion, the reaction was quenched with a saturated solution of sodium thiosulfate (20 mL). Charcoal (2.6 g, 30 Wt %) was added. The resultant mixture was stirred at room temperature for 30 min then filtered through a pad of Celite diatomaceous earth. The organic phase was separated and was further washed with an aqueous solution of hydrochloric acid (0.5M, 3×100 mL), saturated solution of sodium bicarbonate (100 mL) and water (3×100 mL). Note: It is important to remove all the inorganic salts through excess water washes. The aqueous solution should become clear at the end of the 3rd water wash. If not, wash with more water until the aqueous solution became clear.

The resulting organic extracts were concentrated under reduced pressure. The crude material was triturated in dichloromethane (100 mL) to afford the desired product, 3-(2,3-dihydroxypropyl)-1H-indol-4-yl acetate (4.11 g, 16.5 mmol, 41.6%) as a light gray powder.

The product was characterized by 1H NMR (400 MHz, acetone-D6). The observed peaks on 1H NMR were δ 2.38 (s, 3H) 2.99 (dd, =14.35, 6.15 Hz, 1H) 3.44-3.65 (m, 4H) 3.84-3.96 (m, 1H) 6.73 (d, =7.52 Hz, 1H) 7.06 (t, =7.86 Hz, 1H) 7.18 (s, 1H) 7.28 (d, =8.20 Hz, 1H).

Example XVI

The method shown in FIG. 20 was carried out. The reagents and products included a total volume of 220 mL, including 200 mL of 2-methyltetrahydrofuran and 20 mL of water, with a reaction molarity of 236 mmolar at a temperature of 25° C. Details of the reagents are shown in Table 16A and Table 16B. Details of the products are shown in Table 16C and Table 16D.

TABLE 16A

Physical Properties of Reagents

| Reagent | Formula | MM (g/mol) |
|---|---|---|
| 3-allyl-1H-indol-4-yl acetate | $C_{13}H_{13}NO_2$ | 215.25 |
| potassium osmate dihydrate | $H_4K_2O_6Os$ | 368.45 |
| 4-methylmorpholine 4-oxide | $C_5H_{11}NO_2$ | 117.15 |

TABLE 16B

Relative Amounts of Reagents and Solvents

| Reagent | Eq | M (g) | mmol | Notes |
|---|---|---|---|---|
| 3-allyl-1H-indol-4-yl acetate | 1 | 12.0 g | 55.8 mmol | N/A |
| 2-methyl-tetrahydrofuran | N/A | N/A | N/A | 200 mL |
| water | N/A | N/A | N/A | 20 mL |
| 2,6-lutidine | 2.5 | 14.9 g | 139.4 mmol | Density 0.925 g/mL Volume 16.1 mL |
| potassium osmate dihydrate | 0.025 | 0.514 g | 1.39 mmol | N/A |
| 4-methylmorpholine 4-oxide | 2.5 | 16.3 g | 139.4 mmol | N/A |

TABLE 16C

Physical Properties of Products

| Product | Formula | MM (g/mol) |
|---|---|---|
| 3-(2,3-dihydroxypropyl)-1H-indol-4-yl acetate | $C_{13}H_{15}NO_4$ | 249.27 |

TABLE 16D

Relative Amounts of Products

| Product | Theoretical | Actual | Yield |
|---|---|---|---|
| 3-(2,3-dihydroxypropyl)-1H-indol-4-yl acetate | 13.9 g | 4.42 | 31.8% |

200 mL of 2-methyltetrahydrofuran and 20 mL of water was added to a 500 mL Erlenmeyer flask containing crude 3-allyl-1H-indol-4-yl acetate (12.0 g, 55.8 mmol). 2,6-lutidine (16.1 mL, 139.4 mmol) was added in one portion (lutidine not shown in FIG. 20). Potassium Osmate (519 mg, 1.39 mmol) was added in one portion. 4-Methylmorpholine 4-oxide (16.3 g, 139.4 mmol) was added in one portion.

The reaction was stirred vigorously at 25° C. for 3 hours. Upon completion, the reaction was quenched with a saturated solution of sodium thiosulfate (60 mL). Charcoal (4 g, 33 Wt %) was added. The resultant mixture was stirred at room temperature for 30 min then filtered through a pad of Celite diatomaceous earth. The organic phase was separated and was further washed with an aqueous solution of hydrochloric acid (0.5M, 3×300 mL), saturated solution of sodium bicarbonate (300 mL) and brine (200 mL)

The resulting organic extracts were concentrated under reduced pressure. The crude material was dissolved in 1,2-dichloromethane (25 mL) and precipitated with di-isopropyl ether (100 mL) to afford the desired product, 3-(2,3-dihydroxypropyl)-1H-indol-4-yl acetate (4.42 g, 17.7 mmol, 31.8%), as a light gray powder.

The product was characterized by 1H NMR (400 MHz, acetone-D6). The observed peaks on 1H NMR were δ 2.38 (s, 3H) 2.99 (dd, =14.35, 6.15 Hz, 1H) 3.44-3.65 (m, 4H) 3.84-3.96 (m, 1H) 6.73 (d, =7.52 Hz, 1H) 7.06 (t, =7.86 Hz, 1H) 7.18 (s, 1H) 7.28 (d, =8.20 Hz, 1H).

Example XVII

The method shown in FIG. 21 was carried out. The reagents and products included a total volume of 1246 mL, including 1100 mL of 2-methyltetrahydrofuran and 60 mL of water, with a reaction molarity of 334 mmolar at a temperature of 25° C. Details of the reagents are shown in Table 17A and Table 17B. Details of the products are shown in Table 17C and Table 17D.

TABLE 17A

Physical Properties of Reagents

| Reagent | Formula | MM (g/mol) |
|---|---|---|
| 4-acetyl-indole | $C_{10}H_9NO_2$ | 175.2 |
| allyl alcohol | $C_3H_6O$ | 58.1 |
| triethyl borane | $C_6H_{15}B$ | 98.0 |
| tetra(triphenylphosphine)palladium | $C_{27}H_{60}P_4Pd$ | 1155.6 |
| 3-allyl-1H-indol-4-yl acetate | $C_{13}H_{13}NO_2$ | 215.25 |
| 2,6-lutidine | $C_7H_9N$ | 107.2 |
| potassium osmate dihydrate | $H_4K_2O_6Os$ | 368.45 |
| 4-methylmorpholine 4-oxide | $C_5H_{11}NO_2$ | 117.15 |

TABLE 17B

Relative Amounts of Reagents and Solvents

| Reagent | Eq | M (g) | mmol | Notes |
|---|---|---|---|---|
| 4-acetyl-indole | 1 | 29.3 | 167 | N/A |
| 2-methyl-tetrahydrofuran | N/A | N/A | N/A | 500 mL |
| allyl alcohol | 1.5 | N/A | 201 | 13.6 mL |
| triethyl borane | 0.3 | N/A | 50.2 | 1.0M in THF Volume 50.2 mL |
| tetra(triphenylphosphine)palladium | 0.03 | 5.80 g | 5.02 | N/A |
| 2-methyl-tetrahydrofuran | N/A | N/A | N/A | 600 mL |
| water | N/A | N/A | N/A | 60 mL |
| 3-allyl-1H-indol-4-yl acetate | N/A | N/A | N/A | N/A |
| 2,6-lutidine | 2.5 | 44.8 g | 418 mmol | Density 0.925 g/mL Volume 48.4 mL |
| potassium osmate dihydrate | 0.025 | 1.54 g | 4.18 mmol | N/A |
| 4-methylmorpholine 4-oxide | 2.5 | 56.5 g | 418 mmol | N/A |

TABLE 17C

Physical Properties of Products

| Product | Formula | MM (g/mol) |
|---|---|---|
| 3-(2,3-dihydroxypropyl)-1H-indol-4-yl acetate | $C_{13}H_{15}NO_4$ | 249.27 |

TABLE 17D

Relative Amounts of Products

| Product | Theoretical | Actual | Yield |
|---|---|---|---|
| 3-(2,3-dihydroxypropyl)-1H-indol-4-yl acetate | 41.7 g | 9.83 g | 23.6% |

500 mL of 2-methyltetrahydrofuran was added to a 1000 mL round-bottom flask and sparged with argon. While sparging, 1H-indol-4-yl acetate (29.3 g, 1 Eq, 167.1 mmol) and allyl alcohol (13.6 mL, 1.5 Eq, 201 mmol) were added to the flask. Sparging with argon was continued for 30 minutes. After sparging, triethylborane (1.0 M in tetrahydrofuran, 50.2 mL, 0.3 Eq, 50.2 mmol) and tetrakis(triphenylphosphine) palladium (5.81 g, 0.03 Eq, 5.02 mmol) were sequentially added to the reaction.

The reaction was heated at 60° C. and stirred for 2 hours under an argon atmosphere. Upon completion, the crude reaction mixture was washed with water (3×200 mL). The organics were dried over anhydrous sodium sulfate (30 g), concentrated under reduced pressure and dried under vacuum for 2 h.

600 mL of 2-methyltetrahydrofuran and 60 mL of water was added to a 1000 mL Erlenmeyer flask containing crude 3-allyl-1H-indol-4-yl acetate telescoped from the allylation reaction. 2,6-lutidine (48.4 mL, 418 mmol) was added in one portion. Potassium Osmate (1.54 g, 4.18 mmol) was added in one portion. 4-Methylmorpholine 4-oxide (56.5 g, 418 mmol) was added in one portion.

The reaction was stirred vigorously at 25° C. for 3 hours. Upon completion, the reaction was quenched with a saturated solution of sodium thiosulfate (60 mL). Charcoal (10 g, 33 Wt %) was added. The resultant mixture was stirred at room temperature for 30 min then filtered through a pad of Celite diatomaceous earth. The organic phase was separated and was further washed with an aqueous solution of hydrochloric acid (0.5M, 3×300 mL), saturated solution of sodium bicarbonate (300 mL) and brine (200 mL)

The resulting organic extracts were concentrated under reduced pressure. The crude material was dissolved in 1,2-dichloromethane (10 mL) and precipitated with di-isopropyl ether (80 mL) to afford the desired product, 3-(2,3-dihydroxypropyl)-1H-indol-4-yl acetate (9.83 g, 39.4 mmol, 23.6%), as a light gray powder.

The product was characterized by 1H NMR (400 MHz, acetone-D6). The observed peaks on 1H NMR were δ 2.38 (s, 3H) 2.99 (dd, =14.35, 6.15 Hz, 1H) 3.44-3.65 (m, 4H) 3.84-3.96 (m, 1H) 6.73 (d, =7.52 Hz, 1H) 7.06 (t, =7.86 Hz, 1H) 7.18 (s, 1H) 7.28 (d, =8.20 Hz, 1H).

Example XVIII

The method shown in FIG. 21 was carried out. The reagents and products included a total volume of 824 mL, including 750 mL of 2-methyltetrahydrofuran and 45 mL of water, with a reaction molarity of 250 mmolar at a temperature of 25° C. Details of the reagents are shown in Table 18A and Table 18B. Details of the products are shown in Table 18C and Table 18D.

TABLE 18A

Physical Properties of Reagents

| Reagent | Formula | MM (g/mol) |
|---|---|---|
| 4-acetyl-indole | $C_{10}H_9NO_2$ | 175.2 |
| allyl alcohol | $C_3H_6O$ | 58.1 |
| triethyl borane | $C_6H_{15}B$ | 98.0 |
| tetra(triphenylphosphine)palladium | $C_{27}H_{60}P_4Pd$ | 1155.6 |
| 3-allyl-1H-indol-4-yl acetate | $C_{13}H_{13}NO_2$ | 215.25 |
| 2,6-lutidine | $C_7H_9N$ | 107.2 |
| potassium osmate dihydrate | $H_4K_2O_6Os$ | 368.45 |
| 4-methylmorpholine 4-oxide | $C_5H_{11}NO_2$ | 117.15 |

TABLE 18B

Relative Amounts of Reagents and Solvents

| Reagent | Eq | M (g) | mmol | Notes |
|---|---|---|---|---|
| 4-acetyl-indole | 1 | 13.1 | 74.8 | N/A |
| 2-methyl-tetrahydrofuran | N/A | N/A | N/A | 300 mL |
| allyl alcohol | 1.5 | N/A | 89.7 | 6.10 mL 0.854 g/mL |
| triethyl borane | 0.3 | N/A | 22.4 | 1.0M in THF Volume 22.4 mL |
| tetra(triphenylphosphine)palladium | 0.03 | 2.59 g | 2.24 | N/A |
| 2-methyl-tetrahydrofuran | N/A | N/A | N/A | 450 mL |
| water | N/A | N/A | N/A | 45 mL |
| 3-allyl-1H-indol-4-yl acetate | N/A | N/A | N/A | N/A |
| 2,6-lutidine | 2.5 | 20.1 g | 187 mmol | Density 0.925 g/mL Volume 21.7 mL |
| potassium osmate dihydrate | 0.025 | 689 mg | 1.87 mmol | N/A |
| 4-methylmorpholine 4-oxide | 2.5 | 25.3 g | 187 mmol | N/A |

TABLE 18C

Physical Properties of Products

| Product | Formula | MM (g/mol) |
|---|---|---|
| 3-(2,3-dihydroxypropyl)-1H-indol-4-yl acetate | $C_{13}H_{15}NO_4$ | 249.27 |

TABLE 18D

Relative Amounts of Products

| Product | Theoretical | Actual | Yield |
|---|---|---|---|
| 3-(2,3-dihydroxypropyl)-1H-indol-4-yl acetate | 18.6 g | 2.12 g | 11.4% |

300 mL of 2-methyltetrahydrofuran was added to a 500 mL round-bottom flask and sparged with argon. While sparging, 1H-indol-4-yl acetate (13.1 g, 1 Eq, 74.8 mmol) and allyl alcohol (6.1 mL, 1.5 Eq, 89.7 mmol) were added to the flask. Sparging with argon was continued for 30 minutes. After sparging, triethylborane (1.0 M in tetrahydrofuran, 22.4 mL, 0.3 Eq, 22.4 mmol) and tetrakis(triphenylphosphine) palladium (2.59 g, 0.03 Eq, 2.24 mmol) were sequentially added to the reaction.

The reaction was heated at 60° C. and stirred for 2 hours under an argon atmosphere. Upon completion, the crude reaction mixture was washed with water (3×100 mL). The organics were dried over anhydrous sodium sulfate (20 g), concentrated under reduced pressure and dried under vacuum for 2 h.

450 mL of 2-methyltetrahydrofuran and 45 mL of water was added to a 1000 mL Erlenmeyer flask containing crude 3-allyl-1H-indol-4-yl acetate telescoped from the allylation reaction. 2,6-lutidine (21.7 mL, 187 mmol) was added in one portion. Potassium Osmate (689 mg, 1.87 mmol) was added in one portion. 4-Methylmorpholine 4-oxide (25.3 g, 187 mmol) was added in one portion.

The reaction was stirred at 25° C. for 3 hours. Upon completion, the reaction was quenched with a saturated solution of sodium thiosulfate (45 mL). Charcoal (4 g, 30 Wt %) was added. The resultant mixture was stirred at room temperature for 30 min then filtered through a pad of Celite diatomaceous earth. The organic phase was separated and was further washed with an aqueous solution of hydrochloric acid (0.5M, 3×300 mL), saturated solution of sodium bicarbonate (300 mL) and brine (200 mL)

The resulting organic extracts were dried over anhydrous sodium sulfate (30 g) and concentrated under reduced pressure. The crude material was crystallized in hot toluene (770 mL) to afford the desired product, 3-(2,3-dihydroxypropyl)-1H-indol-4-yl acetate (2.12 g, 8.50 mmol, 11.4%), as a light gray powder.

The product was characterized by 1H NMR (400 MHz, acetone-D6). The observed peaks on 1H NMR were δ 2.38 (s, 3H) 2.99 (dd, =14.35, 6.15 Hz, 1H) 3.44-3.65 (m, 4H) 3.84-3.96 (m, 1H) 6.73 (d, =7.52 Hz, 1H) 7.06 (t, =7.86 Hz, 1H) 7.18 (s, 1H) 7.28 (d, =8.20 Hz, 1H).

Figure 34:
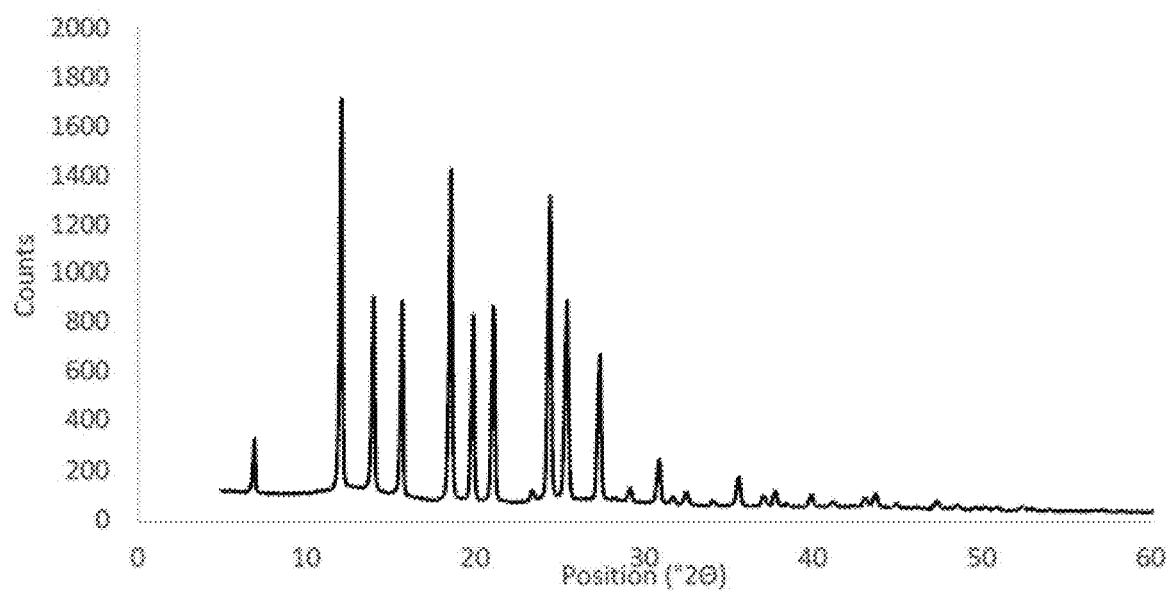
FIG. 34 shows the XRD pattern of 3-(2,3-dihydroxypropyl)-1H-indol-4-yl acetate crystals grown from toluene.

An XRD pattern was obtained for 3-(2,3-dihydroxypropyl)-1H-indol-4-yl acetate crystals grown from toluene. The XRD pattern is shown in FIG. 34.

Example XIX

The method shown in FIG. 21 was carried out. The reagents and products of the first step included a total volume of 337 mL, including 300 mL of 2-methyltetrahydrofuran, with a reaction molarity of 288 mmolar at a temperature of 25° C. The reagents and products of the second step included a total volume of 523 mL, including 450 mL of 2-methyltetrahydrofuran and 45 mL of water, with a reaction molarity of 185 mmolar at a temperature of 25° C. Details of the reagents are shown in Table 19A and Table 19B. Details of the products are shown in Table 19C and Table 19D.

TABLE 19A

Physical Properties of Reagents

| Reagent | Formula | MM (g/mol) |
|---|---|---|
| 4-acetyl-indole | $C_{10}H_9NO_2$ | 175.2 |
| allyl alcohol | $C_3H_6O$ | 58.1 |
| triethyl borane | $C_6H_{15}B$ | 98.0 |
| tetra(triphenylphosphine)palladium | $C_{27}H_{60}P_4Pd$ | 1155.6 |
| 3-allyl-1H-indol-4-yl acetate | $C_{13}H_{13}NO_2$ | 215.25 |
| 2,6-lutidine | $C_7H_9N$ | 107.2 |
| potassium osmate dihydrate | $H_4K_2O_6Os$ | 368.45 |
| 4-methylmorpholine 4-oxide | $C_5H_{11}NO_2$ | 117.15 |

TABLE 19B

Relative Amounts of Reagents and Solvents

| Reagent | Eq | M (g) | mmol | Notes |
|---|---|---|---|---|
| 4-acetyl-indole | 1 | 17.1 | 97.4 | N/A |
| 2-methyl-tetrahydrofuran | N/A | N/A | N/A | 300 mL |
| allyl alcohol | 1.5 | N/A | 117 | 7.95 mL 0.854 g/mL |
| triethyl borane | 0.3 | N/A | 29.2 | 1.0M in THF Volume 29.2 mL |
| tetra(triphenylphosphine)palladium | 0.03 | 3.38 g | 2.92 | N/A |
| 2-methyl-tetrahydrofuran | N/A | N/A | N/A | 450 mL |
| water | N/A | N/A | N/A | 45 mL |
| 3-allyl-1H-indol-4-yl acetate | N/A | N/A | N/A | N/A |
| 2,6-lutidine | 2.5 | 26.1 g | 243 mmol | Density 0.925 g/mL Volume 28.2 mL |
| potassium osmate dihydrate | 0.025 | 897 mg | 2.43 mmol | N/A |
| 4-methylmorpholine 4-oxide | 2.5 | 32.9 g | 243 mmol | N/A |

TABLE 19C

Physical Properties of Products

| Product | Formula | MM (g/mol) |
|---|---|---|
| 3-(2,3-dihydroxypropyl)-1H-indol-4-yl acetate | $C_{13}H_{15}NO_4$ | 249.27 |

TABLE 19D

Relative Amounts of Products

| Product | Theoretical | Actual | Yield |
|---|---|---|---|
| 3-(2,3-dihydroxypropyl)-1H-indol-4-yl acetate | 24.27 g | 2.41 g | 10% |

300 mL of 2-methyltetrahydrofuran was added to a 500 mL round-bottom flask and sparged with argon. While sparging, 1H-indol-4-yl acetate (17.1 g, 1 Eq, 97.4 mmol) and allyl alcohol (7.95 mL, 1.5 Eq, 117 mmol) were added to the flask. Sparging with argon was continued for 30 minutes. After sparging, triethylborane (1.0 M in tetrahydrofuran, 29.2 mL, 0.3 Eq, 29.2 mmol) and tetrakis(triphenylphosphine) palladium (3.38 g, 0.03 Eq, 2.92 mmol) were sequentially added to the reaction.

The reaction was heated at 60° C. and stirred for 2 hours under an argon atmosphere. Upon completion, the crude reaction mixture was washed with water (3×100 mL). The organics were dried over anhydrous sodium sulfate (20 g), concentrated under reduced pressure and dried under vacuum for 2 h.

450 mL of 2-methyltetrahydrofuran and 45 mL of water was added to a 1000 mL Erlenmeyer flask containing crude 3-allyl-1H-indol-4-yl acetate telescoped from the allylation reaction. 2,6-lutidine (28.2 mL, 243 mmol) was added in one portion. Potassium Osmate (897 mg, 2.43 mmol) was added in one portion. 4-Methylmorpholine 4-oxide (32.9 g, 243 mmol) was added in one portion.

The reaction was stirred at 25° C. for 3 hours. Upon completion, the reaction was quenched with a saturated solution of sodium thiosulfate (45 mL). Charcoal (6 g, 30 Wt %) was added. The resultant mixture was stirred at room temperature for 30 min then filtered through a pad of Celite diatomaceous earth. The organic phase was separated and was further washed with an aqueous solution of hydrochloric acid (0.5M, 3×300 mL), saturated solution of sodium bicarbonate (300 mL) and brine (200 mL)

The resulting organic extracts were dried over anhydrous sodium sulfate (30 g) and concentrated under reduced pressure. The crude material was crystallized in hot toluene (900 mL) to afford the desired product, 3-(2,3-dihydroxypropyl)-1H-indol-4-yl acetate (2.41 g, 9.68 mmol, 10%), as a light gray powder.

The filtrate from the crystallization can be treated with silica gel to afford a second crop of crystals. The filtrate was concentrated to dryness and then redissolved in 50 mL of methanol. To this solution was added 30 g of silica gel and the contents of the flask were then dried under reduced pressure. The dried contents of the flask was layered on top of 70 g of silica gel and then the silica mixture was rinsed with 400 ml of 1:1 ethyl acetate:hexanes. The product was then eluted with 700 ml of ethyl acetate. The ethyl acetate solution was concentrated to dryness and then the residue was recrystallized using 350 ml of toluene. The second crop of product, 3-(2,3-dihydroxypropyl)-1H-indol-4-yl acetate (1.60 g, 6.42 mmol), was isolated as a light gray powder.

The product was characterized by 1H NMR (400 MHz, acetone-D6). The observed peaks on 1H NMR were δ 2.38 (s, 3H) 2.99 (dd, =14.35, 6.15 Hz, 1H) 3.44-3.65 (m, 4H) 3.84-3.96 (m, 1H) 6.73 (d, =7.52 Hz, 1H) 7.06 (t, =7.86 Hz, 1H) 7.18 (s, 1H) 7.28 (d, =8.20 Hz, 1H).

Example XX

The method shown in FIG. 22 was carried out. The reagents and products included a total volume of 10 mL, including 2.5 mL of tetrahydrofuran and 2.5 mL of water for cleavage (step 1 in FIG. 22), and 5 mL of 1,2-dichloroethane for reductive amination (step 1 in FIG. 22), with a reaction molarity of 25 mmolar at a temperature of 25° C. Details of the reagents are shown in Table 20A and Table 20B. Details of the products are shown in Table 20C and Table 20D.

TABLE 20A

Physical Properties of Reagents

| Reagent | Formula | MM (g/mol) |
|---|---|---|
| 3-(2,3-dihydroxypropyl)-1H-indol-4-yl acetate | $C_{13}H_{15}NO_4$ | 249.27 |
| sodium periodate | $NaIO_4$ | 213.89 |
| pyrrolidine | $C_4H_9N$ | 71.12 |
| sodium triacetoxyhydroborate | $C_6H_{10}BNaO_6$ | 211.94 |

TABLE 20B

Relative Amounts of Reagents and Solvents

| Reagent | Eq | M (g) | mmol | Notes |
|---|---|---|---|---|
| 3-(2,3-dihydroxypropyl)-1H-indol-4-yl acetate | 1 | 62.3 mg | 250 μmol | N/A |
| tetrahydrofuran | N/A | N/A | N/A | 2.5 mL |
| water | N/A | N/A | N/A | 2.5 mL |
| sodium periodate | 1.5 | 80.2 mg | 375 μmol | N/A |
| 1,2-dichloroethane | N/A | N/A | N/A | 5.0 mL |
| pyrrolidine | 1 | 17.8 mg | 250 μmol | 20.5 mL |
| sodium triacetoxyhydroborate | 1.5 | 79.5 mg | 375 μmol | N/A |

TABLE 20C

Physical Properties of Products

| Product | Formula | MM (g/mol) |
|---|---|---|
| 3-(2-(pyrrolidin-1-yl)ethyl)-1H-indol-4-yl acetate | $C_{16}H_{20}N_2O_2$ | 272.35 |

TABLE 20D

Relative Amounts of Products

| Product | Theoretical | Actual | Yield |
|---|---|---|---|
| 3-(2-(pyrrolidin-1-yl)ethyl)-1H-indol-4-yl acetate | 68.1 mg | N/A | N/A |

2.5 mL of tetrahydrofuran and 2.5 mL of water was added to a 20 mL vial containing 3-(2,3-dihydroxypropyl)-1H-indol-4-yl acetate (62.3 mg, 250 μmol). Sodium periodate (80.2 mg, 375 μmol) was added in one portion.

The reaction was stirred at 25° C. for 90 minutes. Upon completion, the reaction was quenched with a saturated solution of sodium thiosulfate (5 mL). The organic phase was separated and the aqueous phase was extracted with ethyl acetate (3×5 mL). The combine organic extracts were concentrated in vacuo and was used in the subsequent reaction without additional purification.

5 mL of 1,2-dichloroethane was added to a 20 mL vial containing crude 3-(2-oxoethyl)-1H-indol-4-yl acetate. Pyrrolidine (20.5 μL, 250 μmol) was added in one portion. Sodium triacetoxyhydroborate (79.5 mg, 375 μmol) was added in one portion.

The reaction was stirred at 25° C. for 2 hours. Upon completion, the reaction was quenched with an aqueous solution of sodium hydroxide (1.0N, 5 mL). The organic phase was separated and the aqueous phase was extracted with dichloromethane (3×10 mL). The combine organic extracts were concentrated in vacuo to afford 3-(2-(pyrrolidin-1-yl)ethyl)-1H-indol-4-yl acetate.

The crude material was used in the subsequent reaction without further purification.

Example XXI

The method shown in FIG. 22 was carried out. The reagents and products included a total volume of 10 mL, including 5 mL of tetrahydrofuran and 5 mL of water, with a reaction molarity of 99 mmolar at a temperature of 25° C. Details of the reagents are shown in Table 21A and Table 21B. Details of the products are shown in Table 21C and Table 21D.

TABLE 21A

Physical Properties of Reagents

| Reagent | Formula | MM (g/mol) |
|---|---|---|
| 3-(2,3-dihydroxypropyl)-1H-indol-4-yl acetate | $C_{13}H_{15}NO_4$ | 249.27 |
| sodium periodate | $NaIO_4$ | 213.89 |
| pyrrolidine | $C_4H_9N$ | 71.12 |
| sodium triacetoxyhydroborate | $C_6H_{10}BNaO_6$ | 211.94 |

TABLE 21B

Relative Amounts of Reagents and Solvents

| Reagent | Eq | M (g) | mmol | Notes |
|---|---|---|---|---|
| 3-(2,3-dihydroxypropyl)-1H-indol-4-yl acetate | 1 | 249 mg | 1.00 mmol | N/A |
| tetrahydrofuran | N/A | N/A | N/A | 5 mL |
| water | N/A | N/A | N/A | 5 mL |
| sodium periodate | 1.5 | 321 mg | 1.50 mmol | N/A |
| pyrrolidine | 1 | 71.1 mg | 1.00 mmol | 82.1 ml |
| sodium triacetoxyhydroborate | 1.5 | 318 mg | 1.50 mmol | N/A |

TABLE 21C

Physical Properties of Products

| Product | Formula | MM (g/mol) |
|---|---|---|
| 3-(2-(pyrrolidin-1-yl)ethyl)-1H-indol-4-yl acetate | $C_{16}H_{20}N_2O_2$ | 272.35 |

TABLE 21D

Relative Amounts of Products

| Product | Theoretical | Actual | Yield |
|---|---|---|---|
| 3-(2-(pyrrolidin-1-yl)ethyl)-1H-indol-4-yl acetate | 272 mg | N/A | N/A |

5 mL of THF and 5 mL of water was added to a 20 mL vial containing 3-(2,3-dihydroxypropyl)-1H-indol-4-yl acetate (249 mg, 1.00 mmol). Sodium periodate (321 mg, 1.50 mmol) was added in one portion.

The reaction was stirred at 25° C. for 1 h. Pyrrolidine (80.1 ml, 1.00 mmol) was added in one portion. Sodium triacetoxyhydroborate (318 mg, 1.5 mmol) was added in one portion.

The reaction was stirred at 25° C. for another 2 hours. Upon completion, the reaction was quenched with an aqueous solution of sodium hydroxide (1.0N, 5 mL). The organic phase was separated and the aqueous phase was extracted with dichloromethane (3×10 mL). The combine organic extracts were concentrated in vacuo to afford 3-(2-(pyrrolidin-1-yl)ethyl)-1H-indol-4-yl acetate.

The crude material was used in the subsequent reaction without further purification. The subsequent reaction is detailed in Example XXV.

Example XXII

The method shown in FIG. 22 was carried out. The reagents and products included a total volume of 31 mL, including 20 mL of 1,2-dichloroethane and 10 mL of water, with a reaction molarity of 130 mmolar at a temperature of 25° C. Details of the reagents are shown in Table 22A and Table 22B. Details of the products are shown in Table 22C and Table 22D.

TABLE 22A

Physical Properties of Reagents

| Reagent | Formula | MM (g/mol) |
|---|---|---|
| 3-(2,3-dihydroxypropyl)-1H-indol-4-yl acetate | $C_{13}H_{15}NO_4$ | 249.27 |
| sodium periodate | $NaIO_4$ | 213.89 |
| pyrrolidine | $C_4H_9N$ | 71.12 |
| sodium triacetoxyhydroborate | $C_6H_{10}BNaO_6$ | 211.94 |

TABLE 22B

Relative Amounts of Reagents and Solvents

| Reagent | Eq | M (g) | mmol | Notes |
|---|---|---|---|---|
| 3-(2,3-dihydroxypropyl)-1H-indol-4-yl acetate | 1 | 62.3 mg | 4.01 mmol | N/A |
| 1,2-dichloroethane | N/A | N/A | N/A | 10 mL |
| water | N/A | N/A | N/A | 10 mL |
| sodium periodate | 1.5 | 1.29 mg | 6.02 mmol | N/A |
| 1,2-dichloroethane | N/A | N/A | N/A | 5.0 mL |
| pyrrolidine | 3 | N/A | 12.0 mmol | 0.988 mL Density 0.866 g/mL |
| sodium triacetoxyhydroborate | 5 | 4.25 g | 20.1 mmol | N/A |

TABLE 22C

Physical Properties of Products

| Product | Formula | MM (g/mol) |
|---|---|---|
| 3-(2-(pyrrolidin-1-yl)ethyl)-1H-indol-4-yl acetate | $C_{16}H_{20}N_2O_2$ | 272.35 |

TABLE 22D

Relative Amounts of Products

| Product | Theoretical | Actual | Yield |
|---|---|---|---|
| 3-(2-(pyrrolidin-1-yl)ethyl)-1H-indol-4-yl acetate | 1.09 g | 487 mg | 44.6% |

10 mL of 1,2-dichloroethane and 10 mL of water was added to a 100 mL round bottom flask containing 3-(2,3-dihydroxypropyl)-1H-indol-4-yl acetate (1.00 g, 4.01 mmol). Sodium periodate (1.29 g, 6.02 mmol) was added in one portion.

The reaction was stirred at 25° C. for 30 min and phases were separated. The organic phase was washed with water (3×20 mL).

A separate 100 mL round bottom flask was charged with pyrrolidine (0.988 ml, 12.0 mmol) and sodium triacetoxyhydroborate (4.15 g, 20.1 mmol) in 1,2-dichloroethane (10 mL).

The crude aldehyde solution in 1,2-dichloroethane (~10 mL) was added dropwise over 5 minutes with vigorous stirring.

The reaction was stirred at 25° C. for another 30 minutes. The resulting reaction mixture was filtered through a pad of silica gel (20 g). The filter cake was washed with tetrahydrofuran (100 mL). The combined organic extracts were concentrated under reduced pressure and purified by flash chromatography using dichloromethane:tetrahydrofuran (15:85) as eluent to afford the desired product, 3-(2-(pyrrolidin-1-yl)ethyl)-1H-indol-4-ol (487 mg, 1.78 mmol, 44.6%) as a dark gray oil.

The product was characterized by 1H NMR (400 MHz, dichloromethane-D2). The observed peaks on 1H NMR were δ 1.87 (m, 4H) 2.38 (s, 3H) 2.85 (m, 4H) 2.89-2.97 (m, 2H) 2.98-3.06 (m, 2H) 6.74 (dd, J=7.63, 0.61 Hz, 1H) 6.87 (s, 1H) 7.08 (t, J=7.93 Hz, 1H) 7.23 (dd, J=8.24, 0.92 Hz, 1H) 9.63 (br. s., 1H).

Example XXIII

The method shown in FIG. 23 was carried out. The reagents and products included a total volume of 31 mL, including 20 mL of 1,2-dichloroethane and 10 mL of water, with a reaction molarity of 130 mmolar at a temperature of 25° C. Details of the reagents are shown in Table 23A and Table 23B. Details of the products are shown in Table 23C and Table 23D.

TABLE 23A

Physical Properties of Reagents

| Reagent | Formula | MM (g/mol) |
|---|---|---|
| 3-(2,3-dihydroxypropyl)-1H-indol-4-yl acetate | $C_{13}H_{15}NO_4$ | 249.27 |
| sodium periodate | $NaIO_4$ | 213.89 |
| pyrrolidine | $C_4H_9N$ | 71.12 |
| sodium triacetoxyhydroborate | $C_6H_{10}BNaO_6$ | 211.94 |

TABLE 23B

Relative Amounts of Reagents and Solvents

| Reagent | Eq | M (g) | mmol | Notes |
|---|---|---|---|---|
| 3-(2,3-dihydroxypropyl)-1H-indol-4-yl acetate | 1 | 1.00 g | 4.01 mmol | N/A |
| 1,2-dichloroethane | N/A | N/A | N/A | 10 mL |
| water | N/A | N/A | N/A | 10 mL |
| sodium periodate | 1.5 | 1.29 g | 6.02 mmol | N/A |
| 1,2-dichloroethane | N/A | N/A | N/A | 10 mL |
| pyrrolidine | 3 | N/A | 12.0 mmol | 0.988 mL Density 0.866 g/mL |
| sodium triacetoxyhydroborate | 5 | 4.25 g | 20.1 mmol | N/A |

TABLE 23C

Physical Properties of Products

| Product | Formula | MM (g/mol) |
|---|---|---|
| 3-(2-(pyrrolidin-1-yl)ethyl)-1H-indol-4-ol | $C_{14}H_{18}N_2O$ | 230.31 |

TABLE 23D

Relative Amounts of Products

| Product | Theoretical | Actual | Yield |
|---|---|---|---|
| 3-(2-(pyrrolidin-1-yl)ethyl)-1H-indol-4-yl acetate | 924 mg | 573 mg | 62.0% |

10 mL of 1,2-dichloroethane and 10 mL of water was added to a 100 mL round bottom flask containing 3-(2,3-dihydroxypropyl)-1H-indol-4-yl acetate (1.00 g, 4.01 mmol). Sodium periodate (1.29 g, 6.02 mmol) was added in one portion.

The reaction was stirred at 25° C. for 30 min and phases were separated. The organic phase was washed with water (3×20 mL).

A separate 100 mL round bottom flask was charged with pyrrolidine (0.988 ml, 12.0 mmol) and sodium triacetoxyhydroborate (4.15 g, 20.1 mmol) in 1,2-dichloroethane (10 mL).

The crude aldehyde solution in 1,2-dichloroethane (~10 mL) was added dropwise over 5 minutes with vigorous stirring.

The reaction was stirred at 25° C. for another 30 minutes. The resulting reaction mixture was filtered through a pad of Celite diatomaceous earth. The filter cake was washed with 1,2-dichloroethane (10 mL). The combined organic extracts were heated at 45° C. while stirring to promote deacylation.

After 2 hours, the crude mixture was concentrated under reduced pressure and deposited on silica gel (10 g). The silica gel containing the crude mixture was flushed with dichloromethane (50 mL) followed by dichloromethane:methanol (9:1, 50 mL)

The dichloromethane eluent was discarded and the dichloromethane:methanol eluent was concentrated under reduced pressure to afford the desired product, 3-(2-(pyrrolidin-1-yl)ethyl)-1H-indol-4-ol (573 mg, 2.50 mmol, 62.0%) as a dark gray oil.

The product was characterized by 1H NMR (600 MHz, methanol-$D_4$). The observed peaks on 1H NMR were δ 2.03-2.07 (m, 4H) 3.27 (t, J=7.52 Hz, 2H) 3.33 (m, 5H) 3.49 (t, J=7.52 Hz, 2H) 6.39 (d, J=8.05 Hz, 1H) 6.86 (d, J=8.07 Hz, 1H) 6.91 (dt, J=7.89, 3.76 Hz, 1H) 7.01 (s, 1H).

Example XXIV

The method shown in FIG. 24 was carried out. The reagents and products included a total volume of 480 mL, including 360 mL of 1,2-dichloroethane and 120 mL of water, with a reaction molarity of 100 mmolar at a temperature of 25° C. Details of the reagents are shown in Table 24A and Table 24B. Details of the products are shown in Table 24C and Table 24D.

TABLE 24A

Physical Properties of Reagents

| Reagent | Formula | MM (g/mol) |
|---|---|---|
| 3-(2,3-dihydroxypropyl)-1H-indol-4-yl acetate | $C_{13}H_{15}NO_4$ | 249.27 |
| sodium periodate | $NaIO_4$ | 213.89 |
| pyrrolidine | $C_4H_9N$ | 71.12 |
| sodium triacetoxyhydroborate | $C_6H_{10}BNaO_6$ | 211.94 |

TABLE 24B

Relative Amounts of Reagents and Solvents

| Reagent | Eq | M (g) | mmol | Notes |
|---|---|---|---|---|
| 3-(2,3-dihydroxypropyl)-1H-indol-4-yl acetate | 1 | 6.33 g | 25.4 mmol | N/A |
| 1,2-dichloroethane | N/A | N/A | N/A | 120 mL |
| water | N/A | N/A | N/A | 120 mL |
| sodium periodate | 1.5 | 8.15 g | 38.1 mmol | N/A |
| 1,2-dichloroethane | N/A | N/A | N/A | 240 mL |
| pyrrolidine | 3 | N/A | 76.2 mmol | 6.26 mL Density 0.866 g/mL |
| sodium triacetoxyhydroborate | 5 | 26.8 g | 127 mmol | N/A |

TABLE 24C

Physical Properties of Products

| Product | Formula | MM (g/mol) |
|---|---|---|
| 3-(2-(pyrrolidin-1-yl)ethyl)-1H-indol-4-yl acetate | $C_{16}H_{20}N_2O_2$ | 272.35 |
| 3-(2-(pyrrolidin-1-yl)ethyl)-1H-indol-4-ol | $C_{14}H_{18}N_2O$ | 230.31 |

TABLE 24D

Relative Amounts of Products

| Product | Theoretical | Actual | Yield |
|---|---|---|---|
| 3-(2-(pyrrolidin-1-yl)ethyl)-1H-indol-4-yl acetate | 6.92 g | 2.40 g | 35.0% |
| 3-(2-(pyrrolidin-1-yl)ethyl)-1H-indol-4-ol | 5.85 g | 2.39 g | 40.9% |

120 mL of 1,2-dichloroethane and 120 mL of water was added to a 500 mL round bottom flask containing 3-(2,3-dihydroxypropyl)-1H-indol-4-yl acetate (6.33 g, 25.4 mmol). Sodium periodate (8.15 g, 38.1 mmol) was added in one portion.

The reaction was stirred at 25° C. for 30 min and the phases were separated. The organic phase was washed with water (3×100 mL).

A separate 1 L Erlenmeyer flask was charged with pyrrolidine (6.26 ml, 76.2 mmol) and sodium triacetoxyhydroborate (26.9 g, 127 mmol) in 1,2-dichloroethane (240 mL).

The crude aldehyde solution in 1,2-dichloroethane (~120 mL) was added dropwise over 5 minutes with vigorous stirring.

The reaction was stirred at 25° C. for another 30 minutes. The resulting reaction mixture was filtered through a pad of Celite diatomaceous earth. The filter cake was washed with 1,2-dichloroethane (100 mL). The combined organic extracts were concentrated under reduced pressure and deposited on silica gel (60 g). The silica gel containing the crude mixture was flushed with dichloromethane (500 mL) followed by dichloromethane:methanol (9:1, 1 L)

The dichloromethane eluent was discarded and the dichloromethane:methanol eluent was concentrated under reduced pressure to afford 3-(2-(pyrrolidin-1-yl)ethyl)-1H-indol-4-yl acetate (2.40 g, 8.81 mmol, 35%) and 3-(2-(pyrrolidin-1-yl)ethyl)-1H-indol-4-ol (2.39 g, 10.4 mmol, 40.9%) in a mixture as a dark gray oil.

Example XXV

The method shown in FIG. 25 was carried out. The reagents and products included a total volume of 20 mL, including 20 mL of methanol, with a reaction molarity of 79 mmolar at a temperature of 25° C. Details of the reagents are shown in Table 25A and Table 25B. Details of the products are shown in Table 25C and Table 25D.

TABLE 25A

Physical Properties of Products

| Reagent | Formula | MM (g/mol) |
|---|---|---|
| 3-(2-(pyrrolidin-1-yl)ethyl)-1H-indol-4-yl acetate | $C_{16}H_{20}N_2O_2$ | 272.35 |
| 3-(2-(pyrrolidin-1-yl)ethyl)-1H-indol-4-ol | $C_{14}H_{18}N_2O$ | 230.31 |
| sodium borohydride | $NaBH_4$ | 37.8 |

TABLE 25B

Relative Amounts of Reagents and Solvents

| Reagent | Eq | M (g) | mmol | Notes |
|---|---|---|---|---|
| 3-(2-(pyrrolidin-1-yl)ethyl)-1H-indol-4-yl acetate | 1 | 423 mg | 1.58 | N/A |
| 3-(2-(pyrrolidin-1-yl)ethyl)-1H-indol-4-ol | 1 | 423 mg | 1.85 | N/A |
| sodium borohydride | 1.2 | 144 mg | 3.80 | N/A |
| methanol | N/A | N/A | N/A | 20 mL |

TABLE 23C

Physical Properties of Products

| Product | Formula | MM (g/mol) |
|---|---|---|
| 3-(2-(pyrrolidin-1-yl)ethyl)-1H-indol-4-ol | $C_{14}H_{18}N_2O$ | 230.31 |

TABLE 23D

Relative Amounts of Products

| Product | Theoretical | Actual | Yield |
|---|---|---|---|
| 3-(2-(pyrrolidin-1-yl)ethyl)-1H-indol-4-yl acetate | 730 mg | 487 mg | 66.7% |

Methanol (20 mL) was added to a 100 mL round bottom flask containing a mixture of 3-(2-(pyrrolidin-1-yl)ethyl)-1H-indol-4-yl acetate and 3-(2-(pyrrolidin-1-yl)ethyl)-1H-indol-4-ol (II). Sodium borohydride (144 mg, 1.2 Eq, 3.80 mmol) was added in one portion. CAUTION: The addition of sodium borohydride is exothermic and generates gas. The reaction mixture was allowed to stir at room temperature for 18 hours.

The resulting reaction mixture was concentrated to dryness under reduced pressure. The resulting crude solid was dissolved in dichloromethane:methanol (9:1, 20 mL) and filtered through a pad of silica gel (50 g). The filter cake was washed with additional dichloromethane:methanol (9:1, 200 mL). The combined organic solutions were concentrated under reduced pressure to afford the desired product, 0.3-(2-(pyrrolidin-1-yl)ethyl)-1H-indol-4-ol (487 mg, 2.11 mmol, 66.7%), as a brown solid.

The product was characterized by 1H NMR (600 MHz, methanol-D4) and The observed peaks on 1H NMR were δ 2.03-2.07 (m, 4H) 3.27 (t, J=7.52 Hz, 2H) 3.33 (m, 5H) 3.49 (t, J=7.52 Hz, 2H) 6.39 (d, J=8.05 Hz, 1H) 6.86 (d, J=8.07 Hz, 1H) 6.91 (dt, J=7.89, 3.76 Hz, 1H) 7.01 (s, 1H).

Example XXVI

The method shown in FIG. 26 was carried out. The reagents and products included a total volume of 480 mL, including 360 mL of 1,2-dichloroethane and 120 mL of water, with a reaction molarity of 100 mmolar at a temperature of 25° C. Details of the reagents are shown in Table 26A and Table 26B. Details of the products are shown in Table 26C and Table 26D.

TABLE 26A

Physical Properties of Reagents

| Reagent | Formula | MM (g/mol) |
|---|---|---|
| 3-(2,3-dihydroxypropyl)-1H-indol-4-yl acetate | $C_{13}H_{15}NO_4$ | 249.27 |
| sodium periodate | $NaIO_4$ | 213.89 |
| pyrrolidine | $C_4H_9N$ | 71.12 |
| sodium triacetoxyhydroborate | $C_6H_{10}BNaO_6$ | 211.94 |
| sodium borohydride | $NaBH_4$ | 37.8 |

TABLE 26B

Relative Amounts of Reagents and Solvents

| Reagent | Eq | M (g) | mmol | Notes |
|---|---|---|---|---|
| 3-(2,3-dihydroxypropyl)-1H-indol-4-yl acetate | 1 | 1.21 g | 4.85 mmol | N/A |
| 1,2-dichloroethane | N/A | N/A | N/A | 20 mL |
| water | N/A | N/A | N/A | 20 mL |
| sodium periodate | 1.5 | 1.56 g | 7.28 mmol | N/A |
| 1,2-dichloroethane | N/A | N/A | N/A | 40 mL |
| pyrrolidine | 3 | N/A | 14.6 mmol | 1.20 mL Density 0.866 g/mL |
| sodium triacetoxyhydroborate | 5 | 5.14 g | 24.3 mmol | N/A |
| sodium borohydride | 1.5 | 215 mg | 3.80 | N/A |
| methanol | N/A | N/A | N/A | N/A |

TABLE 26C

Physical Properties of Products

| Product | Formula | MM (g/mol) |
|---|---|---|
| 3-(2-(pyrrolidin-1-yl)ethyl)-1H-indol-4-ol | $C_{14}H_{18}N_2O$ | 230.31 |

TABLE 26D

| Relative Amounts of Products | | | |
|---|---|---|---|
| Product | Theoretical | Actual | Yield |
| 3-(2-(pyrrolidin-1-yl)ethyl)-1H-indol-4-yl acetate | 1.12 g | 288 mg | 25.8% |

20 mL of 1,2-dichloroethane and 20 mL of water was added to a 100 mL round bottom flask containing 3-(2,3-dihydroxypropyl)-1H-indol-4-yl acetate (1.21 g, 4.85 mmol). Sodium periodate (1.56 g, 7.28 mmol) was added in one portion.

The reaction was stirred at 25° C. for 30 min and the phases were separated. The organic phase was washed with water (3×40 mL).

A separate 250 mL Erlenmeyer flask was charged with pyrrolidine (1.20 ml, 14.6 mmol) and sodium triacetoxyhydroborate (5.14 g, 24.3 mmol) in 1,2-dichloroethane (40 mL).

The crude aldehyde solution in 1,2-dichloroethane (~20 mL) was added dropwise over 5 minutes with vigorous stirring.

The reaction was stirred at 25° C. for another 30 minutes. The resulting reaction mixture was filtered through a pad of Celite diatomaceous earth. The filter cake was washed with tetrahydrofuran (50 mL). The combined organic extracts were concentrated under reduced pressure and deposited on silica gel (60 g). The silica gel containing the crude mixture was flushed with tetrahydrofuran (200 mL) and concentrated under reduced pressure.

The crude material was then dissolved in methanol (20 mL). Sodium borohydride (144 mg, 3.80 mmol) was added in portions. CAUTION: The addition of sodium borohydride is exothermic and generates gas. The reaction mixture was allowed to stir at room temperature for 18 hours and at 50° C. for another 24 hours.

The resulting reaction mixture was concentrated to dryness under reduced pressure. The resulting crude solid was dissolved in tetrahydrofuran (20 mL) and filtered through a pad of silica gel (50 g). The filter cake was washed with additional tetrahydrofuran (300 mL). The combined organic solutions were concentrated under reduced pressure to afford the desired product, 0.3-(2-(pyrrolidin-1-yl)ethyl)-1H-indol-4-ol (288 mg, 1.25 mmol, 25.8%), as a brown solid.

The product was characterized by 1H NMR (600 MHz, methanol-D4). The observed peaks on 1H NMR were δ 2.03-2.07 (m, 4H) 3.27 (t, J=7.52 Hz, 2H) 3.33 (m, 5H) 3.49 (t, J=7.52 Hz, 2H) 6.39 (d, J=8.05 Hz, 1H) 6.86 (d, J=8.07 Hz, 1H) 6.91 (dt, J=7.89, 3.76 Hz, 1H) 7.01 (s, 1H).

Example XXVII

The method shown in FIG. 27 was carried out. The reagents and products included a total volume of 82.8 mL, including 25 mL of acetonitrile and 30 mL of water, with a reaction molarity of 110 mmolar at a temperature of 30° C. Details of the reagents are shown in Table 27A and Table 27B. Details of the products are shown in Table 27C and Table 27D.

TABLE 27A

| Physical Properties of Reagents | | |
|---|---|---|
| Reagent | Formula | MM (g/mol) |
| 1H-indole-4-ol | $C_8H_7NO$ | 133.15 |
| diisopropylethylamine | $C_8H_{19}N$ | 129.25 |

TABLE 27A-continued

| Physical Properties of Reagents | | |
|---|---|---|
| Reagent | Formula | MM (g/mol) |
| 1,1,-sulfonyldiimidazole | $C_6H_6N_4O_2S$ | 198.20 |
| potassium fluoride | KF | 58.10 |
| trifluoroacetic acid | $C_2HF_3O_2$ | 114.02 |

TABLE 27B

| Relative Amounts of Reagents and Solvents | | | | |
|---|---|---|---|---|
| Reagent | Eq | M (g) | mmol | Notes |
| 1H-indole-4-ol | 1 | 1.2 | 9.0 | N/A |
| diisopropylethylamine | 3 | N/A | 27.0 | Density 0.742 g/mL 4.7 mL |
| 1,1-sulfonyldiimidazole | 5.1 | 9.06 | 45.7 | N/A |
| potassium fluoride | 14 | 7.35 | 127 | N/A |
| trifluoroacetic acid | 33 | N/A | 300 | Density 1.49 g/mL 23.1 mL |

TABLE 27C

| Physical Properties of Products | | |
|---|---|---|
| Product | Formula | MM (g/mol) |
| 1H-indol-4-yl sulfurofluoridate | $C_8H_6FNO_3S$ | 215.20 |

TABLE 27D

| Relative Amounts of Products | | | |
|---|---|---|---|
| Product | Theoretical | Actual | Yield |
| 1H-indol-4-yl sulfurofluoridate | 1.9 g | 1.80 g | 93% |

A 40 mL capped vial (gas generation vial) was charged with 1,1,sulfonyldiimidazole (9.06 g, 44.8 mmol), potassium fluoride (7.35 g, 127 mmol), and water (30 mL) and then equipped with a magnetic stir bar. Next, 1H-indole-4-ol (1.2 g, 9.0 mmol), and diisopropylethylamine (4.7 mL, 27.3 mmol) were added to a second 40 mL capped vial (reaction vial) with acetonitrile (25 mL).

A connecting PTFE tube was used to link the gas generation vial with the reaction vial. An empty balloon was attached to the reaction vial to balance overpressure. Trifluoroacetic acid (23.4 mL, 306 mmol) was added via syringe pump over 15 minutes.

Upon completion (45 min) the reaction system was disassembled and evaporated to dryness. The organic residue (from reaction flask) was then reconstituted with ethyl acetate (25 mL) and extracted with an aqueous solution of hydrochloric acid (1M, 2×10 mL). The combined organic extracts were washed with brine (2×10 mL), and then concentrated under vacuum to give 1H-indol-4-yl sulfurofluoridate (1.8 g, 8.36 mmol, 93%) as an off-white powder.

Example XXVIII

The method shown in FIG. 28 was carried out. The reagents and products included a total volume of 10.49 ml, including 8.78 mL of acetonitrile and 1.71 mL of DIPEA with a reaction molarity of 234 mmolar at a temperature of 25° C. Details of the reagents are shown in Table 28A and Table 28B. Details of the products are shown in Table 28C and Table 28D.

TABLE 28A

Physical Properties of Reagents

| Reagent | Formula | MM (g/mol) |
|---|---|---|
| 3-(2-(pyrrolidin-1-yl)ethyl)-1H-indol-4-ol | $C_{14}H_{18}N_2O$ | 230.31 |
| N,N-diisopropylethylamine | $C_8H_{19}N$ | 129.25 |
| 1,1'-sulfonylbis(1H-imidazole) | $C_6H_6N_4O_2S$ | 198.20 |
| potassium fluoride | KF | 58.10 |
| trifluoroacetic acid | $C_2HF_3O_2$ | 114.02 |

TABLE 28B

Relative Amounts of Reagents and Solvents

| Reagent | Eq | M (g) | mmol | Notes |
|---|---|---|---|---|
| 3-(2-(pyrrolidin-1-yl)ethyl)-1H-indol-4-ol | 1 | 0.566 | 2.46 | N/A |
| N,N-diisopropylethylamine | 4 | N/A | 9.8302 | Density 0.742 g/mL Volume 1.71 mL |
| 1,1'-sulfonylbis(1H-imidazole) | 6.5 | 3.2 | 16.00 | N/A |
| potassium fluoride | 15.7 | 2.32 | 40.00 | N/A |
| trifluoroacetic acid | 42.3 | N/A | 104 | Density 1.49 g/mL 8.08 mL |

TABLE 28C

Physical Properties of Products

| Product | Formula | MM (g/mol) |
|---|---|---|
| 1-(fluorosulfonyl)-3-(2-(pyrrolidin-1-yl)ethyl)-1H-indol-4-yl sulfurofluoridate | $C_{14}H_{16}F_2N_2O_5S_2$ | 394.41 |

TABLE 28D

Relative Amounts of Products

| Product | Theoretical | Actual | Yield |
|---|---|---|---|
| 1-(fluorosulfonyl)-3-(2-(pyrrolidin-1-yl)ethyl)-1H-indol-4-yl sulfurofluoridate | 969 mg | 245 mg | 25.3% |

A 20 ml capped vial (gas generation vial) was charged with 1,1,sulfonyldiimidazole (3.2 g, 16.0 mmol), potassium fluoride (2.32 g, 40 mmol), and water (11 mL) and then equipped with a magnetic stir bar. Next, 3-(2-(pyrrolidin-1-yl)ethyl)-1H-indol-4-ol (0.566 g, 2.46 mmol), and diisopropylethylamine (1.7 mL, 9.83 mmol) were added to a second 20 ml capped vial (reaction vial) with acetonitrile (8.78 mL).

A connecting PTFE tube was used to link the gas generation vial with the reaction vial. An empty balloon was attached to the reaction vial to balance overpressure. Trifluoroacetic acid (8.08 mL, 104 mmol) was added via syringe pump over 10 minutes.

Upon completion (8 hours) the reaction system was disassembled, and the contents of the reaction flask was diluted with dichloromethane (100 mL). This solution was washed with water (4×60 mL) and the combined organic fraction was washed with saturated brine (2×60 mL). The dichloromethane layer was dried with sodium sulfate and evaporated to dryness. Residue was suspended in a minimum volume of dichloromethane and purified via column chromatography (12 g silica column, eluting with ethyl acetate) to give 1-(fluorosulfonyl)-3-(2-(pyrrolidin-1-yl)ethyl)-1H-indol-4-yl sulfurofluoridate (245 mg, 0.621 mmol, 25.3%) as a clear oil.

The product was characterized by both 1H NMR (300 MHz, CD2Cl2) δ 7.83 (dd, J=8.1, 1.0 Hz, 1H), 7.44-7.27 (m, 3H), 3.09-2.85 (m, 2H), 2.81-2.68 (m, 2H), 2.58-2.39 (m, 4H), 1.80-1.57 (m, 4H) and 19F NMR (282 MHz, CD2Cl2) δ 54.25, 39.51.

Example XXIX

The method shown in FIG. 29 was carried out. The reagents and products included a total volume of 20 ml of DCM with a reaction molarity of 22 mmolar at a temperature of 25° C. Details of the reagents are shown in Table 29A and Table 29B. Details of the products are shown in Table 29C and Table 29D.

TABLE 29A

Physical Properties of Reagents

| Reagent | Formula | MM (g/mol) |
|---|---|---|
| 3-(2-(pyrrolidin-1-yl)ethyl)-1H-indol-4-ol | $C_{14}H_{18}N_2O$ | 230.31 |
| 1,1'-sulfonylbis(1H-imidazole) | $C_6H_6N_4O_2S$ | 198.20 |
| potassium fluoride | KF | 58.10 |
| trifluoroacetic acid | $C_2HF_3O_2$ | 114.02 |

TABLE 29B

Relative Amounts of Reagents and Solvents

| Reagent | Eq | M (g) | mmol | Notes |
|---|---|---|---|---|
| 3-(2-(pyrrolidin-1-yl)ethyl)-1H-indol-4-ol | 1 | 0.100 | 0.434 | N/A |
| 1,1'-sulfonylbis(1H-imidazole) | 6.5 | 3.2 | 16.00 | N/A |
| potassium fluoride | 15.7 | 2.32 | 40.00 | N/A |
| trifluoroacetic acid | 42.3 | N/A | 104 | Density 1.49 g/mL 8.08 mL |

TABLE 29C

Physical Properties of Products

| Product | Formula | MM (g/mol) |
|---|---|---|
| 3-(2-(pyrrolidin-1-yl)ethyl)-1H-indol-4-yl sulfurofluoridate | $C_{14}H_{17}FN_2O_3S$ | 312.36 |

TABLE 29D

Relative Amounts of Products

| Product | Theoretical | Actual | Yield |
|---|---|---|---|
| 3-(2-(pyrrolidin-1-yl)ethyl)-1H-indol-4-yl sulfurofluoridate | 136 mg | 26 mg | 19% |

A 20 ml capped vial (gas generation vial) was charged with 1,1,sulfonyldiimidazole (3.2 g, 16.0 mmol), potassium fluoride (2.32 g, 40 mmol), and water (11 mL) and then equipped with a magnetic stir bar. Next, 3-(2-(pyrrolidin-1-yl)ethyl)-1H-indol-4-ol (0.566 g, 2.46 mmol) was added to a second 20 ml capped vial (reaction vial) with dichloromethane (20 mL).

A connecting PTFE tube was used to link the gas generation vial with the reaction vial. An empty balloon was attached to the reaction vial to balance overpressure. Trifluoroacetic acid (8.08 mL, 104 mmol) was added via syringe pump over 10 minutes.

Upon completion (2 hours) the reaction system was disassembled, and the heterogenous sultry was filtered. The clear supernatant was evaporated to dryness and the residue was suspended in a minimum volume of dichloromethane and purified via column chromatography (12 g silica column, eluting with a gradient of dichloromethane moving to 10% dichloromethane in methanol) to give 3-(2-(pyrrolidin-1-yl)ethyl)-1H-indol-4-yl sulfurofluoridate (0.026 g, 0.083 mmol, 19%) as a clear oil.

The product was characterized by both 1H NMR (400 MHz, CD2Cl2) δ 10.09 (s, 1H), 7.49 (d, J=8.0 Hz, 1H), 7.35-6.94 (m, 3H), 3.49-3.40 (m, 2H), 3.32 (q, J=5.2 Hz, 4H), 3.01-2.95 (m, 2H), 2.28-1.86 (m, 4H) and 19F NMR (282 MHz, CD2Cl2) δ 39.14.

Example XXX

The method shown in FIG. 30 was carried out. The reagents and products included a total volume of 57 mL, including 50 mL of acetone and 5 mL of water, with a reaction molarity of 98 mmolar at a temperature of 25° C. Details of the reagents are shown in Table 30A and Table 30B. Details of the Products are shown in Table 30C and Table 30D.

TABLE 30A

Physical Properties of Reagents

| Reagent | Formula | MM (g/mol) |
| --- | --- | --- |
| 3-allyl-1H-indol-4-yl dibenzyl phosphate | $C_{25}H_{24}NO_4P$ | 433.44 |
| 2,6-lutidine | $C_7H_9N$ | 107.16 |
| potassium osmate dihydrate | $H_4K_2O_6Os$ | 368.45 |
| 4-methylmorpholine 4-oxide | $C_5H_{11}NO_2$ | 117.15 |

TABLE 30B

Relative Amounts of Reagents and Solvents

| Reagent | Eq | M (g) | mmol | Notes |
| --- | --- | --- | --- | --- |
| 3-allyl-1H-indol-4-yl dibenzyl phosphate | 1 | 2.40 g | 5.54 mmol | N/A |
| acetone | N/A | N/A | N/A | 50 mL |
| water | N/A | N/A | N/A | 5 mL |
| 2,6-lutidine | 2.5 | 1.48 g | 13.8 mmol | Density 0.925 g/mL Volume 1.60 mL |
| potassium osmate dihydrate | 0.03 | 61.2 mg | 1.38 mmol | N/A |
| 4-methylmorpholine 4-oxide | 2.5 | 1.87 g | 13.8 mmol | N/A |

TABLE 30C

Physical Properties of Products

| Product | Formula | MM (g/mol) |
| --- | --- | --- |
| dibenzyl (3-(2,3-dihydroxypropyl)-1H-indol-4-yl) phosphate | $C_{25}H_{26}NO_6P$ | 467.46 |

TABLE 30D

Physical Properties of Products

| Product | Theoretical | Actual | Yield |
| --- | --- | --- | --- |
| dibenzyl (3-(2,3-dihydroxypropyl)-1H-indol-4-yl) phosphate | 2.59 g | 1.32 g | 51.0% |

50 mL of acetone and 5 mL of water was added to a 100 mL round bottom flask containing 3-allyl-1H-indol-4-yl dibenzyl phosphate (2.40 g, 1 Eq, 5.54 mmol). 2,6-lutidine (1.60 mL, 2.5 Eq, 13.8 mmol) was added in one portion. Potassium Osmate (61.2 mg, 3 mol %, 166 μmol) was added in one portion. 4-Methylmorpholine 4-oxide (1.87 g, 2.5 Eq, 13.8 mmol) was added in one portion.

The reaction was stirred vigorously at 25° C. for 6 hours. Upon completion, the reaction was quenched with a saturated solution of sodium thiosulfate (20 mL). Acetone was removed under reduced pressure and the resulting crude mixture was diluted with ethyl acetate (50 mL). The organic phase was separated and was further washed with an aqueous solution of hydrochloric acid (0.5M, 3×20 mL), saturated solution of sodium bicarbonate (20 mL) and brine (20 mL)

The resulting organic extracts were concentrated in vacuo. The crude material was purified by flash chromatography using ethyl acetate:hexanes (9:1) as eluent to afford dibenzyl (3-(2,3-dihydroxypropyl)-1H-indol-4-yl) phosphate (1.32 g, 2.82 mmol, 51.0%) as a clear oil.

The product was characterized by 1H NMR (300 MHz, chloroform-D). The observed peaks on 1H NMR were δ 2.91 (dd, J=14.62, 7.54 Hz, 1H) 3.09 (dd, J=14.28, 5.60 Hz, 1H) 3.49 (dd, J=11.19, 6.40 Hz, 1H) 3.61 (dd, J=11.19, 3.65 Hz, 1H) 3.95-4.06 (m, 1H) 6.95-7.09 (m, 3H) 7.13-7.19 (m, 1H) 7.27-7.37 (m, 10H) 8.24 (br. s., 1H).

Example XXXI

The method shown in FIG. 31 was carried out using a sequential, telescoped procedure. The reagents and products included a total volume of 240 mL, including 160 mL of tert-butanol and 80 mL of water with a reaction molarity of 84.6 mmolar at a temperature of 25° C. Details of the reagents are shown in Table 31A and Table 31B. Details of the Products are shown in Table 31C and Table 31 D.

TABLE 31A

Physical Properties of Reagents

| Reagent | Formula | MM (g/mol) |
| --- | --- | --- |
| dibenzyl (1H-indol-4-yl) phosphate | $C_{22}H_{20}NO_4P$ | 393.38 |
| allyl alcohol | $C_3H_6O$ | 58.1 |
| triethyl borane | $C_6H_{15}B$ | 98.0 |
| tetrakis(triphenylphosphine) palladium | $C_{72}H_{60}P_4Pd$ | 1155.6 |
| 3-allyl-1H-indol-4-yl dibenzyl phosphate | $C_{25}H_{24}NO_4P$ | 433.44 |
| potassium tetrahydroxydioxoosmium | $K_2OsO_6H_4$ | 368.45 |

TABLE 31A-continued

Physical Properties of Reagents

| Reagent | Formula | MM (g/mol) |
|---|---|---|
| potassium carbonate | $K_2CO_3$ | 138.20 |
| potassium ferricyanide | $K_3FeC_6N_6$ | 329.25 |

TABLE 31B

Relative Amounts of Reagents and Solvents

| Reagent | Eq | M (g) | mmol | Notes |
|---|---|---|---|---|
| dibenzyl (1H-indol-4-yl) phosphate | 1 | 10.0 | 25.4 | N/A |
| allyl alcohol | 1.1 | N/A | 28.0 | Density 0.854 g/mol Volume 1.9 mL |
| triethyl borane | 0.8 | N/A | 20.3 | 1.0 M in hexanes Volume 20.3 mL |
| tetrakis(triphenylphosphine) palladium | 0.068 | 2.0 | 1.73 | N/A |
| potassium tetrahydroxydioxidoosmium | 0.02 | 0.150 | 0.406 | N/A |
| potassium carbonate | 4.5 | 12.60 | 91.4 | N/A |
| potassium ferricyanide | 4.5 | 30.10 | 91.4 | N/A |

TABLE 31C

Physical Properties of Products

| Product | Formula | MM (g/mol) |
|---|---|---|
| dibenzyl (3-(2,3-dihydroxypropyl)-1H-indol-4-yl) phosphate | $C_{25}H_{26}NO_6P$ | 467.46 |

TABLE 31D

Relative Amounts of Products

| Product | Theoretical | Actual | Yield |
|---|---|---|---|
| dibenzyl (3-(2,3-dihydroxypropyl)-1H-indol-4-yl) phosphate | 9.49 g | 1.19 g | 12.6% |

Dibenzyl (1H-indol-4-yl) phosphate (10.0 g, 1 Eq, 25.4 mmol) and tetrakis(triphenylphosphine) palladium (2.0 g, 0.068 Eq, 1.73 mmol) were added to a 500 mL flask and sparged with argon. While sparging, THF (254 mL) was added to the flask, followed by allyl alcohol (1.9 mL, 1.1 Eq, 28.0 mmol, and finally triethylborane (1.0 M in hexanes, 20.3 mL, 0.8 Eq, 20.3 mmol).

The reaction was heated at 45° C. and stirred for 5.5 hours under an argon atmosphere. Upon completion, reaction mixture was concentrated under vacuum. Then the crude material was passed down a pad composed of a sequential layer of Celite diatomaceous earth (20 g) and silica gel (100 g) and sand eluting with 1:1 petroleum ether:ethyl acetate.

For the second transformation, tert-butanol (160 mL) and water (80.0 mL) was charged into a 250 mL, screw cap bottle, followed by the crude 3-allyl-1H-indol-4-yl dibenzyl phosphate (8.80 g, 20.3 mmol—isolated from the previous step without purification), potassium ferricyanide (30.1 g, 91.4 mmol) and potassium carbonate (12.6 g, 4.5 Eq, 91.4 mmol). Potassium tetrahydroxydioxidoosmium (150 mg, 406 μmol) was then charged last and the bottle was sealed, ensuring minimal headspace remained. The mixture became heterogenous over time, forcing the stirring to be adjusted to ensure the suspension remained well mixed.

After 4 days, the reaction was completed and now presented as a dark slurry with copious yellow precipitate. The slurry was transferred into a 1 L flask, and treated with methanol (250 mL) to force more solids to crash out of the reaction. The slurry was then filtered over C elite (20 g) and washed with methanol (50 mL). The combined supernatant was concentrated via rotary evaporation until reduced to ~60 mL in volume.

The concentrated residue was extracted with ethyl acetate (2×250 mL). The combined organic phase was then washed with an aqueous solution of hydrochloric acid (1M, 3×300 ml), then saturated sodium bicarbonate solution (100 mL)

The combined organic fractions were dried with sodium sulfate, then passed down a pad composed of Celite diatomaceous earth (20 g), Silica Gel (100 g) and sand (100 g). After collection via vacuum filtration, the organic fraction was evaporated to dryness to give a crude oil. This was purified by column chromatography (20 g silica gel, eluting with petroleum ether to 4:1 petroleum ether: ethyl acetate via linear gradient) to afford dibenzyl (3-(2,3-dihydroxypropyl)-1H-indol-4-yl) phosphate (1.19 g, 2.554 mmol, 12.6%) as a clear oil.

The product was characterized by 1H NMR (400 MHz, CDCl3) δ 8.52 (s, 1H), 7.26 (ddt, J=12.9, 7.0, 2.7 Hz, 13H), 7.10 (dt, J=7.7, 1.1 Hz, 1H), 7.03-6.85 (m, 3H), 5.13-5.02 (m, 4H), 3.54 (dd, J=11.3, 3.5 Hz, 1H), 3.42 (dd, J=11.3, 6.5 Hz, 1H), 3.01 (dd, J=14.5, 5.5 Hz, 1H), 2.86 (dd, J=14.5, 7.6 Hz, 1H).

REFERENCES

Bartolucci, Silvia. Mari, Michele. Di Gregorio, Giovanni. Piersanti, Giovanni. Observations concerning the synthesis of tryptamine homologues and branched tryptamine derivatives via the borrowing hydrogen process: synthesis of psilocin, bufotenin, and serotonin. Department of Biomolecular Sciences. *Tetrahedron*. (2016), 72, 2233-2238.

Blei, Felix. Baldeweg, Florian. Fricke, Janis. Hoffmeister, Dirk. Biocatalytic Production of Psilocybin and Derivatives in Tryptophan Synthase-Enhanced Reactions. *Chem. Eur. J.* (2018), 24, 10028-1003.

Brown, J. B., Henbest, H. B., Jones, E. R. H. 3-Indolylacetaldehyde and 3-Indolylacetone. *J. Chem. Soc.* (1952), 606, No. 0, 3172-3176.

Chadeayne, Andrew R., Pham Duyen N. K., Reid, Brian G., Golen, James A., Manke, David R., Active Metabolite of Aeruginascin (4-Hydroxy-N,N,N-trimethyltryptamine): Synthesis, Structure, and Serotonergic Binding Affinity. *ACS Omega*. (2020), 5, 16940-16943.

Chen, J.-Q., Song, L.-L., Li, F.-X., Shi, Z.-F., Cao, X.-P. Asymmetric Formal Synthesis of (+)-Cycloclavine. *Chem. Commun*, (2017), 53(96), 12902-12905.

Chung, R., Hein, J. E. The More, The Better: Simultaneous In Situ Reaction Monitoring Provides Rapid Mechanistic and Kinetic Insight. Top Catal (2017), 60, 594-608.

Daponte, J. A.; Guo, Y.; Ruck, R. T.; Hein, J. E. Using an automated monitoring platform for investigations of biphasic reactions. *ACS Catal.* 2019, 9(12), 11484-11491.

Dethe, D. H., Boda, R. A Novel Pd-Catalysed Annulation Reaction for the Syntheses of Pyrroloindoles and Pyrroloquinolines. *Chemistry* (2016), 22(1), 106-110.

Dethe, D. H., Erande, R. D., Ranjan, A. Biomimetic Total Syntheses of Borreverine and Flinderole Alkaloids. *J. Org. Chem.* (2013), 78(20), 10106-10120.

Fawzy, A. Palladium(II)-Catalyzed Oxidation of L-Tryptophan by hexacyanoferrate(III) in Perchloric Acid Medium: A Kinetic and Mechanistic Approach. *J. Chem. Sci.* (2016), 128(2), 247-256.

Fricke, Janis. Blei, Felix, Hoffmeister, Dirk. Enzymatic Synthesis of Psilocybin. *Angew. Chem Int. Ed.* (2017), 56, 12352-12355.

Gathergood, Nicholas. Scammells, Peter J., Preparation of the 4-Hydroxytryptamine Scaffold via Palladium-Catalyzed Cyclization: A Practical and Versatile Synthesis of Psilocin. *Organic Letters.* (2003), 5(6), 921-923.

Geiger, Haden A., Wurst, Madeline G., Daniels, Nathan R., DARK Classics in Chemical Neuroscience: Psilocybin. *ACS Chemical Neuroscience.* (2018), 9, 2438-2447.

Gray, R. A. Preparation and Properties of 3-Indoleacetaldehyde, *Arch Biochem Biophys*, (1959), 81(2), 480-488.

Hayashi, Yujiro; Pot economy and one-pot synthesis. *Chem. Sci.* (2016), 7, 866-880.

Hu, Chunmei. Qin, Hua. Cui, Yuxin. Jia, Yanxing. Palladium-catalyzed synthesis of tryptamines and tryptamine homologues: synthesis of psilocin. *Tetrahedron*, (2009), 65, 9075-9080.

Julia, M., Ricalens, F. Synthese de La Psilocine a Partir de Dimethyl Tryptamine. *C. R. Acad. Sc. Paris*, (1969), 269(1), 51-53.

Kargbo, Robert B., Sherwood, Alexander. Walker, Andrew. Cozzi Nicholas V., Dagger, Raymond E., Sable, Jessica. O'Hern, Kelsey. Kaylo, Kristi. Patterson, Tura. Tarpley, Gary. Meisenheimer, Poncho. Direct Phosphorylation of Psilocin Enables Optimized cGMP Kilogram-Scale Manufacture of Psilocybin. *ACS Omega*, (2020), 5, 16959-16966.

Kimura, M., Futamata, M., Mukai, R., Tamaru, Y. Pd-Catalyzed $C_3$-Selective Allylation of Indoles with Allyl Alcohols Promoted by Triethylborane. *J. Am. Chem. Soc.* (2005), 127(13), 4592-4593.

Kodet, J. G., Beutler, J. A., Wiemer, D. F. Synthesis and Structure Activity Relationships of Schweinfurthin Indoles. *Bioorg. Med. Chem.* (2014), 22(8), 2542-2552.

Lv, J., Chen, X., Xue, X.-S., Zhao, B., Liang, Y., Wang, M., Jin, L., Yuan, Y., Han, Y., Zhao, Y., Lu, Y., Zhao, J., Sun, W.-Y., Houk, K. N., Shi, Z. Metal-Free Directed sp2-C—H Borylation. *Nature* (2019), 575(7782), 336-340.

Malig, T. C. Tan, Y.; Wisniewski, S. R.; Higman, C. S.; Carrasquillo-Flores, R.; Ortiz, A.; Purdum, G. E.; Kolotuchinb, S. and Hein, J. E. Development of a telescoped synthesis of 4-(1H)-cyanoimidazole core accelerated by orthogonal reaction monitoring. *React. Chem. Eng.*, (2020), 5, 1421-1428.

Malig, T. C., Yunker, L. P. E., Steiner, S., Hein, J. E. Online High-Performance Liquid Chromatography Analysis of Buchwald-Hartwig Aminations from within an Inert Environment *ACS Catal.* (2020), 10(22), 13236-13244.

Maresh, J. J., Crowe, S. O., Ralko, A. A., Aparece, M. D., Murphy, C. M., Krzeszowiec, M., Mullowney, M. W. Facile One-Pot Synthesis of Tetrahydroisoquinolines from Amino Acids via Hypochlorite-Mediated Decarboxylation and Pictet-Spengler Condensation. *Tetrahedron Lett.* (2014), 55(36), 5047-5051

Mi, C., Meng, X.-G., Liao, X.-H., Peng, X. Selective Oxidative Cleavage of Terminal Olefins into Aldehydes Catalyzed by copper(II) Complex. *RSC Adv.* (2015), 5(85), 69487-69492.

Nichols, David E., Frescas, Stewart. Improvements to the Synthesis of Psilocybin and a Facile Method for Preparing the O-Acetyl Prodrug of Psilocin. *Synthesis.* (1999), 6, 935-938.

Sato, Y.; Liu, J.; Kukor, A. J.; Culhane, J. C.; Tucker, J. L.; Kucera, D. J.; Cochran, B. M. and Hein, J. E. Real-Time Monitoring of Solid-Liquid Slurries: Optimized Synthesis of Tetrabenazine. *Journal Org. Chem.* (2021) 86(20), 14069-14078.

Shirota, Osamu. Hakamata, Wataru. Goda, Yukihiro. Concise Large-Scale Synthesis of Psilocin and Psilocybin, Principal Hallucinogenic Constituents of "Magic Mushroom". *J. Nat. Prod.* (2003) 66, 885-887.

Shultz, M. D., Cao, X., Chen, C. H., Cho, Y. S., Davis, N. R., Eckman, J., Fan, J., Fekete, A., Firestone, B., Flynn, J., Green, J., Growney, J. D., Holmqvist, M., Hsu, M., Jansson, D., Jiang, L., Kwon, P., Liu, G., Lombardo, F., Lu, Q., Majumdar, D., Meta, C., Perez, L., Pu, M., Ramsey, T., Remiszewski, S., Skolnik, S., Traebert, M., Urban, L., Uttamsingh, V., Wang, P., Whitebread, S., Whitehead, L., Yan-Neale, Y., Yao, Y.-M., Zhou, L., Atadja, P. Optimization of the in Vitro Cardiac Safety of Hydroxamate-Based Histone Deacetylase Inhibitors. *J. Med. Chem.* (2011), 54(13), 4752-4772.

Somei, M., Yamada, F., Tamura, M. A Five-Step Synthesis of Psilocin from Indole-3-Carbaldehyde. *Heterocycles* (1998), 49(1), 451.

Tamami, B., Ghasemi, S. Modified Crosslinked Polyacrylamide Anchored Schiff Base-cobalt Complex: A Novel Nano-Sized Heterogeneous Catalyst for Selective Oxidation of Olefins and Alkyl Halides with Hydrogen Peroxide in Aqueous Media. *Appl. Catal.* A (2011), 393(1), 242-250.

Examples Only

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The invention claimed is:

1. A method of synthesizing a tryptamine, comprising:
    allyllating an indole compound comprising an indole ring and optionally a functional group on the indole ring to provide an α-indolepropene;
    oxidizing the α-indolepropene to provide an indoleacetaldehyde; and
    reductively aminating the indoleacetaldehyde to provide the tryptamine,
    wherein oxidizing the α-indolepropene comprises:
        oxidizing the α-indolepropene to provide an indole propyl diol; and
        oxidizing the indole propyl diol to provide the indoleacetaldehyde; and
    wherein oxidizing the indole propyl diol and reductively aminating the indoleacetaldehyde are effected without isolation of intermediates.

2. The method of claim 1, wherein the indole compound comprises the functional group on the indole ring and the functional group on the indole ring is selected from the group consisting of —OH, —OR, —NH$_2$, —NHR, —NR$_2$, —NHCOR, —NO$_2$, —CN, —N$_3$, —COR, —CO$_2$H, —CO$_2$R, —CHO, —RCHO, —R, —B(OR)$_2$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H and SiR$_3$, wherein R is selected from the group consisting of alkyl, acyl, vinyl, propargyl, phenyl and benzyl, and each separate R group may be identical to other R groups or distinct from other R groups.

3. The method of claim 2, wherein the functional group is selected from the group consisting of —PO$_2$(OR)$_2$ wherein R is benzyl, and —SO$_3$F.

4. The method of claim 1, wherein the functional group is located on position 4 of the indole ring, using the numbering of tryptamine.

5. The method of claim 1, wherein allyllating the indole compound and oxidizing the α-indolepropene to provide the indole propyl diol are effected without isolation of intermediates; and
wherein oxidizing the α-indolepropene to provide the indole propyl diol and oxidizing the indole propyl diol are effected without isolation of intermediates.

6. The method of claim 1, wherein reductively aminating the indoleacetaldehyde comprises reductive amination with dimethylamine; with an amine selected from the group consisting of methylamine, ethylamine, isopropylamine, diethylamine, diisopropylamine, methylethylamine, methylisopropylamine and ethylisopropylamine; or with a cyclic secondary amine and the tryptamine comprises a cyclic tertiary amine.

7. The method of claim 1 further comprising substituting the functional group on the indole ring for another functional group.

8. A method of synthesizing a tryptamine, comprising:
reductively aminating a ring-substituted indoleacetaldehyde comprising an indole ring and a functional group on the indole ring to provide the tryptamine,
wherein the indoleacetaldehyde is prepared by a method comprising:
oxidizing a ring-substituted α-indolepropene to provide the indoleacetaldehyde,
wherein the α-indolepropene is prepared by a method comprising: allyllating a substituted indole compound to provide the α-indolepropene, and
wherein oxidizing the α-indolepropene and reductively aminating the indoleacetaldehyde are effected without isolation of intermediates.

9. The method of claim 8, wherein oxidizing the α-indolepropene comprises:
oxidizing the α-indolepropene to provide an indole propyl diol; and
oxidizing the indole propyl diol to provide the indoleacetaldehyde.

10. The method of claim 8, wherein allyllating the substituted indole compound and oxidizing the α-indolepropene are effected without isolation of intermediates.

11. The method of claim 8, wherein reductively aminating the indoleacetaldehyde comprises reductive amination with an amine selected from the group consisting of methylamine, ethylamine, isopropylamine, diethylamine, diisopropylamine, methylethylamine, methylisopropylamine and ethylisopropylamine; or with a cyclic secondary amine and the tryptamine comprises a cyclic tertiary amine.

12. The method of claim 8, wherein the functional group is selected from the group consisting of —OH, —OR, —NH$_2$, —NHR, —NR$_2$, —NHCOR, —NO$_2$, —CN, —N$_3$, —COR, —CO$_2$H, —CO$_2$R, —CHO, —RCHO, —R, —B(OR)$_2$, —F, —Cl, —Br, —I, —At, —PO$_4$, —PO$_2$(OR)$_2$, —SO$_2$Cl, —SH, —SR, —SO$_3$F, —SiH$_3$, —SiRH$_2$, —SiR$_2$H and SiR$_3$, wherein R is selected from the group consisting of alkyl, acyl, vinyl, propargyl, phenyl and benzyl, and each separate R group may be identical to other R groups or distinct from other R groups.

13. The method of claim 12, wherein the functional group is selected from the group consisting of —PO$_2$(OR)$_2$ wherein R is benzyl, and —SO$_3$F; and wherein the functional group is located on position 4 of the indole ring, using the numbering of tryptamine.

14. The method of claim 8, wherein reductively aminating the indoleacetaldehyde comprises reductive amination with dimethylamine.

15. The method of claim 14, wherein the functional group is —PO$_2$(OR)$_2$ wherein R is benzyl; and wherein the functional group is located on position 4 of the indole ring, using the numbering of tryptamine.

16. The method of claim 8, wherein the functional group is selected from the group consisting of —PO$_2$(OR)$_2$ wherein R is benzyl, and —SO$_3$F.

17. The method of claim 8, wherein the functional group is located on position 4 of the indole ring, using the numbering of tryptamine.

18. The method of claim 1, wherein reductively aminating the indoleacetaldehyde comprises reductive amination with a cyclic secondary amine and the tryptamine comprises a cyclic tertiary amine.

19. The method of claim 1, wherein the functional group on the indole ring is located on position 4 of the indole ring, using the numbering of tryptamine, and wherein the functional group on the indole ring is selected from —OH, —OR, —PO$_4$, —PO$_2$(OR)$_2$ and —SO$_3$F, wherein R is selected from the group consisting of alkyl, acyl, vinyl, propargyl, phenyl and benzyl, and each separate R group may be identical to other R groups or distinct from other R groups.

* * * * *